United States Patent
Sack et al.

(10) Patent No.: US 10,646,560 B2
(45) Date of Patent: May 12, 2020

(54) MULTIEPITOPE FUSION ANTIGENS AND VACCINES AND THEIR USE IN TREATMENT OF ENTEROTOXIGENIC DIARRHEA

(71) Applicants: THE JOHNS HOPKINS UNIVERSITY, Baltimore, MD (US); SOUTH DAKOTA STATE UNIVERSITY, Brookings, SD (US)

(72) Inventors: David A. Sack, Fallston, MD (US); Weiping Zhang, Brookings, SD (US)

(73) Assignees: The John Hopkins University, Baltimore, MD (US); South Dakota State University, Brookings, SD (US)

( * ) Notice: Subject to any disclaimer, the term of this patent is extended or adjusted under 35 U.S.C. 154(b) by 0 days.

(21) Appl. No.: 15/105,195

(22) PCT Filed: Dec. 17, 2014

(86) PCT No.: PCT/US2014/070874
§ 371 (c)(1),
(2) Date: Jun. 16, 2016

(87) PCT Pub. No.: WO2015/095335
PCT Pub. Date: Jun. 25, 2015

(65) Prior Publication Data
US 2016/0317638 A1    Nov. 3, 2016

Related U.S. Application Data

(60) Provisional application No. 61/917,105, filed on Dec. 17, 2013.

(51) Int. Cl.
| | | |
|---|---|---|
| *A61K 39/108* | (2006.01) | |
| *C07K 14/245* | (2006.01) | |
| *A61K 39/08* | (2006.01) | |
| *A61K 45/06* | (2006.01) | |
| *A61K 39/00* | (2006.01) | |

(52) U.S. Cl.
CPC .......... *A61K 39/0258* (2013.01); *A61K 39/08* (2013.01); *A61K 45/06* (2013.01); *C07K 14/245* (2013.01); *A61K 2039/575* (2013.01); *A61K 2039/6037* (2013.01); *C07K 2319/00* (2013.01); *C07K 2319/40* (2013.01); *C07K 2319/55* (2013.01)

(58) Field of Classification Search
None
See application file for complete search history.

(56) References Cited

U.S. PATENT DOCUMENTS 6,844,010 B1    1/2005    Setterstrom et al.

OTHER PUBLICATIONS

Ellis (Vaccines, W.B. Saunders Company, Chapter 29, 1988, pp. 568-574).*
Boslego et al (Vaccines and Immunotherapy, 1991, Chapter 17).*
Skolnick et al., the art is unpredictable. Skolnick et al. (Trends in Biotechnology 18: 34-39, 2000).*
Cassels, F, et al., (1992) "Analysis of *Escherichia coli* colonization factor antigen I linear b-cell epitopes, as determined by primate responses, following protein sequence verification", Infection and Immunity, vol. 60, No. 6, pp. 2174-2181.
Evans, D., et al., (1984) "Administration of purified colonization factor antigens (CF!/I, CFA/II) of enterotoxigenic *Escherichia coli*", Gastroenterology, vol. 87, No. 4, pp. 934-940.
Jansson, L. et al., (2006) "The major subunit, CfaB, of colonization factor antigen I from enterotoxigenic *Escherichia coli* is a glycosphingolipid binding protein", Infection and Immunity, vol. 74, No. 6, pp. 3488-3497.
Roan, X., et al., (2014) "Multiepitope fusion antigen induces broadly protective antibodies that prevent adherence of *Escherichia coli* strains expressing colonization factor antigen I (CF!/I), CFA/II, and CFA/IV" Clinical and Vaccine Immunology, vol. 21, No. 2, pp. 243-249.
Black, et al., Global, regional, and national causes of child mortality in 2008: a systematic analysis. Lancet. Jun. 5, 2010;375(9730):1969-87.
Who, Future directions for research on enterotoxigenic *Escherichia coli* vaccines for developing countries. Wkly Epidemiol Rec. Mar. 17, 2006;81(11):97-104.
Dupont, Systematic review: prevention of travellers' diarrhoea. Aliment Pharmacol Ther. May 2008;27(9):741-51.
Sanders. et al., Military importance of diarrhea: lessons from the Middle East. Curr Opin Gastroenterol. Jan. 2005;21(1):9-14.
Wenneras, et al., Prevalence of enterotoxigenic *Escherichia coli*-associated diarrhoea and carrier state in the developing world. J Health Popul Nutr. Dec. 2004;22(4):370-82.
Nataro, et al., Diagnosisand Investigation of Diarrheagenic *Escherichia coli*. Methods Mol Med. 1998;15:387-406.
Svennerholm, From cholera to enterotoxigenic *Escherichia coli* (ETEC) vaccine development. Indian J Med Res. Feb. 2011;133:188-96.
Walker, New vaccines against enteric bacteria for children in less developed countries. Expert Rev Vaccines. Dec. 2005;4(6):807-812.
Zhang, et al., Progress and hurdles in the development of vaccines against enterotoxigenic *Escherichia coli* in humans. Expert Rev Vaccines. Jun. 2012;11(6):677-94.
Gaastra, et al., Colonization factors of human enterotoxigenic *Escherichia coli* (ETEC). Trends Microbiol. Nov. 1996;4(11):444-52.
Gaastra, et al., Antigenic variation within the subunit protein of members of the colonization factor antigen I group of fimbrial proteins in human enterotoxigenic *Escherichia coli*. Int J Med Microbiol. Jun. 2002;292(1):43-50.
Wolf, Occurrence, distribution, and associations of O and H serogroups, colonization factor antigens, and toxins of enterotoxigenic *Escherichia coli*. Clin Microbiol Rev. Oct. 1997; 10(4): 569-584.

(Continued)

*Primary Examiner* — Robert A Zeman
(74) *Attorney, Agent, or Firm* — John Hopkins Technology Ventures

(57) ABSTRACT

Provided herein are polypeptides comprising up to 9 antigenic elements of ETEC virulence determinants: 7 CFA adhesins [CFA/I, CFA/II (CS1, CS2, CS3), CFA/IV (CS4, CS5, CS6)] expressed by the most prevalent and virulent ETEC strains, and 2 toxins expressed by all ETEC strains, were genetically fused together for CFA-toxoid fusion with proteins (CFA/I/II/IV-STa-$_{toxoid}$LT$_{toxoid}$). Methods for making these polypeptides and their use in the treatment of ETEC related disease are also provided.

6 Claims, 24 Drawing Sheets

Specification includes a Sequence Listing.

(56) References Cited

OTHER PUBLICATIONS

Qadri, et al., Enterotoxigenic *Escherichia coli* in developing countries: epidemiology, microbiology, clinical features, treatment, and prevention. Clin Microbiol Rev. Jul. 2005;18(3):465-83.

Sack, et al., Randomised, double-blind, safety and efficacy of a killed oral vaccine for enterotoxigenic *E. coli* diarrhoea of travellers to Guatemala and Mexico. Vaccine. May 30, 2007;25(22):4392-400.

Jetborn, et al., Safety and immunogenicity of an oral inactivated enterotoxigenic *Escherichia coli* vaccine. Vaccine. Jan.-Feb. 1998;16(2-3):255-60.

Harro, et al., A Combination Vaccine Consisting of Three Live Attenuated Enterotoxigenic *Escherichia coli* Strains Expressing a Range of Colonization Factors and Heat-Labile Toxin Subunit B Is Well Tolerated and Immunogenic in a Placebo-Controlled Double-Blind Phase I Trial in Healthy Adults. Clin Vaccine Immunol. Dec. 2011; 18(12): 2118-2127.

Turner, et al., Generation and characterization of a live attenuated enterotoxigenic *Escherichia coli* combination vaccine expressing six colonization factors and heat-labile toxin subunit B. Clin Vaccine Immunol. Dec. 2011;18(12):2128-35.

Wenneras, et al., Antibody-secreting cells in human peripheral blood after oral immunization with an inactivated enterotoxigenic *Escherichia coli* vaccine. Infect Immun. Jul. 1992; 60(7): 2605-2611.

Ahren, et al., Intestinal antibody response after oral immunization with a prototype cholera B subunit-colonization factor antigen enterotoxigenic *Escherichia coli* vaccine. Vaccine. 1993;11(9):929-34.

Ahren, et al., Intestinal immune responses to an inactivated oral enterotoxigenic *Escherichia coli* vaccine and associated immunoglobulin A responses in blood. Infect Immun. Jul. 1998;66(7):3311-6.

Savarino, et al., Introductory evaluation of an oral, killed whole cell enterotoxigenic *Escherichia coli* plus cholera toxin B subunit vaccine in Egyptian infants. Pediatr Infect Dis J. Apr. 2002;21(4):322-30.

Hall, et al., Induction of systemic antifimbria and antitoxin antibody responses in Egyptian children and adults by an oral, killed enterotoxigenic *Escherichia coli* plus cholera toxin B subunit vaccine. Infect Immun. May 2001;69(5):2853-7.

QADRI, et al., Safety and immunogenicity of an oral, inactivated enterotoxigenic *Escherichia coli* plus cholera toxin B subunit vaccine in Bangladeshi adults and children. Vaccine. Jun. 1, 2000;18(24):2704-12.

Qadri, et al., Safety and immunogenicity of an oral, inactivated enterotoxigenic *Escherichia coli* plus cholera toxin B subunit vaccine in Bangladeshi children 18-36 months of age. Vaccine. Jun. 2, 2003;21(19-20):2394-403.

Qadri, et al., Reduced doses of oral killed enterotoxigenic *Escherichia coli* plus cholera toxin B subunit vaccine is safe and immunogenic in Bangladeshi infants 6-17 months of age: dosing studies in different age groups. Vaccine. Mar. 6, 2006;24(10):1726-33.

Svennerholm, et al., Vaccines against enterotoxigenic *Escherichia coli*. Expert Rev Vaccines. Aug. 2008;7(6):795-804.

Tobias, et al., Construction and expression of immunogenic hybrid enterotoxigenic *Escherichia coli* CAF/I and CS2 colonization fimbriae for use in vaccines. Appl Microbiol Biotechnol. Jul. 2010;87(4):1355-65.

Perez-Casal, et al., Gene encoding the major subunit of CS1 pili of human enterotoxigenic *Escherichia coli*. Infect Immun. Nov. 1990; 58(11): 3594-3600.

Froehlich, et al., Genes for CS2 pili of enterotoxigenic *Escherichia coil* and their interchangeability with those for CS1 pili. Infect Immun. Dec. 1995;63(12):4849-56.

Cuff, et al., JPred: a consensus secondary structure prediction server. Bioinformatics. 1998;14(10):892-3.

Von Heijne, Membrane protein structure prediction. Hydrophobicity analysis and the positive-inside rule. J Mol Biol. May 20, 1992;225(2):487-94.

Odorico, et al., BEPITOPE: predicting the location of continuous epitopes and patterns in proteins. J Mol Recognit. Jan.-Feb. 2003;16(1):20-2.

Hopp, et al., Prediction of protein antigenic determinants from amino acid sequences. Proc Natl Acad Sci U S A. Jun. 1981;78(6):3824-8.

Levitt, Conformational preferences of amino acids in globular proteins. Biochemistry. Oct. 3, 1978;17(20):4277-85.

Zimmerman, et al., The characterization of amino acid sequences in proteins by statistical methods. J Theor Biol. Nov. 1968;21(2):170-201.

Zhang, et al., Genetic fusions of heat-labile (LT) and heat-stable (ST) toxoids of porcine enterotoxigenic *Escherichia coli* elicit neutralizing anti-LT and anti-STa antibodies. Infect Immun. Jan. 2010;78(1):316-25.

Ruan, et al., A tripartite fusion, FaeG-FedF-LT(192)A2:B, of enterotoxigenic *Escherichia coli* (ETEC) elicits antibodies that neutralize cholera toxin, inhibit adherence of K88 (F4) and F18 fimbriae, and protect pigs against K88ac/heat-labile toxin infection. Clin Vaccine Immunol. Oct. 2011;18(10):1593-9.

Zhang, et al., *Escherichia coli* K88ac fimbriae expressing heat-labile and heat-stable (STa) toxin epitopes elicit antibodies that neutralize cholera toxin and STa toxin and inhibit adherence of K88ac fimbrial *E. coli*. Clin Vaccine Immunol. Dec. 2010;17(12):1859-67.

Liu, et al., Heat-Labile- and Heat-Stable-Toxoid Fusions (LTR192G-STaP13F) of Human Enterotoxigenic *Escherichia coli* Elicit Neutralizing Antitoxin Antibodies. Infect Immun. Oct. 2011; 79(10): 4002-4009.

Darfeuille-Michaud, et al., Adhesion of enterotoxigenic *Escherichia coli* to the human colon carcinoma cell line Caco-2 in culture. Infect Immun. Apr. 1990; 58(4): 893-902.

Viboud, et al., Binding of enterotoxigenic *Escherichia coli* expressing different colonization factors to tissue-cultured Caco-2 cells and to isolated human enterocytes. Microb Pathog. Aug. 1996;21(2):139-47.

Saha, et al., "Prediction methods for B-cell Epitopes", Methods in Molecular Biology (2007) vol. 409.

\* cited by examiner

CFA multiepitope fusion antigen (MEFA) sequences:

ATGGGCAGCAGCCATCATNATCATCATCACAGCAGCGGCCTGGTGCCGCGCGGCAGC
CATATGGCTAGCGCAGTAGAGGATTTTTTCATTGTTCCAGTTTCTGGAGATCCTGCAATT
GATCTTTTGCAAGCTGATGGCAATGCTCTGCCATCAGCTGTAAAGTTAGCTTATTCTCC
CGCATCAAAAACTAATACTTTGGTGGGTGTTTTGACTCTTGTACATACAAACGATGCAAC
TAAAAAAAATGTACTAGTTAAGCTTGTAACACCACAGCTTACAGATGTTCTGAATCCAAC
CCTGCAAATTCCTGTTTCTGTGCAGGTAACGGTCTACCCTGTTTCTACAACAGCCAAAG
AATTTGAAGCTGCTGCTTTGGGATATTCTGCATCCGGTGTAAATGGCTTGGTGTCAATT
GTGCTTACTGTAATTAGCGCTGCACCTAAAACTGCCGGTACCGCCCCAACTGCAGGAA
ACTATTCAGGAGTAGTATCTCTTGTAATGACTTTGGGAGCC TGATAA (SEQ ID NO: 27)

atgggcagcagccatcatnatcatcatcacagcagcggcctggtgccgcgcggcagccat
M G S S H H H H H H S S G L V P R G S H
atggctagcgcagtagaggatttttcattgttccagtttctggagatcctgcaattgat
M A S A V E D F F I V P V S G D P A I D
cttttgcaagctgatggcaatgctctgccatcagctgtaaagttagcttattctcccgca
L L Q A D G N A L P S A V K L A Y S P A
tcaaaaactaatactttggtgggtgttttgactcttgtacatacaaacgatgcaactaaa
S K T N T L V G V L T L V H T N D A T K
aaaaatgtactagttaagcttgtaacaccacagcttacagatgttctgaatccaaccctg
K N V L V K L V T P Q L T D V L N P T L
caaattcctgtttctgtgcaggtaacggtctaccctgtttctacaacagccaaagaattt
Q I P V S V Q V T V Y P V S T T A K E F
gaagctgctgctttgggatattctgcatccggtgtaaatggcttggtgtcaattgtgctt
E A A A L G Y S A S G V N G L V S I V L
actgtaattagcgctgcacctaaaactgccggtaccgccccaactgcaggaaaactattca
T V I S A A P K T A G T A P T A G N Y S
ggagtagtatctcttgtaatgactttgggagcctgataa
G V V S L V M T L G A (SEQ ID NOS:1, 27)

Multiepitope CFA protein AA sequence

M G S S H H H H H H S S G L V P R G S H M A S A V E D F F I V P V S
G D P A I D L L Q A D G N A L P S A V K L A Y S P A S K T N T L V G
V L T L V H T N D A T K K N V L V K L V T P Q L T D V L N P T L Q I P
V S V Q V T V Y P V S T T A K E F E A A A L G Y S A S G V N G L V S
I V L T V I S A A P K T A G T A P T A G N Y S G V V S L V M T L G A
(SEQ ID NO: 1)

FIG. 4

PANEL A
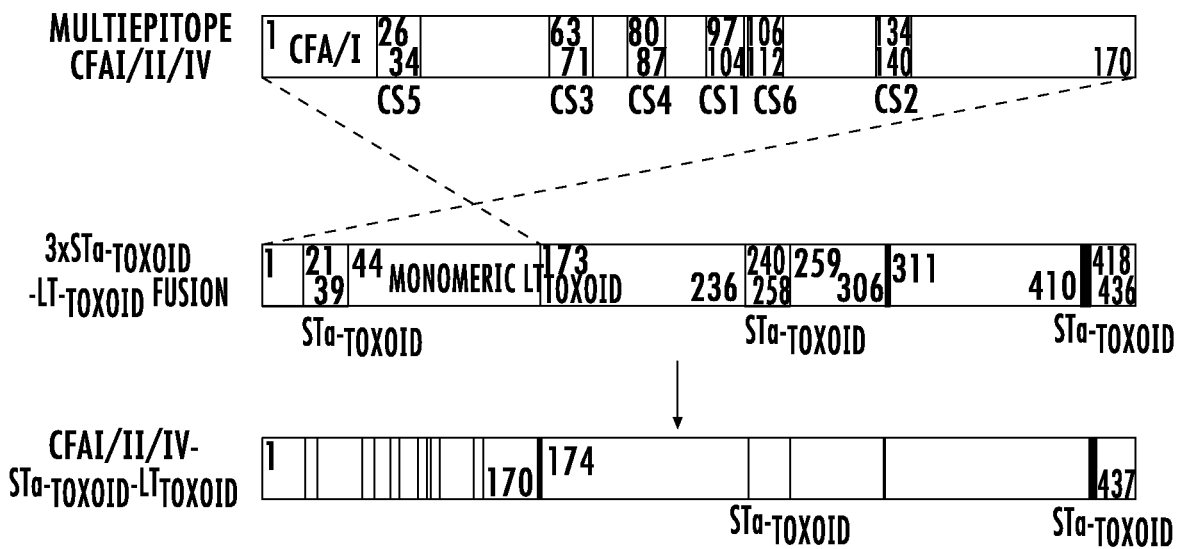
PANEL B
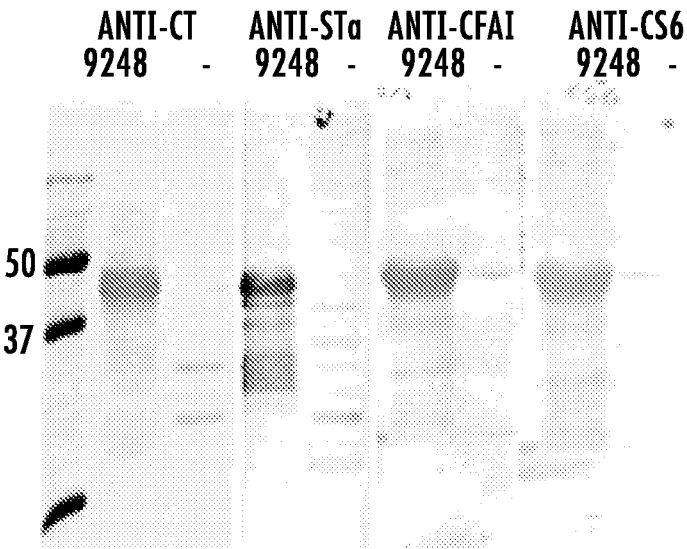
9248= P9208/BL21
9208=CFAI/II/IV-STa14Q-LTB-STa14Q IN PET28a/DH5a
FIG. 5

Nucleotide sequence of CFA-toxoid MEFA CFA/I/II/IV-STaA14Q-LTtoxoid

ATGGGCAGCAGCCATCATNATCATCATCACAGCAGCGGCCTGGTGCCGCGCGGCAGCCATATGGCT
AGCGCAGTAGAGGATTTTTTTCATTGTTCCAGTTTCTGGAGATCCTGCAATTGATCTTTTGCAAGCTGA
TGGCAATGCTCTGCCATCAGCTGTAAAGTTAGCTTATTCTCCCGCATCAAAAACTAATACTTTGGTGG
GTGTTTTGACTCTTGTACATACAAACGATGCAACTAAAAAAAATGTACTAGTTAAGCTTGTAACACCA
CAGCTTACAGATGTTCTGAATCCAACCCTGCAAATTCCTGTTTCTGTGCAGGTAACGGTCTACCCTGT
TTCTACAACAGCCAAAGAATTTGAAGCTGCTGCTTTGGGATATTCTGCATCCGGTGTAAATGGCTTG
GTGTCAATTGTGCTTACTGTAATTAGCGCTGCACCTAAAACTGCCGGTACCGCCCAACTGCAGGAA
ACTATTCAGGAGTAGTATCTCTTGTAATGACTTTGGGAGCCTTTGGTGTGATTGATGAACGATTACAT
CGTAACAGGGAATATAGAGACCGGTATTACAGAAATCTGAATATAGCTCCGGCAGAGGATGGTTAC
AGATTAGCAGGTTTCCCACCGGATCACCAAGCTTGGAGAGAAGAACCCTGGATTCATCATGCACCAC
AAGGTTGTGGAAATTCATCAGGAGGGCCGGTCGACATGAATAGTAGCAATTACTGCTGTGAATTGT
GTTGTAATCCTCAGTGTACCGGGTGCTATACAATTACAGGTGATACTTGTAATGAGGAGACCCAGAA
TCTGAGCACAATATATCTCAGGAAATATCAATCAAAAGTTAAGAGGCAGATATTTTCAGACTATCAG
TCAGAGGTTGACATATATAACAGAATTCGGAATGAATTAGGGCCGGGGCCCGCTCCCCAGTCTATTA
CAGAACTATGTTCGGAATATCGCAACACACAAATATATACGATAAATGACAAGATACTATCATATAC
GGAATCGATGGCAGGCAAAAGAGAAATGGTTATCATTACATTTAAGAGCGGCGCAACATTTCAGGT
CGAAGTCCCGGGCAGTCAACATATAGACTCCCAAAAAAAAGCCATTGAAAGGATGAAGGACACATT
AAGAATCACATATCTGACCGAGACCAAAATTGATAAATTATGTGTATGGAATAATAAAACCCCCAAT
TCAATTGCGGCAATCAGTGATCCCCGGGTACCGAGCTCGATGAATAGTAGCAATTACTGCTGTGAAT
TGTGTTGTAATCCTCAGTGTACCGGGTGCTATTAATAACGGCCG (SEQ ID NO: 28)

*FIG. 10*

Nucleotide and amino acid sequences of CFA-toxoid MEFA CFA/I/II/IV-STaA14Q-LTtoxoid

```
atgggcagcagccatcatcatcatcatcacagcagcggcctggtgccgcgcggcagccat
 M  G  S  S  H  H  H  H  H  H  S  S  G  L  V  P  R  G  S  H
atggctagcgcagtagaggattttttcattgttccagtttctggagatcctgcaattgat
 M  A  S  A  V  E  D  F  F  I  V  P  V  S  G  D  P  A  I  D
cttttgcaagctgatggcaatgctctgccatcagctgtaaagttagcttattctcccgca
 L  L  Q  A  D  G  N  A  L  P  S  A  V  K  L  A  Y  S  P  A
tcaaaaactaatactttggtgggtgttttgactcttgtacatacaaacgatgcaactaaa
 S  K  T  N  T  L  V  G  V  L  T  L  V  H  T  N  D  A  T  K
aaaaatgtactagttaagcttgtaacaccacagcttacagatgttctgaatccaaccctg
 K  N  V  L  V  K  L  V  T  P  Q  L  T  D  V  L  N  P  T  L
caaattcctgtttctgtgcaggtaacggtctaccctgtttctacaacagccaaagaattt
 Q  I  P  V  S  V  Q  V  T  V  Y  P  V  S  T  T  A  K  E  F
gaagctgctgctttgggatattctgcatccggtgtaaatggcttggtgtcaattgtgctt
 E  A  A  A  L  G  Y  S  A  S  G  V  N  G  L  V  S  I  V  L
actgtaattagcgctgcacctaaaactgccggtaccgccccaactgcaggaaactattca
 T  V  I  S  A  A  P  K  T  A  G  T  A  P  T  A  G  N  Y  S
ggagtagtatctcttgtaatgactttggggagcctttggtgtgattgatgaacgattacat
 G  V  V  S  L  V  M  T  L  G  A  F  G  V  I  D  E  R  L  H
cgtaacagggaatatagagaccggtattacagaaatctgaatatagctccggcagaggat
 R  N  R  E  Y  R  D  R  Y  Y  R  N  L  N  I  A  P  A  E  D
ggttacagattagcaggttttccaccggatcaccaagcttggagagaagaaccctggatt
 G  Y  R  L  A  G  F  P  P  D  H  Q  A  W  R  E  E  P  W  I
catcatgcaccacaaggttgtggaaattcatcaggagggccggtcgacatgaatagtagc
 H  H  A  P  Q  G  C  G  N  S  S  G  G  P  V  D  M  N  S  S
aattactgctgtgaattgtgttgtaatcctcagtgtaccggggtgctatacaattacaggt
 N  Y  C  C  E  L  C  C  N  P  Q  C  T  G  C  Y  T  I  T  G
gatacttgtaatgaggagacccagaatctgagcacaatatatctcaggaaatatcaatca
 D  T  C  N  E  E  T  Q  N  L  S  T  I  Y  L  R  K  Y  Q  S
aaagttaagaggcagatattttcagactatcagtcagaggttgacatatataacagaatt
 K  V  K  R  Q  I  F  S  D  Y  Q  S  E  V  D  I  Y  N  R  I
cggaatgaattagggccggggccgactccccagtctattacagaactatgttcggaatat
 R  N  E  L  G  P  G  P  A  P  Q  S  I  T  E  L  C  S  E  Y
cgcaacacacaaatatatacgataaatgacaagatactatcatatacggaatcgatggca
 R  N  T  Q  I  Y  T  I  N  D  K  I  L  S  Y  T  E  S  M  A
ggcaaaagagaaatggttatcattacatttaagagcggcgcaacatttcaggtcgaagtc
 G  K  R  E  M  V  I  I  T  F  K  S  G  A  T  F  Q  V  E  V
ccgggcagtcaacatatagactcccaaaaaaaagccattgaaaggatgaaggacacatta
 P  G  S  Q  H  I  D  S  Q  K  K  A  I  E  R  M  K  D  T  L
agaatcacatatctgaccgagaccaaaattgataaattatgtgtatggaataataaaacc
 R  I  T  Y  L  T  E  T  K  I  D  K  L  C  V  W  N  N  K  T
cccaattcaattgcggcaatcagtgatcccgggtaccgagctcgatgaatagtagcaat
 P  N  S  I  A  A  I  S  D  P  R  V  P  S  S  M  N  S  S  N
tactgctgtgaattgtgttgtaatcctcagtgtaccggggtgctattaataacggccg
 Y  C  C  E  L  C  C  N  P  Q  C  T  G  C  Y     (SEQ ID NOS: 2, 28)
```

(AAs in no-color are backbone of CFA1; in grey are epitopes of CS5, CS3, CS4, CS1, CS6 and CS2; in brown is CFA1 epitope; in yellow are of LTA$^{131-240}$ & LTB$^{1-100}$; in red are STa toxoid, and in purple are of linkers.)

*FIG. 11*

CFA-toxoid MEFA CFA/I/II/IV-STaA14Q-LTtoxoid fusion protein AA
sequence, 435 amino acids with a predict molecular weight of 47.56 kilodaltons.

```
M G S S H H H H H H S S G L V P R G S H M A S A V E D F F I V P V
S G D P A I D L L Q A D G N A L P S A V K L A Y S P A S K T N T L V
G V L T L V H T N D A T K K N V L V K L V T P Q L T D V L N P T L
Q I P V S V Q V T V Y P V S T T A K E F E A A A L G Y S A S G V N G
L V S I V L T V I S A A P K T A G T A P T A G N Y S G V V S L V M T
L G A F G V I D E R L H R N E Y R D R Y Y R N L N I A P A E D G
Y R L A G F P P D H Q A W R E E P W I H H A P Q G C G N S S G G
P V D M N S S N Y C C E L C C N P Q C T G C Y T I T G D T C N E E
T Q N L S T I Y L R K Y Q S K V K R Q I F S D Y Q S E V D I Y N R I
R N E L G P G P A P Q S I T E L C S E Y R N T Q I Y T I N D K I L S
Y T E S M A G K R E M V I I T F K S G A T F Q V E V P G S Q H I D S
Q K K A I E R M K D T L R I T Y L T E T K I D K L C V W N N K T P
N S I A A I S D P R V P S S M N S S N Y C C E L C C N P Q C T G C Y
```
- -(SEQ ID NO: 2)

FIG. 12

Nucleotide sequence of CFA-toxoid MEFA CFA/I/II/IV-STaN12S-LTtoxoid

ATGGGCAGCAGCCATCATNATCATCATCACAGCAGCGGCCTGGTGCCGCGCGGCAGCCATATGGCT
AGCGCAGTAGAGGATTTTTTCATTGTTCCAGTTTCTGGAGATCCTGCAATTGATCTTTTGCAAGCTGA
TGGCAATGCTCTGCCATCAGCTGTAAAGTTAGCTTATTCTCCCGCATCAAAAACTAATACTTTGGTGG
GTGTTTTGACTCTTGTACATACAAACGATGCAACTAAAAAAAATGTACTAGTTAAGCTTGTAACACCA
CAGCTTACAGATGTTCTGAATCCAACCCTGCAAATTCCTGTTTCTGTGCAGGTAACGGTCTACCCTGT
TTCTACAACAGCCAAAGAATTTGAAGCTGCTGCTTTGGGATATTCTGCATCCGGTGTAAATGGCTTG
GTGTCAATTGTGCTTACTGTAATTAGCGCTGCACCTAAAACTGCCGGTACCGCCCCAACTGCAGGAA
ACTATTCAGGAGTAGTATCTCTTGTAATGACTTTGGGAGCCTTTGGTGTGATTGATGAACGATTACAT
CGTAACAGGGAATATAGAGACCGGTATTACAGAAATCTGAATATAGCTCCGGCAGAGGATGGTTAC
AGATTAGCAGGTTTCCCACCGGATCACCAAGCTTGGAGAGAAGAACCCTGGATTCATCATGCACCAC
AAGGTTGTGGAAATTCATCAGGAGGGCCGGTCGACATGAATAGTAGCAATTACTGCTGTGAATTGT
GTTGTAGCCCTGCTTGTACCGGGTGCTATACAATTACAGGTGATACTTGTAATGAGGAGACCCAGAA
TCTGAGCACAATATATCTCAGGAAATATCAATCAAAAGTTAAGAGGCAGATATTTTCAGACTATCAG
TCAGAGGTTGACATATATAACAGAATTCGGAATGAATTAGGGCCGGGGCCCGCTCCCCAGTCTATTA
CAGAACTATGTTCGGAATATCGCAACACACAAATATATACGATAAATGACAAGATACTATCATATAC
GGAATCGATGGCAGGCAAAAGAGAAATGGTTATCATTACATTTAAGAGCGGCGCAACATTTCAGGT
CGAAGTCCCGGGCAGTCAACATATAGACTCCCAAAAAAAAGCCATTGAAAGGATGAAGGACACATT
AAGAATCACATATCTGACCGAGACCAAAATTGATAAATTATGTGTATGGAATAATAAAACCCCCAAT
TCAATTGCGGCAATCAGTGATCCCCGGGTACCGAGCTCGATGAATAGTAGCAATTACTGCTGTGAAT
TGTGTTGTAGCCCTGCTTGTACCGGGTGCTATTAATAACGGCCG (SEQ ID NO: 29)

FIG. 13

Nucleotide and amino acid sequences of CFA-toxoid MEFA 'CFA/I/II/IV-STaN12S-LTtoxoid

```
atgggcagcagccatcatnatcatcatcacagcagcggcctggtgccgcgcggcagccat
 M  G  S  S  H  H  H  H  H  H  S  S  G  L  V  P  R  G  S  H atggctagcgcagtagaggatttttcattgttccagtttctggagatcctgcaattgat
 M  A  S  A  V  E  D  F  F  I  V  P  V  S  G  D  P  A  I  D cttttgcaagctgatggcaatgctctgccatcagctgtaaagttagcttattctcccgca
 L  L  Q  A  D  G  N  A  L  P  S  A  V  K  L  A  Y  S  P  A tcaaaaactaatactttggtgggtgtttgactcttgtacatacaaacgatgcaactaaa
 S  K  T  N  T  L  V  G  V  L  T  L  V  H  T  N  D  A  T  K aaaaatgtactagttaagcttgtaacaccacagcttacagatgttctgaatccaaccctg
 K  N  V  L  V  K  L  V  T  P  Q  L  T  D  V  L  N  P  T  L caaattcctgtttctgtgcaggtaacggtctaccctgtttctacaacagccaaagaattt
 Q  I  P  V  S  V  Q  V  T  V  Y  P  V  S  T  T  A  K  E  F gaagctgctgctttgggatattctgcatccggtgtaaatggcttggtgtcaattgtgctt
 E  A  A  A  L  G  Y  S  A  S  G  V  N  G  L  V  S  I  V  L actgtaattagcgctgcacctaaaactgccggtaccgccccaactgcaggaaactattca
 T  V  I  S  A  A  P  K  T  A  G  T  A  P  T  A  G  N  Y  S ggagtagtatctcttgtaatgacttttgggagcctttggtgtgattgatgaacgattacat
 G  V  V  S  L  V  M  T  L  G  A  F  G  V  I  D  E  R  L  H cgtaacagggaatatagagaccggtattacagaaatctgaatatagctccggcagaggat
 R  N  R  E  Y  R  D  R  Y  Y  R  N  L  N  I  A  P  A  E  D ggttacagattagcaggtttcccaccggatcaccaagcttggagagaagaaccctggatt
 G  Y  R  L  A  G  F  P  P  D  H  Q  A  W  R  E  E  P  W  I catcatgcaccacaaggttgtggaaattcatcaggagggccggtcgacatgaatagtagc
 H  H  A  P  Q  G  C  G  N  S  S  G  G  P  V  D  M  N  S  S aattactgctgtgaattgtgttgtagccctgcttgtaccgggtgctatacaattacaggt
 N  Y  C  C  E  L  C  C  S  P  A  C  T  G  C  Y  T  I  T  G gatacttgtaatgaggagacccagaatctgagcacaatatatctcaggaaatatcaatca
 D  T  C  N  E  E  T  Q  N  L  S  T  I  Y  L  R  K  Y  Q  S aaagttaagaggcagatattttcagactatcagtcagaggttgacatatataacagaatt
 K  V  K  R  Q  I  F  S  D  Y  Q  S  E  V  D  I  Y  N  R  I cggaatgaattagggccggggcccgctccccagtctattacagaactatgttcggaatat
 R  N  E  L  G  P  G  P  A  P  Q  S  I  T  E  L  C  S  E  Y cgcaacacacacaaatatatacgataaatgacaagatactatcatatacggaatcgatggca
 R  N  T  Q  I  Y  T  I  N  D  K  I  L  S  Y  T  E  S  M  A ggcaaaagagagaaatggttatcattacatttaagagcggcgcaacatttcaggtcgaagtc
 G  K  R  E  M  V  I  I  T  F  K  S  G  A  T  F  Q  V  E  V ccgggcagtcaacatatagactcccaaaaaaaagccattgaaaggatgaaggacacatta
 P  G  S  Q  H  I  D  S  Q  K  K  A  I  E  R  M  K  D  T  L agaatcacatatctgaccgagaccaaaattgataaattatgtgtatggaataataaaacc
 R  I  T  Y  L  T  E  T  K  I  D  K  L  C  V  W  N  N  K  T cccaattcaattgcggcaatcagtgatccccgggtaccgagctcgatgaatagtagcaat
 P  N  S  I  A  A  I  S  D  P  R  V  P  S  S  M  N  S  S  N tactgctgtgaattgtgttgtagccctgcttgtaccgggtgctattaataacggccg
 Y  C  C  E  L  C  C  N  P  A  C  T  G  C  Y  (SEQ ID NOS: 3, 29)
```

(AAs in no-color are backbone of CFA1; in grey are epitopes of CS5, CS3, CS4, CS1, CS6 and CS2; in brown is CFA1 epitope; in yellow are of LTA$^{131-240}$ & LTB$^{1-100}$; in green are STa toxoid STaN12S, and in purple are of linkers.)

FIG. 14

CFA-toxoid MEFA CFA/I/II/IV-STaN12S-LTtoxoid AA sequence, 435 amino acids with a predict molecular weight of 47.56 kilodaltons.

```
MGSSHHHHHHSSGLVPRGSHMASAVEDFFWPV
SGDPAIDLLQADGNALPSAVKLAYSPASKTNTL
GVLVLVHTNDATKKNVTVKAVTPQLTDVLNPTL
QLPVSVQVTVVPSTTAKEFEAAALGYSASGVN
GVLVLTVISAAPKTAGTAPTAGNYSGVVSLVM
TLGAFGVIDERLHRNREYRDRYYRNLNIAPAED
GYRLAGFPPDHQAWREEPWIHHAPQGCGNSSG
GPVIDMNSSNYCCELCCSPACTGCYTITGDTCNEE
TQNLSTIYLRKYQSKVKRQIFSDYQSEVDIYNR
IRNELGPGPAPQSITELCSEYRNTQIYTINDKIL
SYTESMAGKREMVIITFKSGATFQVEVPGSQHID
SQKKATERMKDTLRITYLTETKIDKLCVWNNKT
P
NSIAAISDPRVPSSMNSSNYCCELCCSPACTGCY
```
- -(SEQ ID NO: 3)

STaA14Q nucleotide sequence

Atgaatagtagcaattactgctgtgaattgtgttgtaatcctcagtgtaccgggtgctat (SEQ ID NO: 30)

STaA14Q amino acid sequence

M N S S N Y C C E L C C N P Q C T G C Y (SEQ ID NO: 13)

STaN12S nucleotide sequence atgaatagtagcaattactgctgtgaattgtgttgtagccctgcttgtaccgggtgctat (SEQ ID NO: 31)

STaN12S amino acid sequence
M N S S N Y C C E L C C S P A C T G C Y (SEQ ID NO: 14)

LTA(131-140) amino acid sequence

```
FGVIDERLHRNREYRDRYYRNLNIAPAEDGYRL
AGFPPDHQAWREEPWIHHAPQGCGNSSGTITGD
TCNEETQNLSTIYLRKYQSKVKRQIFSDYQSEV
DIYNRIRNEL (SEQ ID NO: 11)
```

LTB (1-100) amino acid sequence

```
APQSITELCSEYRNTQIYTINDKILSYTESMAGK
REMVIITFKSGATFQVEVPGSQHIDSQKKATER
MKDTLRITYLTETKIDKLCVWNNKTPNSIAAIS
```

FIG. 15

Sequences of the his-tag-less CFA-3xSTaN12S-dmLT MEFA (9419):

I. Nucleotide sequence (with pET28a vector sequence)
NNGCATTAGGAAGCAGCCCAGTAGTAGGTTGAGGCCGTTGAGCACCGCCGCCGCAAGGAATGGTGCATGCAAGGA
GATGGCGCCCAACAGTCCCCCGGCCACGGGGCCTGCCACCATACCCACGCCGAAACAAGCGCTCATGAGCCCGAA
GTGGCGAGCCCGATCTTCCCCATCGGTGATGTCGGCGATATAGGCGCCAGCAACCGCACCTGTGGCGCCGGTGAT
GCCGGCCACGATGCGTCCGGCGTAGAGGATCGAGATCTCGATCCCGCGAAATTAATACGACTCACTATAGGGGAA
TTGTGAGCGGATAACAATTCCCCTCTAGAAATAATTTTGTTTAACTTTAAGAAGGAGATATACCATGGAA
ATGGCTAGCATGAATAGTAGCAATTACTGCTGTGAATTGTGTTGTAGCCCTGCTTGTACCGGGTGCTATGGGCCG
GGGCCCAATGGCGACAAATTATACCGTGCTGACTCTAGACCCCCAGATGAAATAAAACGTTCCGGAGGTCTTATG
CCCAGAGGGCATAATGAGTACATGGCTAGCGCAGTAGAGGATTTTTTCATTGTTCCAGTTTCTGGAGATCCTGCA
ATTGATCTTTTGCAAGCTGATGGCAATGCTCTGCCATCAGCTGTAAAGTTAGCTTATTCTCCCGCATCAAAAACT
AATACTTTGGTGGGTGTTTTGACTCTTGTACATACAAACGATGCAACTAAAAAAAATGTACTAGTTAAGCTTGTA
ACACCACAGCTTACAGATGTTCTGAATCCAACCCTGCAAATTCCTGTTTCTGTGCAGGTAACGGTCTACCCTGTT
TCTACAACAGCCAAAGAATTTGAAGCTGCTGCTTTGGGATATTCTGCATCCGGTGTAAATGGCTTGGTGTCAATT
GTGCTTACTGTAATTAGCGCTGCACCTAAAACTGCCGGTACCGCCCCAACTGCAGGAAACTATTCAGGAGTAGTA
TCTCTTGTAATGACTTTGGGAGCCGATGGTTACAGATTAGCAGGTTTCCCACCGGATCACCAGGCATGGAGAGAA
GAACCCTGGATTCATCATGCACCACAAGGTTGTGGAAATTCATCAGGAGGGCCGGTCGACATGAATAGTAGCAAT
TACTGCTGTGAATTGTGTTGTAGCCCTGCTTGTACCGGGTGCTATACAATTACAGGTGATACTTGTAATGAGGAG
ACCCAGAATCTGAGCACAATATATGCCAGGAAATATCAATCAAAAGTTAAGAGGCAGATATTTTCAGACTATCAG
TCAGAGGTTGACATATATAACAGAATTCGGAATGAATTAGGGCCGGGGCCCGCTCCCCAGTCTATTACAGAACTA
TGTTCGGAATATCGCAACACACAAATATATACGATAAATGACAAGATACTATCATATACGGAATCGATGGCAGGC
AAAAGAGAAATGGTTATCATTACATTTAAGAGCGGCGCAACATTTCAGGTCGAAGTCCCGGGCAGTCAACATATA
GACTCCCAAAAAAAAGCCATTGAAAGGATGAAGGACACATTAAGAATCACATATCTGACCGAGACCAAAATTGAT
AAATTATGTGTATGGAATAATAAAACCCCCAATTCAATTGCGGCAATCAGTGATCCCCGGGTACCGAGCTCGATG
AATAGTAGCAATTACTGCTGTGAATTGTGTTGTAGCCCTGCTTGTACCGGGTGCTATTAATAACGGCCGCACTCG
AGCACCACCACCACCACCACTGAGATCCGGCTGCTAACAAAGCCCGAANN (SEQ ID NO: 41)

FIG. 17A 9419 sequence with denotations:

ATGGCTAGCATGAATAGTAGCAATTACTGCTGTGAATTGTGTTGTAGCCCTGCTTGTACCGGGTGCTATGGGCCG
GGGCCC
   NheI  STa$_{N12S}$               LINKER
AATGGCGACAAATTATACCGTGCTGACTCTAGACCCCAGATGAAATAAAACGTTCCGGAGGTCTTATGCCCAGA
GGGCAT
LT-A1(1-30)
AATGAGTACATGGCTAGCGCAGTAGAGGATTTTTTCATTGTTCCAGTTTCTGGAGATCCTGCAATTGATCTTTTG
CAAGCT
    CFA MEFA
GATGGCAATGCTCTGCCATCAGCTGTAAAGTTAGCTTATTCTCCCGCATCAAAAACTAATACTTTGGTGGGTGTT
TTGACT
CTTGTACATACAAACGATGCAACTAAAAAAAATGTACTAGTTAAGCTTGTAACACCACAGCTTACAGATGTTCTG
AATCCAACCCTGCAAATTCCTGTTTCTGTGCAGGTAACGGTCTACCCTGTTTCTACAACAGCCAAAGAATTTGAA
GCTGCTGCTTTGGGATATTCTGCATCCGGTGTAAATGGCTTGGTGTCAATTGTGCTTACTGTAATTAGCGCTGCA
CCTAAAACTGCCGGTACCGCCCCAACTGCAGGAAACTATTCAGGAGTAGTATCTCTTGTAATGACTTTGGGAGCC
GATGGTTACAGATTAGCAGGTTTCCCACCGGATCACCAGGCATGGAGAGAAGAACCCTGGATTCATCATGCACCA
CAAGGTTGTGGAAATTCATCAGGAGGGCCG
   LT-A1(160-192)                      R192G
GTCGACATGAATAGTAGCAATTACTGCTGTGAATTGTGTTGTAGCCCTGCTTGTACCGGGTGCTATACAATTACA
GGTGAT
LINKER     STa$_{N12S}$                 LT-A2(193-240)
ACTTGTAATGAGGAGACCCAGAATCTGAGCACAATATATGCCAGGAAATATCAATCAAAAGTTAAGAGGCAGATA
TTTTCAGACTATCAGTCAGAGGTTGACATATATAACAGAATTCGGAATGAATTAGGGCCGGGGCCCGCTCCCCAG
TCTATTACAGAA
                       LINKER    LT-B(1-100)
CTATGTTCGGAATATCGCAACACACAAATATATACGATAAATGACAAGATACTATCATATACGGAATCGATGGCA
GGCAAAAGAGAAATGGTTATCATTACATTTAAGAGCGGCGCAACATTTCAGGTCGAAGTCCCGGGCAGTCAACAT
ATAGACTCCCAAAAAAAAGCCATTGAAAGGATGAAGGACACATTAAGAATCACATATCTGACCGAGACCAAAATT
GATAAATTATGTGTATGGAATAATAAAACCCCCAATTCAATTGCGGCAATCAGTGATCCCCGGGTACCGAGCTCG
ATGAATAGTAGCAATTACTGCTGT
                      LINKER        STa$_{N12S}$
GAATTGTGTTGTAGCCCTGCTTGTACCGGGTGCTATTAATAACGGCCGCACTCGAGCACCACCACCACCACCACT
GAGATCCGGCTGCTA        STOP   EagI
(SEQ ID NO: 40)

FIG. 17B

MASMNSSNYCCELCCSPACTGCYGPGPNGDKLYRADSRPPD
EIKRSGGLMPRGHNEYMASAVEDFFIVPVSGDPAIDLLQAD
GNALPSAVKLAYSPASKTNTLVGVLTLVHTNDATKKNVLVK
LVTPQLTDVLNPTLQIPVSVQVTVYPVSTTAKEFEAAALGYS
ASGVNGLVSIVLTVISAAPKTAGTAPTAGNYSGVVSLVMTL
GADGYRLAGFPPDHQAWREEPWIHHAPQGCGNSSGGPVDM
NSSNYCCELCCSPACTGCYTITGDTCNEETQNLSTIYARKYQ
SKVKRQIFSDYQSEVDIYNRIRNELGPGPAPQSITELCSEYRN
TQIYTINDKILSYTESMAGKREMVIITFKSGATFQVEVPGSQ
HIDSQKKAIERMKDTLRITYLTETKIDKLCVWNNKTPNSIAA
ISDPRVPSSMNSSNYCCELCCSPACTGCY Stop Stop RPHSSTTT
TTTEIRLLTKPEX (SEQ ID NO: 42)

Note: Red = STa$_{N12S}$; Yellow = CfaB with Blue CS epitopes; Green = LT; Grey = linker.

1 MASMNSSNYC CELCCSPACT GCYGPGPNGD KLYRADSRPP DEIKRSGGLM PRGHNEYMAS
61 AVEDFFIVPV SGDPAIDLLQ ADGNALPSAV KLAYSPASKT NTLVGVLTLV HTNDATKKNV
121 LVKLVTPQLT DVLNPTLQIP VSVQVTVYPV STTAKEFEAA ALGYSASGVN GLVSIVLTVI
181 SAAPKTAGTA PTAGNYSGVV SLVMTLGADG YRLAGFPPDH QAWREEPWIH HAPQGCGNSS
241 GGPVDMNSSN YCCELCCSPA CTGCYTITGD TCNEETQNLS TIYARKYQSK VKRQIFSDYQ
301 SEVDIYNRIR NELGPGPAPQ SITELCSEYR NTQIYTINDK ILSYTESMAG KREMVIITFK
361 SGATFQVEVP GSQHIDSQKK AIERMKDTLR ITYLTETKID KLCVWNNKTP NSIAAISDPR
421 VPSSMNSSNY CCELCCSPAC TGCY (SEQ ID NO: 42)

FIG. 17C

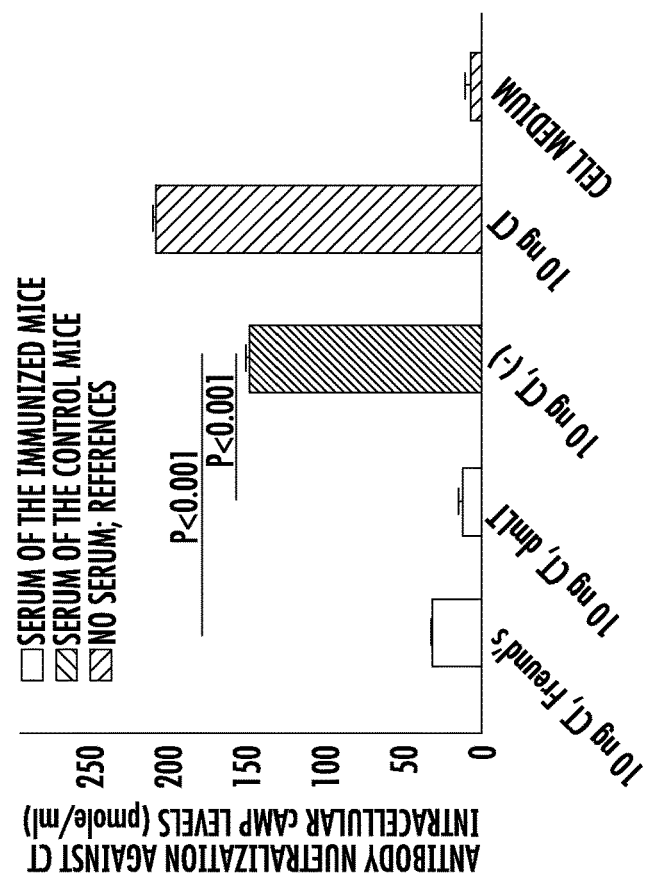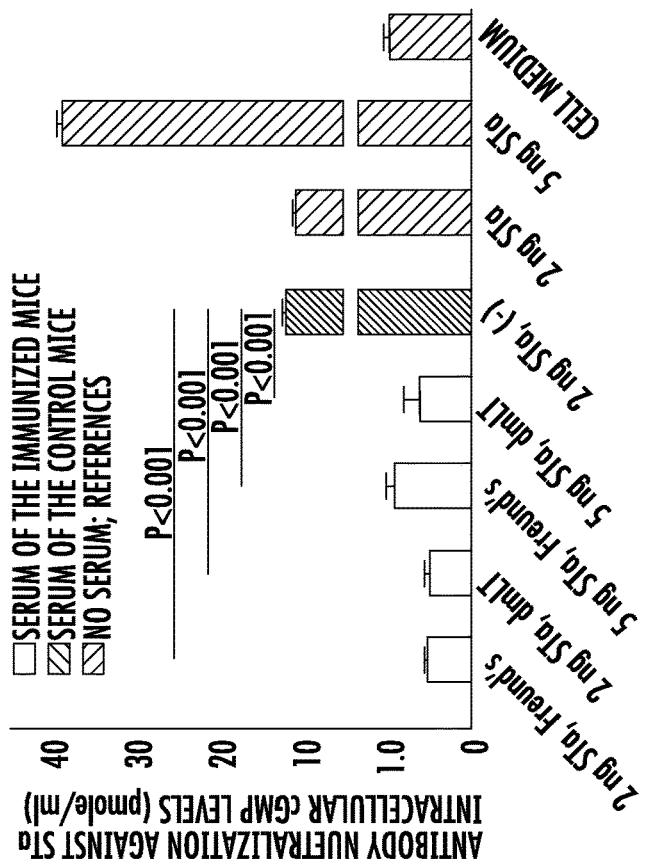
FIG. 20

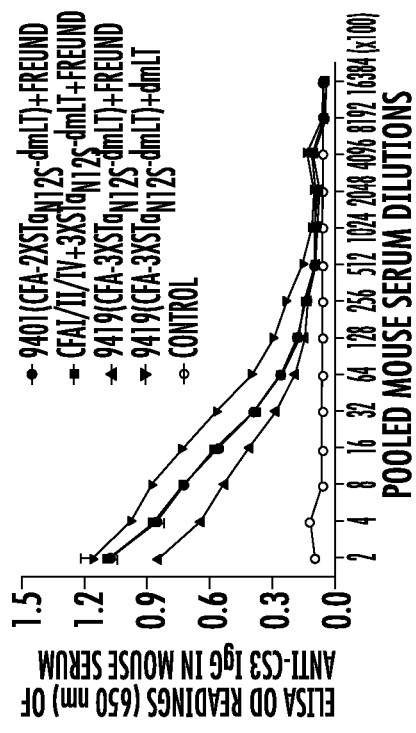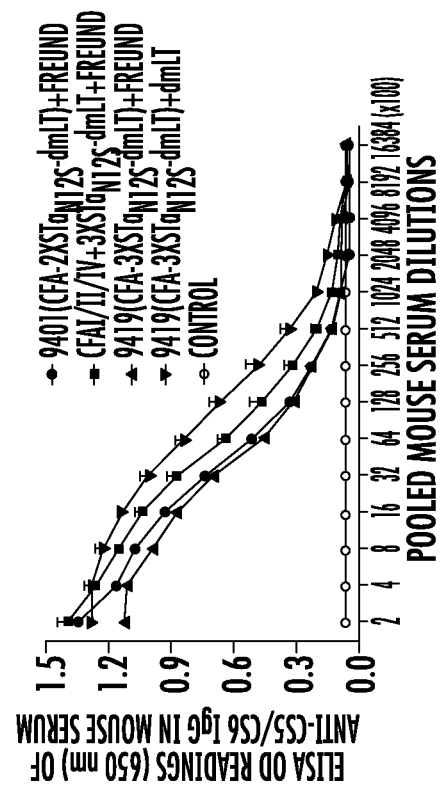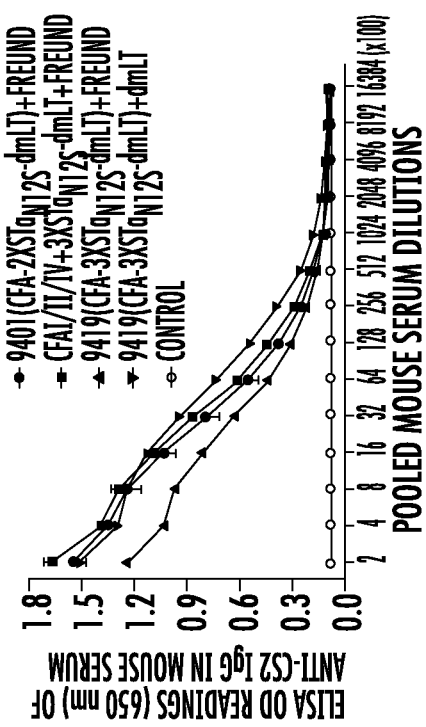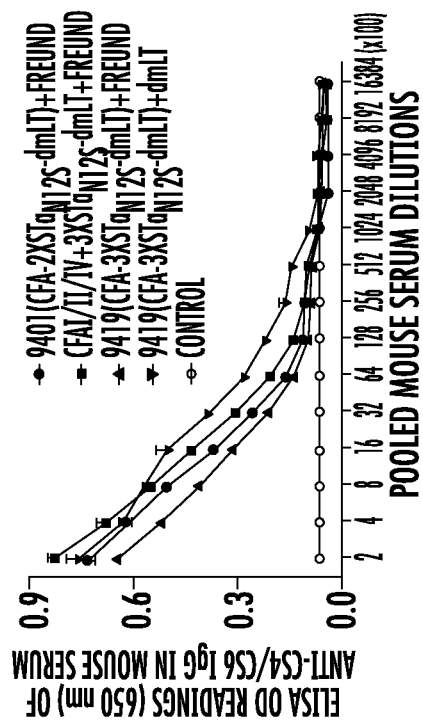

SEQUENCE LISTING

```
<160> NUMBER OF SEQ ID NOS: 42

<210> SEQ ID NO 1
<211> LENGTH: 171
<212> TYPE: PRT
<213> ORGANISM: Artificial Sequence
<220> FEATURE:
<223> OTHER INFORMATION: synthetic sequence

<400> SEQUENCE: 1

Met Gly Ser Ser His His His His His His Ser Ser Gly Leu Val Pro
1               5                   10                  15

Arg Gly Ser His Met Ala Ser Ala Val Glu Asp Phe Phe Ile Val Pro
                20                  25                  30

Val Ser Gly Asp Pro Ala Ile Asp Leu Leu Gln Ala Asp Gly Asn Ala
            35                  40                  45

Leu Pro Ser Ala Val Lys Leu Ala Tyr Ser Pro Ala Ser Lys Thr Asn
    50                  55                  60

Thr Leu Val Gly Val Leu Thr Leu Val His Thr Asn Asp Ala Thr Lys
65                  70                  75                  80

Lys Asn Val Leu Val Lys Leu Val Thr Pro Gln Leu Thr Asp Val Leu
                85                  90                  95

Asn Pro Thr Leu Gln Ile Pro Val Ser Val Gln Val Thr Val Tyr Pro
                100                 105                 110

Val Ser Thr Thr Ala Lys Glu Phe Glu Ala Ala Ala Leu Gly Tyr Ser
            115                 120                 125
```

```
Ala Ser Gly Val Asn Gly Leu Val Ser Ile Val Leu Thr Val Ile Ser
    130                 135                 140

Ala Ala Pro Lys Thr Ala Gly Thr Ala Pro Thr Ala Gly Asn Tyr Ser
145                 150                 155                 160

Gly Val Val Ser Leu Val Met Thr Leu Gly Ala
                165                 170

<210> SEQ ID NO 2
<211> LENGTH: 435
<212> TYPE: PRT
<213> ORGANISM: Artificial Sequence
<220> FEATURE:
<223> OTHER INFORMATION: synthetic sequence

<400> SEQUENCE: 2

Met Gly Ser Ser His His His His His His Ser Ser Gly Leu Val Pro
1               5                   10                  15

Arg Gly Ser His Met Ala Ser Ala Val Glu Asp Phe Phe Ile Val Pro
                20                  25                  30

Val Ser Gly Asp Pro Ala Ile Asp Leu Leu Gln Ala Asp Gly Asn Ala
            35                  40                  45

Leu Pro Ser Ala Val Lys Leu Ala Tyr Ser Pro Ala Ser Lys Thr Asn
    50                  55                  60

Thr Leu Val Gly Val Leu Thr Leu Val His Thr Asn Asp Ala Thr Lys
65                  70                  75                  80

Lys Asn Val Leu Val Lys Leu Val Thr Pro Gln Leu Thr Asp Val Leu
                85                  90                  95

Asn Pro Thr Leu Gln Ile Pro Val Ser Val Gln Val Thr Val Tyr Pro
            100                 105                 110

Val Ser Thr Thr Ala Lys Glu Phe Glu Ala Ala Leu Gly Tyr Ser
    115                 120                 125

Ala Ser Gly Val Asn Gly Leu Val Ser Ile Val Leu Thr Val Ile Ser
    130                 135                 140

Ala Ala Pro Lys Thr Ala Gly Thr Ala Pro Thr Ala Gly Asn Tyr Ser
145                 150                 155                 160

Gly Val Val Ser Leu Val Met Thr Leu Gly Ala Phe Gly Val Ile Asp
                165                 170                 175

Glu Arg Leu His Arg Asn Arg Glu Tyr Arg Asp Arg Tyr Tyr Arg Asn
            180                 185                 190

Leu Asn Ile Ala Pro Ala Glu Asp Gly Tyr Arg Leu Ala Gly Phe Pro
    195                 200                 205

Pro Asp His Gln Ala Trp Arg Glu Glu Pro Trp Ile His His Ala Pro
210                 215                 220

Gln Gly Cys Gly Asn Ser Ser Gly Gly Pro Val Asp Met Asn Ser Ser
225                 230                 235                 240

Asn Tyr Cys Cys Glu Leu Cys Cys Asn Pro Gln Cys Thr Gly Cys Tyr
            245                 250                 255

Thr Ile Thr Gly Asp Thr Cys Asn Glu Glu Thr Gln Asn Leu Ser Thr
            260                 265                 270

Ile Tyr Leu Arg Lys Tyr Gln Ser Lys Val Lys Arg Gln Ile Phe Ser
    275                 280                 285

Asp Tyr Gln Ser Glu Val Asp Ile Tyr Asn Arg Ile Arg Asn Glu Leu
    290                 295                 300

Gly Pro Gly Pro Ala Pro Gln Ser Ile Thr Glu Leu Cys Ser Glu Tyr
305                 310                 315                 320
```

```
Arg Asn Thr Gln Ile Tyr Thr Ile Asn Asp Lys Ile Leu Ser Tyr Thr
                325                 330                 335

Glu Ser Met Ala Gly Lys Arg Glu Met Val Ile Ile Thr Phe Lys Ser
            340                 345                 350

Gly Ala Thr Phe Gln Val Glu Val Pro Gly Ser Gln His Ile Asp Ser
            355                 360                 365

Gln Lys Lys Ala Ile Glu Arg Met Lys Asp Thr Leu Arg Ile Thr Tyr
        370                 375                 380

Leu Thr Glu Thr Lys Ile Asp Lys Leu Cys Val Trp Asn Asn Lys Thr
385                 390                 395                 400

Pro Asn Ser Ile Ala Ala Ile Ser Asp Pro Arg Val Pro Ser Ser Met
                405                 410                 415

Asn Ser Ser Asn Tyr Cys Cys Glu Leu Cys Cys Asn Pro Gln Cys Thr
            420                 425                 430

Gly Cys Tyr
        435

<210> SEQ ID NO 3
<211> LENGTH: 435
<212> TYPE: PRT
<213> ORGANISM: Artificial Sequence
<220> FEATURE:
<223> OTHER INFORMATION: synthetic sequence

<400> SEQUENCE: 3

Met Gly Ser Ser His His His His His His Ser Ser Gly Leu Val Pro
1               5                   10                  15

Arg Gly Ser His Met Ala Ser Ala Val Glu Asp Phe Phe Ile Val Pro
            20                  25                  30

Val Ser Gly Asp Pro Ala Ile Asp Leu Leu Gln Ala Asp Gly Asn Ala
        35                  40                  45

Leu Pro Ser Ala Val Lys Leu Ala Tyr Ser Pro Ala Ser Lys Thr Asn
    50                  55                  60

Thr Leu Val Gly Val Leu Thr Leu Val His Thr Asn Asp Ala Thr Lys
65                  70                  75                  80

Lys Asn Val Leu Val Lys Leu Val Thr Pro Gln Leu Thr Asp Val Leu
                85                  90                  95

Asn Pro Thr Leu Gln Ile Pro Val Ser Val Gln Val Thr Val Tyr Pro
            100                 105                 110

Val Ser Thr Thr Ala Lys Glu Phe Glu Ala Ala Leu Gly Tyr Ser
        115                 120                 125

Ala Ser Gly Val Asn Gly Leu Val Ser Ile Val Leu Thr Val Ile Ser
    130                 135                 140

Ala Ala Pro Lys Thr Ala Gly Thr Ala Pro Thr Ala Gly Asn Tyr Ser
145                 150                 155                 160

Gly Val Val Ser Leu Val Met Thr Leu Gly Ala Phe Gly Val Ile Asp
                165                 170                 175

Glu Arg Leu His Arg Asn Arg Glu Tyr Arg Asp Arg Tyr Arg Asn
            180                 185                 190

Leu Asn Ile Ala Pro Ala Glu Asp Gly Tyr Arg Leu Ala Gly Phe Pro
        195                 200                 205

Pro Asp His Gln Ala Trp Arg Glu Glu Pro Trp Ile His His Ala Pro
    210                 215                 220

Gln Gly Cys Gly Asn Ser Ser Gly Gly Pro Val Asp Met Asn Ser Ser
225                 230                 235                 240
```

```
Asn Tyr Cys Cys Glu Leu Cys Cys Ser Pro Ala Cys Thr Gly Cys Tyr
            245                 250                 255

Thr Ile Thr Gly Asp Thr Cys Asn Glu Glu Thr Gln Asn Leu Ser Thr
        260                 265                 270

Ile Tyr Leu Arg Lys Tyr Gln Ser Lys Val Lys Arg Gln Ile Phe Ser
        275                 280                 285

Asp Tyr Gln Ser Glu Val Asp Ile Tyr Asn Arg Ile Arg Asn Glu Leu
        290                 295                 300

Gly Pro Gly Pro Ala Pro Gln Ser Ile Thr Glu Leu Cys Ser Glu Tyr
305                 310                 315                 320

Arg Asn Thr Gln Ile Tyr Thr Ile Asn Asp Lys Ile Leu Ser Tyr Thr
                325                 330                 335

Glu Ser Met Ala Gly Lys Arg Glu Met Val Ile Ile Thr Phe Lys Ser
            340                 345                 350

Gly Ala Thr Phe Gln Val Glu Val Pro Gly Ser Gln His Ile Asp Ser
        355                 360                 365

Gln Lys Lys Ala Ile Glu Arg Met Lys Asp Thr Leu Arg Ile Thr Tyr
        370                 375                 380

Leu Thr Glu Thr Lys Ile Asp Lys Leu Cys Val Trp Asn Asn Lys Thr
385                 390                 395                 400

Pro Asn Ser Ile Ala Ala Ile Ser Asp Pro Arg Val Pro Ser Ser Met
                405                 410                 415

Asn Ser Ser Asn Tyr Cys Cys Glu Leu Cys Cys Ser Pro Ala Cys Thr
                420                 425                 430

Gly Cys Tyr
        435

<210> SEQ ID NO 4
<211> LENGTH: 9
<212> TYPE: PRT
<213> ORGANISM: Artificial Sequence
<220> FEATURE:
<223> OTHER INFORMATION: synthetic sequence

<400> SEQUENCE: 4

Ser Gly Val Val Ser Leu Val Met Thr
1               5

<210> SEQ ID NO 5
<211> LENGTH: 8
<212> TYPE: PRT
<213> ORGANISM: Artificial Sequence
<220> FEATURE:
<223> OTHER INFORMATION: synthetic sequence

<400> SEQUENCE: 5

Pro Thr Leu Gln Ile Pro Val Ser
1               5

<210> SEQ ID NO 6
<211> LENGTH: 7
<212> TYPE: PRT
<213> ORGANISM: Artificial Sequence
<220> FEATURE:
<223> OTHER INFORMATION: synthetic sequence

<400> SEQUENCE: 6

Leu Val Ser Ile Val Leu Thr
1               5
```

```
<210> SEQ ID NO 7
<211> LENGTH: 9
<212> TYPE: PRT
<213> ORGANISM: Artificial Sequence
<220> FEATURE:
<223> OTHER INFORMATION: synthetic sequence

<400> SEQUENCE: 7

Asn Thr Leu Val Gly Val Leu Thr Leu
1               5

<210> SEQ ID NO 8
<211> LENGTH: 8
<212> TYPE: PRT
<213> ORGANISM: Artificial Sequence
<220> FEATURE:
<223> OTHER INFORMATION: synthetic sequence

<400> SEQUENCE: 8

Lys Asn Val Leu Val Lys Leu Val
1               5

<210> SEQ ID NO 9
<211> LENGTH: 9
<212> TYPE: PRT
<213> ORGANISM: Artificial Sequence
<220> FEATURE:
<223> OTHER INFORMATION: synthetic sequence

<400> SEQUENCE: 9

Asp Phe Phe Ile Val Pro Val Ser Gly
1               5

<210> SEQ ID NO 10
<211> LENGTH: 7
<212> TYPE: PRT
<213> ORGANISM: Artificial Sequence
<220> FEATURE:
<223> OTHER INFORMATION: synthetic sequence

<400> SEQUENCE: 10

Gln Val Thr Val Tyr Pro Val
1               5

<210> SEQ ID NO 11
<211> LENGTH: 109
<212> TYPE: PRT
<213> ORGANISM: Artificial Sequence
<220> FEATURE:
<223> OTHER INFORMATION: synthetic sequence

<400> SEQUENCE: 11

Phe Gly Val Ile Asp Glu Arg Leu His Arg Asn Arg Glu Tyr Arg Asp
1               5                   10                  15

Arg Tyr Tyr Arg Asn Leu Asn Ile Ala Pro Ala Glu Asp Gly Tyr Arg
                20                  25                  30

Leu Ala Gly Phe Pro Pro Asp His Gln Ala Trp Arg Glu Pro Trp
            35                  40                  45

Ile His His Ala Pro Gln Gly Cys Gly Asn Ser Ser Gly Thr Ile Thr
        50                  55                  60

Gly Asp Thr Cys Asn Glu Glu Thr Gln Asn Leu Ser Thr Ile Tyr Leu
65                  70                  75                  80

Arg Lys Tyr Gln Ser Lys Val Lys Arg Gln Ile Phe Ser Asp Tyr Gln
                85                  90                  95
```

Ser Glu Val Asp Ile Tyr Asn Arg Ile Arg Asn Glu Leu
            100                 105

<210> SEQ ID NO 12
<211> LENGTH: 100
<212> TYPE: PRT
<213> ORGANISM: Artificial Sequence
<220> FEATURE:
<223> OTHER INFORMATION: synthetic sequence

<400> SEQUENCE: 12

Ala Pro Gln Ser Ile Thr Glu Leu Cys Ser Glu Tyr Arg Asn Thr Gln
1               5                   10                  15

Ile Tyr Thr Ile Asn Asp Lys Ile Leu Ser Tyr Thr Glu Ser Met Ala
            20                  25                  30

Gly Lys Arg Glu Met Val Ile Ile Thr Phe Lys Ser Gly Ala Thr Phe
        35                  40                  45

Gln Val Glu Val Pro Gly Ser Gln His Ile Asp Ser Gln Lys Lys Ala
    50                  55                  60

Ile Glu Arg Met Lys Asp Thr Leu Arg Ile Thr Tyr Leu Thr Glu Thr
65                  70                  75                  80

Lys Ile Asp Lys Leu Cys Val Trp Asn Asn Lys Thr Pro Asn Ser Ile
                85                  90                  95

Ala Ala Ile Ser
            100

<210> SEQ ID NO 13
<211> LENGTH: 20
<212> TYPE: PRT
<213> ORGANISM: Artificial Sequence
<220> FEATURE:
<223> OTHER INFORMATION: synthetic sequence

<400> SEQUENCE: 13

Met Asn Ser Ser Asn Tyr Cys Cys Glu Leu Cys Cys Asn Pro Gln Cys
1               5                   10                  15

Thr Gly Cys Tyr
            20

<210> SEQ ID NO 14
<211> LENGTH: 20
<212> TYPE: PRT
<213> ORGANISM: Artificial Sequence
<220> FEATURE:
<223> OTHER INFORMATION: synthetic sequence

<400> SEQUENCE: 14

Met Asn Ser Ser Asn Tyr Cys Cys Glu Leu Cys Cys Ser Pro Ala Cys
1               5                   10                  15

Thr Gly Cys Tyr
            20

<210> SEQ ID NO 15
<211> LENGTH: 33
<212> TYPE: DNA
<213> ORGANISM: Artificial Sequence
<220> FEATURE:
<223> OTHER INFORMATION: synthetic sequence

<400> SEQUENCE: 15
gtgagtgcta gcgcagtaga ggattttttc att                              33

<210> SEQ ID NO 16
<211> LENGTH: 37
<212> TYPE: DNA
<213> ORGANISM: Artificial Sequence
<220> FEATURE:
<223> OTHER INFORMATION: synthetic sequence

<400> SEQUENCE: 16
ctctcggccg ttatcaggct cccaaagtca ttacaag         37

<210> SEQ ID NO 17
<211> LENGTH: 20
<212> TYPE: DNA
<213> ORGANISM: Artificial Sequence
<220> FEATURE:
<223> OTHER INFORMATION: synthetic sequence

<400> SEQUENCE: 17
taatacgact cactataggg                            20

<210> SEQ ID NO 18
<211> LENGTH: 42
<212> TYPE: DNA
<213> ORGANISM: Artificial Sequence
<220> FEATURE:
<223> OTHER INFORMATION: synthetic sequence

<400> SEQUENCE: 18
accaaaggct cccaaagtca ttacaagaga tactactcct ga   42

<210> SEQ ID NO 19
<211> LENGTH: 48
<212> TYPE: DNA
<213> ORGANISM: Artificial Sequence
<220> FEATURE:
<223> OTHER INFORMATION: synthetic sequence

<400> SEQUENCE: 19
gtaatgactt tgggagcctt tggtgtgatt gatgaacgat tacatcgt    48

<210> SEQ ID NO 20
<211> LENGTH: 21
<212> TYPE: DNA
<213> ORGANISM: Artificial Sequence
<220> FEATURE:
<223> OTHER INFORMATION: synthetic sequence

<400> SEQUENCE: 20
tgctagttat tggtcagggg t                          21

<210> SEQ ID NO 21
<211> LENGTH: 9
<212> TYPE: PRT
<213> ORGANISM: Artificial Sequence
<220> FEATURE:
<223> OTHER INFORMATION: synthetic sequence

<400> SEQUENCE: 21

Lys Asn Ile Thr Val Thr Ala Ser Val
1               5

<210> SEQ ID NO 22
<211> LENGTH: 9
<212> TYPE: PRT
<213> ORGANISM: Artificial Sequence
<220> FEATURE:
<223> OTHER INFORMATION: synthetic sequence

<400> SEQUENCE: 22

Phe Glu Ser Tyr Arg Val Met Thr Gln
1               5

<210> SEQ ID NO 23
<211> LENGTH: 8
<212> TYPE: PRT
<213> ORGANISM: Artificial Sequence
<220> FEATURE:
<223> OTHER INFORMATION: synthetic sequence

<400> SEQUENCE: 23

Lys Val Ile Val Lys Leu Ala Asp
1               5

<210> SEQ ID NO 24
<211> LENGTH: 8
<212> TYPE: PRT
<213> ORGANISM: Artificial Sequence
<220> FEATURE:
<223> OTHER INFORMATION: synthetic sequence

<400> SEQUENCE: 24

Ser Thr Val Gln Met Pro Ile Ser
1               5

<210> SEQ ID NO 25
<211> LENGTH: 7
<212> TYPE: PRT
<213> ORGANISM: Artificial Sequence
<220> FEATURE:
<223> OTHER INFORMATION: synthetic sequence

<400> SEQUENCE: 25

Ser Trp Gly Gly Gln Val Leu
1               5

<210> SEQ ID NO 26
<211> LENGTH: 7
<212> TYPE: PRT
<213> ORGANISM: Artificial Sequence
<220> FEATURE:
<223> OTHER INFORMATION: synthetic sequence

<400> SEQUENCE: 26

Val Ser Ser Ser Gln Glu Leu
1               5

<210> SEQ ID NO 27
<211> LENGTH: 519
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (19)..(19)
<223> OTHER INFORMATION: n is a, c, g, or t

<400> SEQUENCE: 27
atgggcagca gccatcatna tcatcatcac agcagcggcc tggtgccgcg cggcagccat      60
atggctagcg cagtagagga ttttttcatt gttccagttt ctggagatcc tgcaattgat     120
cttttgcaag ctgatggcaa tgctctgcca tcagctgtaa agttagctta ttctcccgca     180
tcaaaaacta atactttggt gggtgttttg actcttgtac atacaaacga tgcaactaaa     240

```
aaaaatgtac tagttaagct tgtaacacca cagcttacag atgttctgaa tccaaccctg      300
caaattcctg tttctgtgca ggtaacggtc taccctgttt ctacaacagc caagaatttt      360
gaagctgctg ctttgggata ttctgcatcc ggtgtaaatg gcttggtgtc aattgtgctt      420
actgtaatta gcgctgcacc taaaactgcc ggtaccgccc caactgcagg aaactattca      480
ggagtagtat ctcttgtaat gactttggga gcctgataa                             519
```

```
<210> SEQ ID NO 28
<211> LENGTH: 1317
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (19)..(19)
<223> OTHER INFORMATION: n is a, c, g, or t

<400> SEQUENCE: 28
atgggcagca gccatcatna tcatcatcac agcagcggcc tggtgccgcg cggcagccat       60
atggctagcg cagtagagga ttttttcatt gttccagttt ctggagatcc tgcaattgat      120
cttttgcaag ctgatggcaa tgctctgcca tcagctgtaa agttagctta ttctcccgca      180
tcaaaaacta atactttggt gggtgttttg actcttgtac atacaaacga tgcaactaaa      240
aaaaatgtac tagttaagct tgtaacacca cagcttacag atgttctgaa tccaaccctg      300
caaattcctg tttctgtgca ggtaacggtc taccctgttt ctacaacagc caagaatttt      360
gaagctgctg ctttgggata ttctgcatcc ggtgtaaatg gcttggtgtc aattgtgctt      420
actgtaatta gcgctgcacc taaaactgcc ggtaccgccc caactgcagg aaactattca      480
ggagtagtat ctcttgtaat gactttggga gcctttggtg tgattgatga acgattacat      540
cgtaacaggg aatatagaga ccggtattac agaaatctga atatagctcc ggcagaggat      600
ggttacagat tagcaggttt cccaccggat caccaagctt ggagagaaga accctggatt      660
catcatgcac cacaaggttg tggaaattca tcagggagggc cggtcgacat gaatagtagc      720
aattactgct gtgaattgtg ttgtaatcct cagtgtaccg ggtgctatac aattacaggt      780
gatacttgta atgaggagac ccagaatctg agcacaatat atctcaggaa atatcaatca      840
aaagttaaga ggcagatatt ttcagactat cagtcagagg ttgacatata taacagaatt      900
cggaatgaat tagggccggg gcccgctccc cagtctatta cagaactatg ttcggaatat      960
cgcaacacac aaatatatac gataaatgac aagatactac catatacgga atcgatggca     1020
ggcaaaagag aaatggttat cattacattt aagagcggcg caacatttca ggtcgaagtc     1080
ccgggcagtc aacatataga ctcccaaaaa aaagccattg aaaggatgaa ggacacatta     1140
agaatcacat atctgaccga gaccaaaatt gataaattat gtgtatggaa taataaaacc     1200
cccaattcaa ttgcggcaat cagtgatccc cgggtaccga gctcgatgaa tagtagcaat     1260
tactgctgtg aattgtgttg taatcctcag tgtaccgggt gctattaata acggccg       1317
```

```
<210> SEQ ID NO 29
<211> LENGTH: 1317
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (19)..(19)
```

<223> OTHER INFORMATION: n is a, c, g, or t

<400> SEQUENCE: 29

| | | | | | |
|---|---|---|---|---|---|
| atgggcagca | gccatcatna | tcatcatcac | agcagcggcc | tggtgccgcg | cggcagccat | 60 |
| atggctagcg | cagtagagga | tttttttcatt | gttccagttt | ctggagatcc | tgcaattgat | 120 |
| cttttgcaag | ctgatggcaa | tgctctgcca | tcagctgtaa | agttagctta | ttctcccgca | 180 |
| tcaaaaacta | atactttggt | gggtgttttg | actcttgtac | atacaaacga | tgcaactaaa | 240 |
| aaaaatgtac | tagttaagct | tgtaacacca | cagcttacag | atgttctgaa | tccaaccctg | 300 |
| caaattcctg | tttctgtgca | ggtaacggtc | taccctgttt | ctacaacagc | caaagaattt | 360 |
| gaagctgctg | ctttgggata | ttctgcatcc | ggtgtaaatg | gcttggtgtc | aattgtgctt | 420 |
| actgtaatta | gcgctgcacc | taaaactgcc | ggtaccgccc | caactgcagg | aaactattca | 480 |
| ggagtagtat | ctcttgtaat | gactttggga | gcctttggtg | tgattgatga | acgattacat | 540 |
| cgtaacaggg | aatatagaga | ccggtattac | agaaatctga | atatagctcc | ggcagaggat | 600 |
| ggttacagat | tagcaggttt | cccaccggat | caccaagctt | ggagagaaga | accctggatt | 660 |
| catcatgcac | acaaggttg | tggaaattca | tcaggagggc | cggtcgacat | gaatagtagc | 720 |
| aattactgct | gtgaattgtg | ttgtagccct | gcttgtaccg | ggtgctatac | aattacaggt | 780 |
| gatacttgta | atgaggagac | ccagaatctg | agcacaatat | atctcaggaa | atatcaatca | 840 |
| aaagttaaga | ggcagatatt | ttcagactat | cagtcagagg | ttgacatata | aacagaatt | 900 |
| cggaatgaat | tagggccggg | gcccgctccc | cagtctatta | cagaactatg | ttcggaatat | 960 |
| cgcaacacac | aaatatatac | gataaatgac | aagatactat | catatacgga | atcgatggca | 1020 |
| ggcaaaagag | aaatggttat | cattacattt | aagagcggcg | caacatttca | ggtcgaagtc | 1080 |
| ccgggcagtc | aacatataga | ctcccaaaaa | aaagccattg | aaaggatgaa | ggacacatta | 1140 |
| agaatcacat | atctgaccga | gaccaaaatt | gataaattat | gtgtatggaa | taataaaacc | 1200 |
| cccaattcaa | ttgcggcaat | cagtgatccc | cgggtaccga | gctcgatgaa | tagtagcaat | 1260 |
| tactgctgtg | aattgtgttg | tagccctgct | tgtaccgggt | gctattaata | acggccg | 1317 |

<210> SEQ ID NO 30
<211> LENGTH: 60
<212> TYPE: DNA
<213> ORGANISM: Artificial Sequence
<220> FEATURE:
<223> OTHER INFORMATION: synthetic sequence

<400> SEQUENCE: 30
atgaatagta gcaattactg ctgtgaattg tgttgtaatc ctcagtgtac cgggtgctat    60

<210> SEQ ID NO 31
<211> LENGTH: 60
<212> TYPE: DNA
<213> ORGANISM: Artificial Sequence
<220> FEATURE:
<223> OTHER INFORMATION: synthetic sequence

<400> SEQUENCE: 31
atgaatagta gcaattactg ctgtgaattg tgttgtagcc ctgcttgtac cgggtgctat    60

<210> SEQ ID NO 32
<211> LENGTH: 24
<212> TYPE: DNA
<213> ORGANISM: Artificial Sequence
<220> FEATURE:
<223> OTHER INFORMATION: synthetic sequence

```
<400> SEQUENCE: 32
gaattgtgtt gtagccctgc ttgt                                              24

<210> SEQ ID NO 33
<211> LENGTH: 24
<212> TYPE: DNA
<213> ORGANISM: Artificial Sequence
<220> FEATURE:
<223> OTHER INFORMATION: synthetic sequence

<400> SEQUENCE: 33
acaagcaggg ctacaacaca attc                                              24

<210> SEQ ID NO 34
<211> LENGTH: 24
<212> TYPE: DNA
<213> ORGANISM: Artificial Sequence
<220> FEATURE:
<223> OTHER INFORMATION: synthetic sequence

<400> SEQUENCE: 34
tgttgtaatc ctcagtgtac cggg                                              24

<210> SEQ ID NO 35
<211> LENGTH: 22
<212> TYPE: DNA
<213> ORGANISM: Artificial Sequence
<220> FEATURE:
<223> OTHER INFORMATION: synthetic sequence

<400> SEQUENCE: 35
cccggtacac tgaggattac aa                                                22

<210> SEQ ID NO 36
<211> LENGTH: 4
<212> TYPE: PRT
<213> ORGANISM: Artificial Sequence
<220> FEATURE:
<223> OTHER INFORMATION: synthetic sequence

<400> SEQUENCE: 36

Gly Pro Val Asp
1

<210> SEQ ID NO 37
<211> LENGTH: 4
<212> TYPE: PRT
<213> ORGANISM: Artificial Sequence
<220> FEATURE:
<223> OTHER INFORMATION: synthetic sequence

<400> SEQUENCE: 37

Gly Pro Gly Pro
1

<210> SEQ ID NO 38
<211> LENGTH: 5
<212> TYPE: PRT
<213> ORGANISM: Artificial Sequence
<220> FEATURE:
<223> OTHER INFORMATION: synthetic sequence

<400> SEQUENCE: 38

Gly Gly Pro Val Asp
1               5
```

<210> SEQ ID NO 39
<211> LENGTH: 7
<212> TYPE: PRT
<213> ORGANISM: Artificial Sequence
<220> FEATURE:
<223> OTHER INFORMATION: synthetic sequence

<400> SEQUENCE: 39

Asp Pro Arg Val Pro Ser Ser
1               5

<210> SEQ ID NO 40
<211> LENGTH: 1222
<212> TYPE: DNA
<213> ORGANISM: Artificial Sequence
<220> FEATURE:
<223> OTHER INFORMATION: synthetic sequence

<400> SEQUENCE: 40

```
atggctagca tgaatagtag caattactgc tgtgaattgt gttgtagccc tgcttgtacc      60
gggtgctatg ggccggggcc caatggcgac aaattatacc gtgctgactc tagaccccca     120
gatgaaataa aacgttccgg aggtcttatg cccagagggc ataatgagta catggctagc     180
gcagtagagg atttttttcat tgttccagtt tctggagatc ctgcaattga tcttttgcaa    240
gctgatggca atgctctgcc atcagctgta aagttagctt attctcccgc atcaaaaact    300
aatactttgg tgggtgtttt gactcttgta catacaaacg atgcaactaa aaaaaatgta    360
ctagttaagc ttgtaacacc acagcttaca gatgttctga atccaaccct gcaaattcct    420
gtttctgtgc aggtaacggt ctaccctgtt tctacaacag ccaaagaatt tgaagctgct    480
gctttgggat attctgcatc cggtgtaaat ggcttggtgt caattgtgct tactgtaatt    540
agcgctgcac ctaaaactgc cggtaccgcc ccaactgcag aaactattc aggagtagta     600 tctcttgtaa tgactttggg agccgatggt tacagattag caggtttccc accggatcac    660
caggcatgga gagaagaacc ctggattcat catgcaccac aaggttgtgg aaattcatca    720
ggagggccgg tcgacatgaa tagtagcaat tactgctgtg aattgtgttg tagccctgct    780
tgtaccgggt gctatacaat tacaggtgat atgttcggaa tatcgcaaca cacaaatata    840
tacgataaat gacaagatac tatcatatac ggaatcgatg gcaggcaaaa gagaaatggt    900
tatcattaca tttaagagcg gcgcaacatt tcaggtcgaa gtcccgggca gtcaacatat    960
agactcccaa aaaaaagcca ttgaaaggat gaaggacaca ttaagaatca catatctgac   1020
cgagaccaaa attgataaat tatgtgtatg gaataataaa accccccaatt caattgcggc   1080 aatcagtgat ccccgggtac cgagctcgat gaatagtagc aattactgct gtgaattgtg   1140
ttgtagccct gcttgtaccg ggtgctatta taacggccg cactcgagca ccaccaccac    1200
caccactgag atccggctgc ta                                            1222
```

<210> SEQ ID NO 41
<211> LENGTH: 1770
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: misc_feature
<222> LOCATION: (1769)..(1770)
<223> OTHER INFORMATION: n is a, c, g, or t

<400> SEQUENCE: 41

```
nngcattagg aagcagccca gtagtaggtt gaggccgttg agcaccgccg ccgcaaggaa      60
tggtgcatgc aaggagatgg cgcccaacag tcccccggcc acggggcctg ccaccatacc     120
cacgccgaaa caagcgctca tgagcccgaa gtggcgagcc cgatcttccc catcggtgat     180
gtcggcgata taggcgccag caaccgcacc tgtggcgccg gtgatgccgg ccacgatgcg     240
tccggcgtag aggatcgaga tctcgatccc gcgaaattaa tacgactcac tataggggaa     300
ttgtgagcgg ataacaattc ccctctagaa ataattttgt ttaactttaa gaaggagata     360
taccatggaa atggctagca tgaatagtag caattactgc tgtgaattgt gttgtagccc     420
tgcttgtacc gggtgctatg gccggggcc aatggcgac aaattatacc gtgctgactc     480
tagaccccca gatgaaataa acgttccgg aggtcttatg cccagagggc ataatgagta     540
catggctagc gcagtagagg attttttcat tgttccagtt tctggagatc ctgcaattga     600
tcttttgcaa gctgatggca atgctctgcc atcagctgta aagttagctt attctcccgc     660
atcaaaaact aatactttgg tgggtgtttt gactcttgta catacaaacg atgcaactaa     720
aaaaaatgta ctagttaagc ttgtaacacc acagcttaca gatgttctga atccaaccct     780
gcaaattcct gtttctgtgc aggtaacggt ctaccctgtt tctacaacag ccaagaatt     840
tgaagctgct gctttgggat attctgcatc cggtgtaaat ggcttggtgt caattgtgct     900
tactgtaatt agcgctgcac ctaaaactgc cggtaccgcc ccaactgcag gaaactattc     960
aggagtagta tctcttgtaa tgactttggg agccgatggt tacagattag caggtttccc    1020
accggatcac caggcatgga gagaagaacc ctggattcat catgcaccac aaggttgtgg    1080
aaattcatca ggagggccgg tcgacatgaa tagtagcaat tactgctgtg aattgtgttg    1140
tagccctgct tgtaccgggt gctatacaat tacaggtgat acttgtaatg aggagaccca    1200
gaatctgagc acaatatatg ccaggaaata tcaatcaaaa gttaagaggc agatattttc    1260
agactatcag tcagaggttg acatatataa cagaattcgg aatgaattag gccggggcc    1320
cgctccccag tctattacag aactatgttc ggaatatcgc aacacacaaa tatatacgat    1380
aaatgacaag atactatcat atacggaatc gatggcaggc aaaagagaaa tggttatcat    1440
tacatttaag agcggcgcaa catttcaggt cgaagtcccg ggcagtcaac atatagactc    1500
ccaaaaaaaa gccattgaaa ggatgaagga cacattaaga atcacatatc tgaccgagac    1560
caaaattgat aaattatgtg tatggaataa taaaaccccc aattcaattg cggcaatcag    1620
tgatccccgg gtaccgagct cgatgaatag tagcaattac tgctgtgaat tgtgttgtag    1680
ccctgcttgt accgggtgct attaataacg gccgcactcg agcaccacca ccaccaccac    1740
tgagatccgg ctgctaacaa agcccgaann                                    1770
```

<210> SEQ ID NO 42
<211> LENGTH: 444
<212> TYPE: PRT
<213> ORGANISM: Artificial Sequence
<220> FEATURE:
<223> OTHER INFORMATION: synthetic sequence

<400> SEQUENCE: 42

```
Met Ala Ser Met Asn Ser Ser Asn Tyr Cys Cys Glu Leu Cys Cys Ser
1               5                   10                  15

Pro Ala Cys Thr Gly Cys Tyr Gly Pro Gly Pro Asn Gly Asp Lys Leu
```

-continued

```
                  20                  25                  30
Tyr Arg Ala Asp Ser Arg Pro Pro Asp Glu Ile Lys Arg Ser Gly Gly
                35                  40                  45
Leu Met Pro Arg Gly His Asn Glu Tyr Met Ala Ser Ala Val Glu Asp
            50                  55                  60
Phe Phe Ile Val Pro Val Ser Gly Asp Pro Ala Ile Asp Leu Leu Gln
 65                  70                  75                  80
Ala Asp Gly Asn Ala Leu Pro Ser Ala Val Lys Leu Ala Tyr Ser Pro
                85                  90                  95
Ala Ser Lys Thr Asn Thr Leu Val Gly Val Leu Thr Leu Val His Thr
                100                 105                 110
Asn Asp Ala Thr Lys Lys Asn Val Leu Val Lys Leu Val Thr Pro Gln
                115                 120                 125
Leu Thr Asp Val Leu Asn Pro Thr Leu Gln Ile Pro Val Ser Val Gln
            130                 135                 140
Val Thr Val Tyr Pro Val Ser Thr Thr Ala Lys Glu Phe Glu Ala Ala
145                 150                 155                 160
Ala Leu Gly Tyr Ser Ala Ser Gly Val Asn Gly Leu Val Ser Ile Val
                165                 170                 175
Leu Thr Val Ile Ser Ala Ala Pro Lys Thr Ala Gly Thr Ala Pro Thr
                180                 185                 190
Ala Gly Asn Tyr Ser Gly Val Val Ser Leu Val Met Thr Leu Gly Ala
                195                 200                 205
Asp Gly Tyr Arg Leu Ala Gly Phe Pro Pro Asp His Gln Ala Trp Arg
            210                 215                 220
Glu Glu Pro Trp Ile His His Ala Pro Gln Gly Cys Gly Asn Ser Ser
225                 230                 235                 240
Gly Gly Pro Val Asp Met Asn Ser Ser Asn Tyr Cys Cys Glu Leu Cys
                245                 250                 255
Cys Ser Pro Ala Cys Thr Gly Cys Tyr Thr Ile Thr Gly Asp Thr Cys
                260                 265                 270
Asn Glu Glu Thr Gln Asn Leu Ser Thr Ile Tyr Ala Arg Lys Tyr Gln
                275                 280                 285
Ser Lys Val Lys Arg Gln Ile Phe Ser Asp Tyr Gln Ser Glu Val Asp
                290                 295                 300
Ile Tyr Asn Arg Ile Arg Asn Glu Leu Gly Pro Gly Pro Ala Pro Gln
305                 310                 315                 320
Ser Ile Thr Glu Leu Cys Ser Glu Tyr Arg Asn Thr Gln Ile Tyr Thr
                325                 330                 335
Ile Asn Asp Lys Ile Leu Ser Tyr Thr Glu Ser Met Ala Gly Lys Arg
                340                 345                 350
Glu Met Val Ile Ile Thr Phe Lys Ser Gly Ala Thr Phe Gln Val Glu
                355                 360                 365
Val Pro Gly Ser Gln His Ile Asp Ser Gln Lys Lys Ala Ile Glu Arg
            370                 375                 380
Met Lys Asp Thr Leu Arg Ile Thr Tyr Leu Thr Glu Thr Lys Ile Asp
385                 390                 395                 400
Lys Leu Cys Val Trp Asn Asn Lys Thr Pro Asn Ser Ile Ala Ala Ile
                405                 410                 415
Ser Asp Pro Arg Val Pro Ser Ser Met Asn Ser Ser Asn Tyr Cys Cys
                420                 425                 430
```

```
Glu Leu Cys Cys Ser Pro Ala Cys Thr Gly Cys Tyr
        435                 440
```

MULTIEPITOPE FUSION ANTIGENS AND VACCINES AND THEIR USE IN TREATMENT OF ENTEROTOXIGENIC DIARRHEA

CROSS-REFERENCE TO RELATED APPLICATIONS

This application is a 35 U.S.C. § 371 U.S. national entry of International Application PCT/US2014/070874, having an international filing date of Dec. 17, 2014, which claims the benefit of U.S. Provisional Application No. 61/917,105, filed Dec. 17, 2013, the content of each of the aforementioned applications is herein incorporated by reference in their entirety.

INCORPORATION-BY-REFERENCE OF MATERIAL SUBMITTED ELECTRONICALLY

The instant application contains a Sequence Listing which has been submitted in ASCII format via EFS-Web and is hereby incorporated by reference in its entirety. Said ASCII copy, created on Dec. 12, 2014, is named P12168-02_ST25.txt and is 30,350 bytes in size.

BACKGROUND OF THE INVENTION

Virulence heterogeneity among bacterial or viral strains or isolates remains as one major challenge in vaccine development. Like other infectious pathogens, enterotoxigenic *Escherichia coli* (ETEC) strains are genetically and immunologically heterogeneous. ETEC strains are the most common bacteria causing diarrhea, a disease continues to be the second leading cause of death to children younger than 5 years in developing countries and remains as a major threat to global health. These ETEC strains produce immunologically different colonization factor antigens (CFAs) to colonize host small intestines and enterotoxins to disrupt fluid and electrolyte homeostasis in small intestinal epithelial cells that leads to fluid hyper-secretion and diarrhea. There are 23 CFA or CS (coli surface antigen) adhesins and 2 very distinctive enterotoxins (heat-labile toxin, LT, and heat-stable toxin type Ib, STa) characterized from ETEC strains associated with human diarrhea. As ETEC strains expressing any one or two of these adhesins with either enterotoxin can cause diarrhea, developing vaccines to effectively protect against ETEC diarrhea continues to be challenging.

It has been observed that immunity induced by individual antigens lacked in cross protection against ETEC, clearly due to immunological heterogeneity among CFAs and toxins. Early experimental vaccine studies showed that candidates carrying a single adhesin and/or toxin antigen induced immunity protecting against only ETEC strains expressing the homologous adhesin or toxin. The first ETEC vaccine candidate, killed ETEC prototype strain H10407 (O78:H11, LT+/STa+/CFAI+), induced anti-CFA/I and anti-LT immunity and protected against homologous challenge. Similarly to homologous protection from anti-CFA immunity, anti-LT antitoxin immunity protected against ETEC strains expressing the LT toxin but not against ETEC strains expressing STa toxin. Oral whole-cell ETEC vaccine candidates currently under development include rCTB-CF and ACE527. The rCTB-CF is a killed cocktail product of 5 strains expressing 6 CFA adhesins and recombinant B subunit of cholera toxin (CT) which is a homologue of LT. ACE527 carried 3 live attenuated *E. coli* strains that express 5 CFA adhesins, 1 CFA adhesin subunit, and LTB subunit. The killed rCTB-CF induced antibody responses protecting against 70% ETEC infection or against moderate to severe diarrhea to adults from developed countries travelling to ETEC endemic countries. This product, however, caused adverse effects and provided no significant protection against ETEC diarrhea when given to children especially very young children living in endemic areas, or failed to reduce overall diarrhea incidences among adult travelers. The live attenuated ACE527 initially showed some adverse effects, but these adverse effects were reduced or eliminated when a lower dose was used. ACE527 was shown to induce antibody responses to LTB, CFA/I, CS3, and CS6 among adult volunteers and to protect against severity of diarrhea outcome from homologous challenge.

Although efforts are taken to improve both products, these two candidate products were not optimal in providing satisfactory protection against ETEC diarrhea. Both cocktail products carry no STa antigens to induce antibody response against STa toxin, and require a relatively high dose for oral administration in order to induce host immune responses against each target adhesin and LT toxin. A high administration dose tends to carry excessive somatic antigens, particularly lipopolysaccharide (LPS), which likely cause vomiting among very young vaccine receipients and may mask stimulation of host immune responses specifically to adhesins and toxin. The inability to induce anti-STa antibody response apparently is another cause of lacking in effective protection, as anti-$LT_B$ (or anti-$CT_B$) immunity induced by either product may protect only against strains expressing LT toxin but not against $STa^+$ ETEC strains. $STa^+$ ETEC strains are associated with over two thirds of human ETEC diarrhea cases and moderate to severe ETEC diarrhea cases, and are also a leading cause of diarrhea to children younger than 3 years who live in developing countries. Therefore, ETEC vaccines need also to induce protective anti-STa immunity in order to provide effective protection against ETEC diarrhea.

However, the 19 amino-acid STa is poorly immunogenic and potently toxic; thus itself cannot induce anti-STa immunity, nor could it be a safe antigen even if it were immunogenic.

Therefore, there still exists an unmet need to produce a vaccine which can elicit an immune response and can also induce protective immunity to multiple CFA antigens, as well as anti-LT and anti-STa immunity that would be broadly protective against ETEC.

SUMMARY OF THE INVENTION

In accordance with an embodiment, the present invention provides a multi epitope fusion antigen (MEFA) comprising a polypeptide molecule encoding the colonization factor antigens (CFA) antigens CFA/I, CFA/II (CS1, CS2, CS3), CFA/IV (CS4, CS5, CS6).

In accordance with another embodiment, the present invention provides a MEFA comprising a polypeptide molecule encoding the colonization factor antigens (CFA) antigens CFA/I, CFA/II (CS1, CS2, CS3), CFA/IV (CS4, CS5, CS6), and further comprising one or more enterotoxins, or fragments thereof, covalently linked to the polypeptide molecule.

In accordance with a further embodiment, the present invention provides a MEFA comprising a polypeptide molecule encoding the colonization factor antigens (CFA) antigens CFA/I, CFA/II (CS1, CS2, CS3), CFA/IV (CS4, CS5, CS6), and further comprising heat-labile toxin (LT) and heat-stable toxin (STa).

In accordance with an embodiment, the present invention provides a nucleic acid molecule encoding the polypeptide molecules described herein.

In accordance with another embodiment, the present invention provides an expression vector comprising the nucleic acid molecule encoding the polypeptide molecules described herein.

In accordance with a further embodiment, the present invention provides micro-organism transformed with the expression vector described herein.

In accordance with an embodiment, the present invention provides a vaccine composition comprising the polypeptide molecules described herein, and a pharmaceutically acceptable carrier.

In accordance with another embodiment, the present invention provides a method for the therapy or prophylaxis of Enterotoxigenic *Escherichia coli* (ETEC), infection in a subject comprising administering to the subject the polypeptide molecules or the vaccines described herein.

In accordance with a further embodiment, the present invention provides a method for the therapy or prophylaxis of diarrhea in a subject comprising administering to the subject the polypeptide molecules or the vaccines described herein.

In accordance with still another embodiment, the present invention provides a method for the therapy or prophylaxis of Enterotoxigenic *Escherichia coli* (ETEC), infection in a subject comprising administering to the subject the polypeptide molecules or the vaccines described herein and administration of at least one additional therapeutic agent.

BRIEF DESCRIPTION OF THE DRAWINGS

FIG. 4 shows CFA multiepitope fusion antigen (MEFA) nucleic acid and amino acid sequences of an embodiment of the present invention.

FIG. 5 depicts the construction and detection of the 'CFAI/II/IV-STa$_{toxoid}$-LT$_{toxoid}$' fusion. Panel A: construction of 'CFAI/II/IV-STa$_{toxoid}$-LT$_{toxoid}$' (CFA-toxoid) multi-epitope fusion antigen from a CFA MEFA fusion antigen and toxoid fusion 3xSTa-LT$_{toxoid}$. Replacement of the first 170 amino acids of the 3xSTa$_{414Q}$-tmLT (Zhang et al., Clin Vaccine Immunol., 2014 February; 21(2):243-9) or 3xSTa$_{N12S}$-LT$_{toxoid}$ with a CFA multiepitope fusion antigen yielded CFA-toxoid fusions 'CFA/I/II/IV-STa$_{414Q}$-LT$_{toxoid}$' and 'CFA/I/II/IV-STa$_{N12S}$-LT$_{toxoid}$'. Panel B: Detection of "CFA/I/II/IV-STa$_{414Q}$-dmLT" in Western blot with anti-CFA/I MAb hybriboma supernatant (1:100; provided by Dr. AM Svennerholm), anti-CT serum (1:3300; Sigma), and anti-STa antiserum (1:3300; provided by Dr. DC Robertson). IRDye-labeled goat anti-mouse IgG or anti-rabbit IgG (1:5000; LI-COR, Lincoln, Nebr.) was used as the secondary antibodies.

FIG. 10 shows the nucleic acid sequence of a CFA-toxoid multiepitope fusion antigen (CFA/I/II/IV-STa$_{A14Q}$-LT$_{toxoid}$) gene of an embodiment of the present invention.

FIG. 11 shows the translated amino acid sequence of a CFA-toxoid multiepitope fusion antigen protein (CFA/I/II/IV-STa$_{A14Q}$-LT$_{toxoid}$).

FIG. 12 depicts the amino acid sequence of a CFA-toxoid multiepitope fusion antigen protein (CFA/I/II/IV-STa$_{A14Q}$-LT$_{toxoid}$) having 435 amino acids with a predicted molecular weight of 47.56 kilodaltons.

FIG. 13 shows the nucleic acid sequence of a CFA-toxoid multiepitope fusion antigen (CFA/I/II/IV-STa$_{N12S}$-LT$_{toxoid}$) gene of an embodiment of the present invention.

FIG. 14 shows the translated amino acid sequence of a CFA-toxoid multiepitope fusion antigen protein (CFA/I/II/IV-STa$_{N12S}$-LT$_{toxoid}$).

FIG. 15 depicts the amino acid sequence of a CFA-toxoid multiepitope fusion antigen protein (CFA/I/II/IV-STa$_{N12S}$-LT$_{toxoid}$) having 435 amino acids with a predicted molecular weight of 47.56 kilodaltons.

FIGS. 17A-17C show nucleic acid sequences of a modification of the CFA-STa$_{N12S}$-LT$_{toxoid}$MEFA of the present invention. This embodiment comprises 3 copies of the toxoid STa$_{n12S}$ in order to further enhance the fusion antigen anti-STa immunogenicity.

FIG. 20 is a pair of bar graphs showing that induced anti-STa antibodies in mouse serum can completely neutralize STa toxin.

FIGS. 21A-21H are graphs depicting the double mutant LT (LT$_{R192G/L211A}$; gift from PATH) was found an effective adjuvant to enhance the his-tag-less CFA-3xSTa$_{N12S\text{-}LTtoxoid}$MEFA in inducing antibody responses to all 7 adhesins and both toxins.

DETAILED DESCRIPTION OF THE INVENTION

Figure 1:
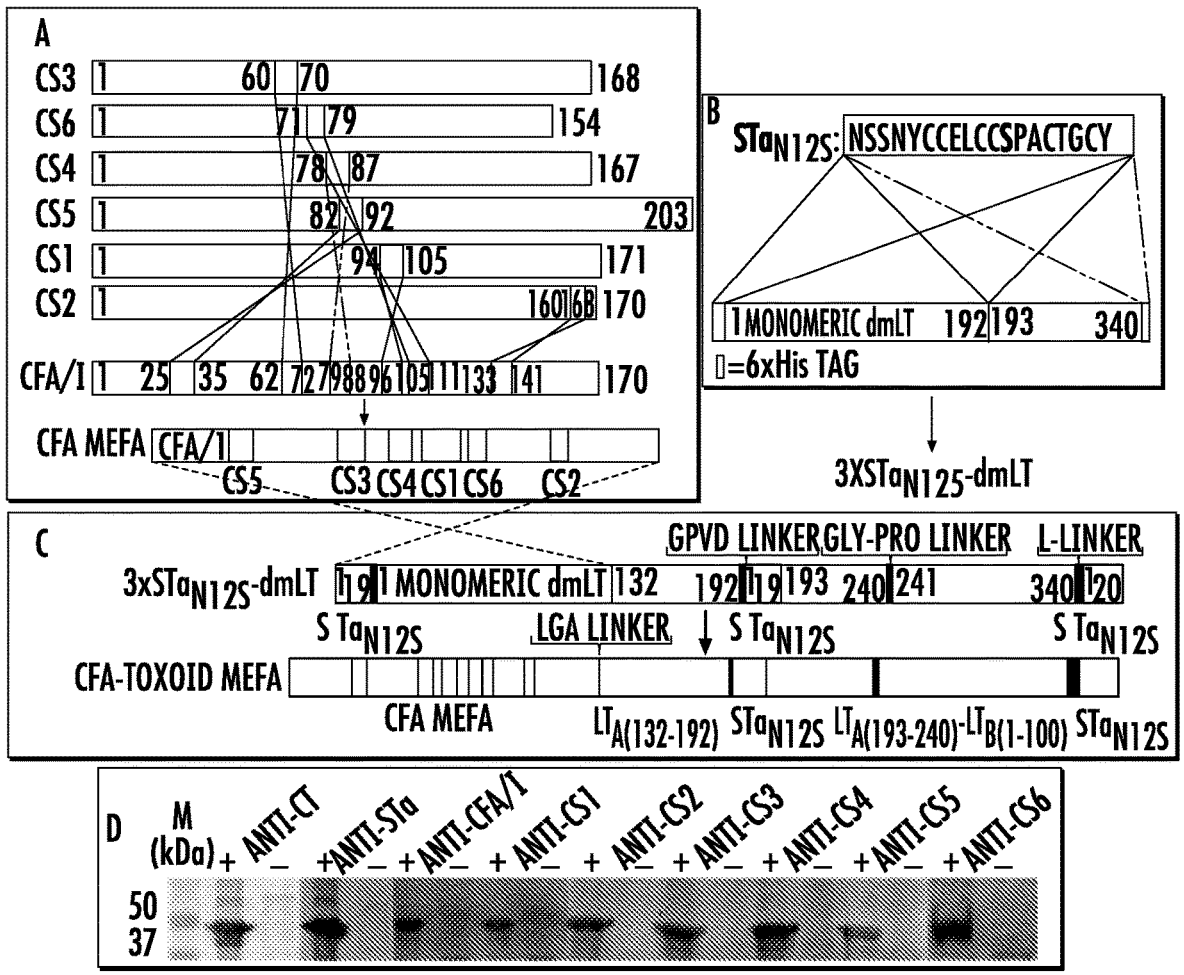
FIGS. 1A-1D. Construction and detection of an embodiment of the invention comprising 'CFAI/II/IV-STa$_{toxoid}$-LT$_{toxoid}$' MEFA. (A) Construction of the CFAI/II/IV MEFA. The most antigenic epitopes of the CS1, CS2, CS3, CS4, CS5 and CS6 major structural subunits were embedded into CFA/I major subunit by replacing the CfaB surface-exposed but less antigenic epitopes. (B) Construction of the 3xSTa$_{N12S}$-LT$_{toxoid}$ fusion. Three copies of the STa$_{toxoid}$ STa$_{N12S}$ gene were genetically fused to the monomeric LT$_{toxoid}$ (LT$_{R192G/L211A}$) gene using SOE (splicing overlap extension) PCRs. (C) Construction of CFA-toxoid MEFA. A substitution of the first 150 amino acids of the 3xSTa$_{N12S}$-LT$_{toxoid}$ (the N-terminal STa$_{N12S}$ and the first 131 amino acids of LT$_A$ subunit) with the CFA/I/II/IV MEFA created the CFA/I/IFIV-STa$_{N12S}$-dmLT MEFA. Four linkers: LGA, GPVD (SEQ ID NO: 36), Gly-Pro linker GPGP (SEQ ID NO: 37), and L-linker (DPRVLSS, SEQ ID NO: 39) were used for the construction. (D) Western blot to detect the CFAXII/IV-STa$_{N12S}$-LT$_{toxoid}$ MEFA protein with anti-CFA/I, anti-CS1, -CS2, -CS3, -CS4, -CS5, and anti-CS6 MAb hybridoma supernatant (1:100; provided by Dr. AM Svennerholm), and rabbit anti-CT (1:3300; Sigma) and anti-STa antiserum (1:3300; provided by Dr. DC Robertson). Extracted MEFA proteins separated in 12% PAGE gel were detected with each anti-adhesin MAb, anti-CT and anti-STa antiserum and IRDye-labeled goat anti-mouse IgG or anti-rabbit IgG (1:5000; LI-COR). Lane (+) indicated the CFA/I/II/IV-STa$_{N12S}$-LT$_{toxoid}$ MEFA proteins, whereas lane (−) of extracted total proteins of *E. coli* BL21 host strain as the negative control. Lane M is the protein marker (in kilodaltons; Precision Plus Protein pre-stained standards; Bio-Rad).

In accordance with one or more embodiments of the present invention, instead of randomly stacking individual epitopes from each adhesin with linkers to generate a multiepitope antigen, the CFA/I major subunit was used CfaB as the backbone, and antigenic prediction software was applied to embed epitopes of CS1-CS6 (by substituting surface-exposed but less antigenic CfaB epitopes) so that the resultant multiepitope CFA protein would have antigenicity propensity similar to the CfaB subunit. This multiepitope CFA protein thereby has a relatively stable structure and a better presentation for the CS1-CS6 epitopes to induce host immune responses. When carried by the CFA/I Cfa operon, this multiepitope CFA protein can be expressed as a multi-epitope CFA adhesin to be used for killed or live whole-cell vaccine development. This approach, described herein as an embodiment of the present invention, to construct multi-epitope antigen against multiple virulence factors can be generally applied in developing multivalent vaccines against pathogens expressing heterogeneous virulence factors.

Data from the embodiments of the present invention indicate that these constructed multiepitope CFA antigens elicited antibodies cross reactive to CAF/I, CFA/II and CFA/IV adhesins, and that anti-adhesin antibodies in the serum significantly inhibited adherence of ETEC or *E. coli* strains expressing these 7 adhesins to Caco-2 or T-84 cells, and shows its application in developing effective ETEC anti-adhesin vaccines. In conjunction to a toxoid fusion antigen that induces antibodies neutralizing against both LT and STa toxins, this multiepitope CFA antigens of the present invention can be used to develop broadly protective vaccines against ETEC diarrhea.

In accordance with an embodiment, the present invention provides a polypeptide molecule comprising one or more of the colonization factor antigens (CFA) antigens CFA/I, CFA/II (CS1, CS2, CS3), CFA/IV (CS4, CS5, CS6).

In accordance with another embodiment, the present invention provides a polypeptide molecule comprising one or more of the colonization factor antigens (CFA) antigens CFA/I, CFA/II (CS1, CS2, CS3), CFA/IV (CS4, CS5, CS6) comprising the amino acid sequence of SEQ ID NO: 1, or having at least 90% identity to SEQ ID NO: 1.

As used herein the polypeptide antigens used in the fusion molecule of the present invention comprise antigenic epitopes of CFA/I ($^{159}$SGVVSLVMT$^{167}$, SEQ ID NO: 4); CS1 ($^{97}$PTLQIPVS$^{164}$, SEQ ID NO: 5); CS2 ($^{161}$LVSIVLT$^{167}$, SEQ ID NO: 6); CS3 ($^{61}$NTLVGVLTL$^{69}$, SEQ ID NO: 7); CS4 ($^{79}$KNVLVKLV$^{86}$, SEQ ID NO: 8); CS5 ($^{83}$DFFIVPVSG$^{91}$, SEQ ID NO: 9); and CS6 ($^{72}$QVTVYPV$^{78}$, SEQ ID NO: 10).

In accordance with another embodiment, a multiepitope CFA subunit gene was genetically fused to a STa-LT$_{toxoid}$ fusion gene (which consists of a unique single open reading frame to coding a single peptide, as the LT genes were modified for disruption of the cistron gene structure and removal of signal peptides) for expression of two CFA-toxoid multiepitope fusion antigens (CFA/I/II/IV-STa$_{A14Q}$-LT$_{toxoid}$ & CFA/I/II/IV-STa$_{N12S}$-LT$_{toxoid}$). The constructed 'CFA/I/II/IV-STa$_{toxoid}$-LT$_{toxoid}$' fusions were examined for antigen safety and immunogenicity in a murine model. Elicited antibodies for neutralization activities were then measured to assess potency of fusion proteins in developing broadly protective vaccines against ETEC strains. Additionally, immune responses were comparatively examined in mice immunized with CFA/I/II/IV-STa$_{toxoid}$-LT$_{toxoid}$ fusion with those in mice co-administrated with the CFA multi-epitope fusion antigen and a STa$_{toxoid}$-LT$_{toxoid}$ fusion in order to further assess application of fusion antigens in multivalent vaccine development.

In accordance with an embodiment, the present invention provides a MEFA comprising a polypeptide molecule encoding the colonization factor antigens (CFA) antigens CFA/I, CFA/II (CS1, CS2, CS3), CFA/IV (CS4, CS5, CS6) and further comprising heat-labile toxin (LT) and heat-stable toxin (STa).

In accordance with an embodiment, the present invention provides a polypeptide molecule comprising the colonization factor antigens (CFA) antigens CFA/I, CFA/II (CS1, CS2, CS3), CFA/IV (CS4, CS5, CS6) and further comprising heat-labile toxin (LT) and heat-stable toxin (STa).

In accordance with another embodiment, the present invention provides a polypeptide molecule comprising the colonization factor antigens (CFA) antigens CFA/I, CFA/II (CS1, CS2, CS3), CFA/IV (CS4, CS5, CS6) and further comprising heat-labile toxin (LT) and heat-stable toxin (STa) comprising the amino acid sequence of SEQ ID NO: 2 and/or 3.

As used herein the polypeptide antigens used in the fusion molecule of the present invention comprise LTA131-240, (SEQ ID NO: 11); LTB1-100, (SEQ ID NO: 12); STa$_{toxoid}$ with an A14Q mutation (SEQ ID NO: 13), or a N12S mutation (SEQ ID NO: 14).

It will be understood by one of ordinary skill in the art that the antigenic polypeptides or fusion proteins provided herein can include one or more copies of the antigen polypeptide. For example, the fusion polypeptide can comprise 1, 2, 3 or more STa toxoid, LTa, CS or CFA fragments or polypeptides.

It will be understood by one of ordinary skill in the art that the antigenic polypeptides or fusion proteins provided herein can include one or more copies of the following linker peptides LGA, GPVD (SEQ ID NO: 36), Gly-Pro linker GPGP (SEQ ID NO: 37), and L-linker (DPRVLSS, SEQ ID NO: 39).

In accordance with an embodiment, the present invention provides a fusion polypeptide molecule comprising CFA antigens I, II and IV, STa$_{toxoid}$ and LT$_{toxoid}$.

In some embodiments, the present invention provides a fusion polypeptide molecule comprising CFA antigens I, II and IV, STa$_{toxoid}$ and LT$_{toxoid}$ wherein the STa$_{toxoid}$ has an A14Q mutation or a N12S mutation.

In accordance with an embodiment, the present invention provides a polynucleotide encoding a fusion polypeptide molecule comprising CFA antigens I, II and IV, STa$_{toxoid}$ and LT$_{toxoid}$.

In some embodiments, the present invention provides a polynucleotide encoding a fusion polypeptide molecule comprising CFA antigens I, II and IV, STa$_{toxoid}$ and LT$_{toxoid}$ antigens, wherein the STa$_{toxoid}$ has an A14Q mutation or a N12S mutation.

In some embodiments the CFA antigens I, II and IV comprise one or more of CS1, CS2, CS3, CS4, CS5 and CS6 adhesins. In some embodiments, CFA antigens I, II and IV comprise each of CS1, CS2, CS3, CS4, CS5 and CS6 adhesins.

In accordance with an embodiment, the present invention provides a fusion polypeptide molecule comprising three STa$_{toxoid}$ antigens and a LT$_{toxoid}$ antigen.

In some embodiments, the present invention provides a polynucleotide encoding a fusion polypeptide molecule comprising three STa$_{toxoid}$ antigens and a LT$_{toxoid}$ antigen.

In accordance with an embodiment, the present invention provides a fusion polypeptide molecule comprising three STa$_{toxoid}$ antigens and a LT$_{toxoid}$ antigen, wherein the three STa$_{toxoid}$ antigens are selected from the group consisting of STa$_{A14Q}$ and STa$_{N12S}$.

In accordance with an embodiment, the present invention provides a polynucleotide encoding a fusion polypeptide molecule comprising three STa$_{toxoid}$ antigens and a LT$_{toxoid}$ antigen, wherein the three STa$_{toxoid}$ antigens are selected from the group consisting of STa$_{A14Q}$ and STa$_{N12S}$.

In some embodiments, the three STa$_{toxoid}$ antigens are the same.

In accordance with another embodiment, the present invention provides a fusion polypeptide molecule comprising CFA antigens I, II and IV, three STa$_{toxoid}$ antigens and a LT$_{toxoid}$ antigen, wherein the STa$_{toxoid}$ has an A14Q mutation or a N12S mutation.

In an embodiment, the present invention provides a fusion polypeptide molecule comprising CFA antigens I, II and IV, three STa$_{toxoid}$ antigens and a LT$_{toxoid}$ antigen, wherein the STa$_{toxoid}$ has a N12S mutation.

In accordance with another embodiment, the present invention provides a polynucleotide encoding a fusion polypeptide molecule comprising CFA antigens I, II and IV, three STa$_{toxoid}$ antigens and a LT$_{toxoid}$ antigen, wherein the STa$_{toxoid}$ has an A14Q mutation or a N12S mutation.

In an embodiment, the present invention provides a polynucleotide encoding a fusion polypeptide molecule comprising CFA antigens I, II and IV, three STa$_{toxoid}$ antigens and a LT$_{toxoid}$ antigen, wherein the STa$_{toxoid}$ has a N12S mutation.

In accordance with an embodiment, the present invention provides a fusion polypeptide molecule comprising three STa$_{toxoid}$ antigens and a LT$_{toxoid}$ antigen, wherein the three STa$_{toxoid}$ antigens lack a histidine tag and are selected from the group consisting of STa$_{A14Q}$ and STa$_{N12S}$.

In some embodiments, the present invention provides a fusion polypeptide molecule comprising three STa$_{toxoid}$ antigens and a LT$_{toxoid}$ antigen, wherein the three STa toxoid antigens lack a histidine tag and have the N12S mutation.

In accordance with an embodiment, the present invention provides a polynucleotide encoding a fusion polypeptide molecule comprising three STa$_{toxoid}$ antigens and a LT$_{toxoid}$ antigen, wherein the three STa$_{toxoid}$ antigens lack a histidine tag and are selected from the group consisting of STa$_{A14Q}$ and STa$_{N12S}$.

In some embodiments, the present invention provides a polynucleotide encoding a fusion polypeptide molecule comprising three STa$_{toxoid}$ antigens and a LT$_{toxoid}$ antigen, wherein the three STa$_{toxoid}$ antigens lack a histidine tag and have the N12S mutation.

In accordance with another embodiment, the present invention provides a fusion polypeptide molecule comprising CFA antigens I, II and IV, three STa$_{toxoid}$ antigens lacking a histidine tag and a LT$_{toxoid}$ antigen, wherein the STa$_{toxoid}$ has an A14Q mutation or a N12S mutation.

In an embodiment, the present invention provides a fusion polypeptide molecule comprising CFA antigens I, II and IV, three STa$_{toxoid}$ antigens lacking a histidine tag and a LT$_{toxoid}$ antigen, wherein the STa$_{toxoid}$ has a N12S mutation.

It will be understood by those of skill in the art that the fusion polypeptides disclosed herein can be used to prepare medicaments for use in treatment of various enteric diseases.

In accordance with an embodiment, the present invention provides the use of a polypeptide molecule comprising one or more of the colonization factor antigens (CFA) antigens CFA/I, CFA/II (CS1, CS2, CS3), CFA/IV (CS4, CS5, CS6) and/or comprising the amino acid sequence of SEQ ID NO: 1, or having at least 90% identity to SEQ ID NO: 1 in the treatment of for the therapy or prophylaxis of Enterotoxigenic *Escherichia coli* (ETEC), infection in a subject or for the therapy or prophylaxis of diarrhea in a subject comprising administering to the subject an effective amount of the polypeptide molecule.

In accordance with a further embodiment, the present invention provides the use of a polypeptide molecule comprising the colonization factor antigens (CFA) antigens CFA/I, CFA/II (CS1, CS2, CS3), CFA/IV (CS4, CS5, CS6) and further comprising heat-labile toxin (LT) and heat-stable toxin (STa) and/or comprising the amino acid sequence of SEQ ID NO: 2 and/or 3, in the treatment of for the therapy or prophylaxis of Enterotoxigenic *Escherichia coli* (ETEC), infection in a subject or for the therapy or prophylaxis of diarrhea in a subject comprising administering to the subject an effective amount of the polypeptide molecule.

In accordance with an embodiment, the present invention provides the use of a fusion polypeptide molecule comprising CFA antigens I, II and IV, STa$_{toxoid}$ and LT$_{toxoid}$, in the treatment of for the therapy or prophylaxis of Enterotoxigenic *Escherichia coli* (ETEC), infection in a subject or for the therapy or prophylaxis of diarrhea in a subject comprising administering to the subject an effective amount of the polypeptide molecule.

In accordance with another embodiment, the present invention provides the use of a fusion polypeptide molecule comprising CFA antigens I, II and IV, STa$_{toxoid}$ and LT$_{toxoid}$, wherein the STa$_{toxoid}$ has an A14Q mutation or a N12S mutation, in the treatment of for the therapy or prophylaxis of Enterotoxigenic *Escherichia coli* (ETEC), infection in a subject or for the therapy or prophylaxis of diarrhea in a subject comprising administering to the subject an effective amount of the polypeptide molecule.

In accordance with an embodiment, the present invention provides the use a fusion polypeptide molecule comprising CFA antigens I, II and IV, three STa$_{toxoid}$ antigens and a LT$_{toxoid}$ antigen, wherein the STa$_{toxoid}$ has an A14Q mutation or a N12S mutation, in the treatment of for the therapy or prophylaxis of Enterotoxigenic *Escherichia coli* (ETEC), infection in a subject or for the therapy or prophylaxis of diarrhea in a subject comprising administering to the subject an effective amount of the polypeptide molecule.

As used herein, the term "multiepitope fusion antigen (MEFA)" is an approach which combines both the fusion and epitope vaccine strategies. MEFAs can be made and developed for production of multivalent vaccines against other heterogeneous pathogens or perhaps different diseases. The MEFA methods of the present invention allows for the addition of any antigenic element, such as future-identified virulence factors (or emerging factors that become more prevalent or virulent, such as CS21 adhesin, which shows association with traveler's diarrhea), or multiple copies of one element such as STa toxoid.

The term, "amino acid" includes the residues of the natural α-amino acids (e.g., Ala, Arg, Asn, Asp, Cys, Glu, Gln, Gly, His, Hyl, Ile, Leu, Met, Phe, Pro, Ser, Thr, Trp, Tyr, and Val) in D or L form, as well as β-amino acids, synthetic and unnatural amino acids. Many types of amino acid residues are useful in the adipokine polypeptides and the invention is not limited to natural, genetically-encoded amino acids. Examples of amino acids that can be utilized in the peptides described herein can be found, for example, in Fasman, 1989, CRC Practical Handbook of Biochemistry and Molecular Biology, CRC Press, Inc., and the reference cited therein. Another source of a wide array of amino acid residues is provided by the website of RSP Amino Acids LLC.

The term, "peptide," as used herein, includes a sequence of from four to sixteen amino acid residues in which the α-carboxyl group of one amino acid is joined by an amide bond to the main chain (α- or β-) amino group of the adjacent amino acid. The peptides provided herein for use in the described and claimed methods and compositions can be cyclic.

In accordance with an embodiment, the present invention provides a vaccine composition comprising the polypeptide molecule described herein, and a pharmaceutically acceptable carrier.

In accordance with another embodiment, the present invention provides a method for the therapy or prophylaxis of Enterotoxigenic *Escherichia coli* (ETEC), infection in a subject comprising administering to the subject the polypeptide molecules or the vaccines described herein.

In accordance with a further embodiment, the present invention provides a method for the therapy or prophylaxis of diarrhea in a subject comprising administering to the subject the polypeptide molecules or the vaccines described herein.

In accordance with still another embodiment, the present invention provides a method for the therapy or prophylaxis of Enterotoxigenic *Escherichia coli* (ETEC), infection in a subject comprising administering to the subject the polypeptide molecules or the vaccines described herein and administration of at least one additional therapeutic agent.

The term, "amount effective to treat diarrhea" is that amount effective to treat, ameliorate, or prevent acute and prolonged (<1 month) or chronic (>1 month) diarrhea or symptoms thereof, or to exhibit a detectable therapeutic or preventative effect.

The precise effective amount for a human subject will depend upon the severity of the subject's disease state, general health, age, weight, gender, diet, time and frequency of administration, drug combination(s), reaction sensitivities, and tolerance or response to therapy. A routine experimentation can determine this amount and is within the judgment of the medical professional. Compositions may be administered individually to a patient, or they may be administered in combination with other drugs, hormones, agents, and the like.

With respect to peptide compositions described herein, the carrier can be any of those conventionally used, and is limited only by physico-chemical considerations, such as solubility and lack of reactivity with the active compound(s), and by the route of administration. The carriers described herein, for example, vehicles, adjuvants, excipients, and diluents, are well-known to those skilled in the art and are readily available to the public. It is preferred that the carrier be one which is chemically inert to the active agent(s), and one which has little or no detrimental side effects or toxicity under the conditions of use. Examples of the carriers include soluble carriers such as known buffers which can be physiologically acceptable (e.g., phosphate buffer) as well as solid compositions such as solid-state carriers or latex beads.

The carriers or diluents used herein may be solid carriers or diluents for solid formulations, liquid carriers or diluents for liquid formulations, or mixtures thereof.

Solid carriers or diluents include, but are not limited to, gums, starches (e.g., corn starch, pregelatinized starch), sugars (e.g., lactose, mannitol, sucrose, dextrose), cellulosic materials (e.g., microcrystalline cellulose), acrylates (e.g., polymethylacrylate), calcium carbonate, magnesium oxide, talc, or mixtures thereof.

For liquid formulations, pharmaceutically acceptable carriers may be, for example, aqueous or non-aqueous solutions, or suspensions. Examples of non-aqueous solvents are propylene glycol, polyethylene glycol, and injectable organic esters such as ethyl oleate. Aqueous carriers include, for example, water, alcoholic/aqueous solutions, cyclodextrins, emulsions or suspensions, including saline and buffered media.

Parenteral vehicles (for subcutaneous, intravenous, intraarterial, or intramuscular injection) include, for example, sodium chloride solution, Ringer's dextrose, dextrose and sodium chloride, lactated Ringer's and fixed oils. Formulations suitable for parenteral administration include, for example, aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

It will be appreciated by one of skill in the art that, in addition to the above-described vaccine compositions, the polypeptides of the invention can be formulated as inclusion complexes, such as cyclodextrin inclusion complexes, or liposomes.

Intravenous vehicles include, for example, fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, and glycols such as propylene glycols or polyethylene glycol are preferred liquid carriers, particularly for injectable solutions.

In one or more preferred embodiments, the route of administration of the above-described vaccine compositions, the route is intradermal or subcutaneous for polypeptide vaccine delivery and in other embodiments, the route is oral for whole cell vaccine.

In addition, in an embodiment, the compositions comprising polypeptides or vaccines thereof, may further comprise binders (e.g., acacia, cornstarch, gelatin, carbomer, ethyl cellulose, guar gum, hydroxypropyl cellulose, hydroxypropyl methyl cellulose, povidone), disintegrating agents (e.g., cornstarch, potato starch, alginic acid, silicon dioxide, croscarmelose sodium, crospovidone, guar gum, sodium starch glycolate), buffers (e.g., Tris-HCl, acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., cremophor, glycerol, polyethylene glycerol, benzlkonium chloride, benzyl benzoate, cyclodextrins, sorbitan esters, stearic acids), anti-oxidants (e.g., ascorbic acid, sodium metabisulfite, butylated hydroxyanisole), stabilizers (e.g., hydroxypropyl cellulose, hyroxypropylmethyl cellulose), viscosity increasing agents (e.g., carbomer, colloidal silicon dioxide, ethyl cellulose, guar gum), sweetners (e.g., aspartame, citric acid), preservatives (e.g., thimerosal, benzyl alcohol, parabens), lubricants (e.g., stearic acid, magnesium stearate, polyethylene glycol, sodium lauryl sulfate), flow-aids (e.g., colloidal silicon dioxide), plasticizers (e.g., diethyl phthalate, triethyl citrate), emulsifiers (e.g., carbomer, hydroxypropyl cellulose, sodium lauryl sulfate), polymer coatings (e.g., poloxamers or poloxamines), coating and film forming agents (e.g., ethyl cellulose, acrylates, polymethacrylates), and/or adjuvants.

The choice of carrier will be determined, in part, by the particular peptide containing compositions, as well as by the particular method used to administer the composition. Accordingly, there are a variety of suitable formulations of the pharmaceutical compositions of the invention. The following formulations for parenteral, subcutaneous, intravenous, intramuscular, intraarterial, intrathecal and interperitoneal administration are exemplary, and are in no way limiting. More than one route can be used to administer the compositions of the present invention, and in certain instances, a particular route can provide a more immediate and more effective response than another route.

As used herein the term "pharmaceutically active compound" or "therapeutically active compound" means a compound useful for the treatment or modulation of a disease or condition in a subject suffering therefrom. Examples of pharmaceutically active compounds can include any drugs known in the art for treatment of disease indications.

Other therapeutically active compounds included in the pharmaceutical compositions suitable for use in the methods of the present invention include antidiarrheal agents.

Examples of such agents include, but are not limited to: bulking agents like methylcellulose, guar gum, kaolin suspensions or plant fiber (bran, sterculia, isabgol, etc.) are used for diarrhea in functional bowel disease and to control ileostomy output; absorbents which absorb toxic substances that cause infective diarrhea, such as methylcellulose; anti-inflammatory solutions, such as bismuth subsalicylate; and opioids, such as loperamide and diphenoxylate.

For purposes of the present invention, the term "diarrhea," as used herein means frequent, poorly formed, loose, watery stools of a subject. A subject having diarrhea means the subject is passing loose stools at least three times a day. The term "acute diarrhea" is a common problem that usually lasts<7 days but can last in a protracted or prolonged form for <21 days. Diarrhea lasting more than 2 days is often a sign of an enteropathogenic infection. The term "chronic diarrhea" means diarrhea that lasts at least 4 weeks. Chronic diarrhea symptoms may be continual or intermittent. The term "traveler's diarrhea" means diarrheal symptoms associated with travel-related infection. In addition to diarrhea, symptoms may include nausea, vomiting, abdominal pain, fever, sweats, chills, headache, and malaise. Diarrhea may also be the result of food borne enteropathogens.

Diarrhea of any duration may cause dehydration, which means the body lacks enough fluid and electrolytes—chemicals in salts, including sodium, potassium, and chloride—to function properly. Loose stools contain more water and electrolytes and often weigh more than solid stools.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount of any level of treatment or prevention of diarrhea in a mammal. Furthermore, the treatment or prevention provided by the inventive method can include treatment or prevention of one or more conditions or symptoms of the disease, e.g., diarrhea, being treated or prevented. Also, for purposes herein, "prevention" can encompass delaying the onset of the disease, or a symptom or condition thereof.

In accordance with an embodiment of the present invention, the medicament for treating a disease in a subject can encompass many different formulations known in the pharmaceutical arts, including, for example, intravenous and sustained release formulations.

As used herein, the term "treat," as well as words stemming therefrom, includes diagnostic and preventative as well as disorder remitative treatment.

As used herein, the term "subject" refers to any mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

An effective amount of the polypeptides or vaccine compositions, to be employed therapeutically will depend, for example, upon the therapeutic and treatment objectives, the route of administration, the age, condition, and body mass of the subject undergoing treatment or therapy, and auxiliary or adjuvant therapies being provided to the subject. Accordingly, it will be necessary and routine for the practitioner to titer the dosage and modify the route of administration, as required, to obtain the optimal therapeutic effect. A typical daily dosage might range from about 0.1 mg/kg to up to about 100 mg/kg or more, preferably from about 0.1 to about 10 mg/kg/day depending on the above-mentioned factors. Typically, the clinician will administer antibody until a dosage is reached that achieves the desired effect. In accordance with some embodiments, the dosage range for intradermal vaccine can be about 1 to 500 µg, preferably about 30 to 40 µg per dose in adults.

Included in the scope of the invention are functional variants of the inventive polypeptides or vaccine compositions described herein. The term "functional variant" as used herein refers polypeptides or vaccine compositions having substantial or significant sequence identity or similarity to polypeptides or vaccine compositions, which functional variant retains the biological activity of polypeptides or vaccine compositions of which it is a variant. In reference to the parent polypeptide, or protein, the functional variant can, for instance, be at least about 30%, 50%, 75%, 80%, 90%, 98% or more identical in amino acid sequence to the parent polypeptide, or protein.

The functional variant can, for example, comprise the amino acid sequence of the parent polypeptides, or proteins of the present invention with at least one conservative amino acid substitution. Conservative amino acid substitutions are known in the art, and include amino acid substitutions in which one amino acid having certain physical and/or chemical properties is exchanged for another amino acid that has the same chemical or physical properties. For instance, the conservative amino acid substitution can be an acidic amino acid substituted for another acidic amino acid (e.g., Asp or Glu), an amino acid with a nonpolar side chain substituted for another amino acid with a nonpolar side chain (e.g., Ala, Gly, Val, Ile, Leu, Met, Phe, Pro, Trp, Val, etc.), a basic amino acid substituted for another basic amino acid (Lys, Arg, etc.), an amino acid with a polar side chain substituted for another amino acid with a polar side chain (Asn, Cys, Gln, Ser, Thr, Tyr, etc.), etc.

Functional variants can also include extensions of the inventive polypeptides. For example, a functional variant of the inventive polypeptides can include 1, 2, 3, 4 and 5 additional amino acids from either the N-terminal or C-terminal end of the polypeptide.

Alternatively or additionally, the functional variants can comprise the amino acid sequence of the inventive polypeptides, or proteins with at least one non-conservative amino acid substitution. In this case, it is preferable for the non-conservative amino acid substitution to not interfere with or inhibit the biological activity of the functional variant. Preferably, the non-conservative amino acid substitution enhances the biological activity of the functional variant, such that the biological activity of the functional variant is increased as compared to the inventive polypeptides, or proteins.

The inventive polypeptides or proteins can consist essentially of the specified amino acid sequence or sequences described herein, such that other components of the functional variant, e.g., other amino acids, do not materially change the biological activity of the functional variant.

The inventive polypeptides or proteins (including functional portions and functional variants) of the invention can comprise synthetic amino acids in place of one or more naturally-occurring amino acids. Such synthetic amino acids are known in the art, and include, for example, aminocyclohexane carboxylic acid, norleucine, α-amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, α-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, α-aminocyclopentane carboxylic acid, α-aminocyclohexane carboxylic acid, α-aminocycloheptane carboxylic acid, α-(2-amino-2-norbornane)-carboxylic acid, α,γ-diaminobutyric acid, α,β-diaminopropionic acid, homophenylalanine, and α-tert-butylglycine.

The inventive polypeptides or proteins (including functional portions and functional variants) can be glycosylated, amidated, carboxylated, phosphorylated, esterified, N-acylated, cyclized via, e.g., a disulfide bridge, or converted into an acid addition salt and/or optionally dimerized or polymerized, or conjugated.

The inventive polypeptides or proteins (including functional portions and functional variants thereof) can be obtained by methods known in the art. Suitable methods of de novo synthesizing polypeptides and proteins are described in references, such as Chan et al., *Fmoc Solid Phase Peptide Synthesis*, Oxford University Press, Oxford, United Kingdom, 2005; *Peptide and Protein Drug Analysis*, ed. Reid, R., Marcel Dekker, Inc., 2000; *Epitope Mapping*, ed. Westwoood et al., Oxford University Press, Oxford, United Kingdom, 2000; and U.S. Pat. No. 5,449,752. Also, polypeptides and proteins can be recombinantly produced using the nucleic acids described herein using standard recombinant methods. See, for instance, Sambrook et al., *Molecular Cloning: A Laboratory Manual*, 3$^{rd}$ ed., Cold Spring Harbor Press, Cold Spring Harbor, N.Y. 2001; and Ausubel et al., *Current Protocols in Molecular Biology*, Greene Publishing Associates and John Wiley & Sons, NY, 1994. Further, some of the ICRX-CP s, polypeptides, and proteins of the invention (including functional portions and functional variants thereof) can be isolated and/or purified from a source, such as a plant, a bacterium, an insect, a mammal, e.g., a rat, a human, etc. Methods of isolation and purification are well-known in the art. Alternatively, the inventive polypeptides or proteins described herein (including functional portions and functional variants thereof) can be commercially synthesized by companies, such as Synpep (Dublin, Calif.), Peptide Technologies Corp. (Gaithersburg, Md.), and Multiple Peptide Systems (San Diego, Calif.). In this respect, the inventive TCRs, polypeptides, and proteins can be synthetic, recombinant, isolated, and/or purified.

Further provided by the invention are nucleic acid molecules comprising a nucleotide sequence encoding the inventive polypeptides or proteins described herein (including functional portions and functional variants thereof).

By "nucleic acid" as used herein includes "polynucleotide," "oligonucleotide," and "nucleic acid molecule," and generally means a polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. It is generally preferred that the nucleic acid does not comprise any insertions, deletions, inversions, and/or substitutions. However, it may be suitable in some instances, as discussed herein, for the nucleic acid to comprise one or more insertions, deletions, inversions, and/or substitutions.

Preferably, the nucleic acids of the invention are recombinant. As used herein, the term "recombinant" refers to (i) molecules that are constructed outside living cells by joining natural or synthetic nucleic acid segments to nucleic acid molecules that can replicate in a living cell, or (ii) molecules that result from the replication of those described in (i) above. For purposes herein, the replication can be in vitro replication or in vivo replication.

The nucleic acids can be constructed based on chemical synthesis and/or enzymatic ligation reactions using procedures known in the art. See, for example, Sambrook et al., supra, and Ausubel et al., supra. For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, N$^6$-isopentenyladenine, 1-methylguanine, 1-methylinosine, 2,2-dimethylguanine, 2-methyladenine, 2-methylguanine, 3-methylcytosine, 5-methylcytosine, N$^6$-substituted adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N$^6$-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine. Alternatively, one or more of the nucleic acids of the invention can be purchased from companies, such as Macromolecular Resources (Fort Collins, Colo.) and Synthegen (Houston, Tex.).

The invention also provides substituted nucleic acid sequences which encode any of the substituted inventive polypeptides, substituted polypeptides, substituted proteins, or substituted functional portions or functional variants thereof.

In some embodiments, the substituted nucleic acid sequence may be optimized. Without being bound to a particular theory, it is believed that optimization of the nucleic acid sequence increases the translation efficiency of the mRNA transcripts. Optimization of the nucleic acid sequence may involve substituting a native codon for another codon that encodes the same amino acid, but can be translated by tRNA that is more readily available within a cell, thus increasing translation efficiency. Optimization of the nucleic acid sequence may also reduce secondary mRNA structures that would interfere with translation, thus increasing translation efficiency.

The polynucleotide sequence encoding an inventive polypeptide of the invention includes the exemplified sequences, as well as conservative variations of the exemplified polypeptide sequences. The term "conservative variation" as used herein refers to a replacement of an amino acid residue by another, biologically similar amino acid residue. Examples of conservative variations include the substitution of a hydrophobic residue such as isoleucine, valine, leucine or methionine for another, or the substitution of a polar residue for another, such as the substitution of arginine for lysine, glutamic for aspartic acid, or glutamine for asparagine, and the like. The term "conservative variation" also includes the use of a substituted amino acid in place of an unsubstituted parent amino acid, provided that an antibody that specifically interacts with the substituted polypeptide also is specifically immunoreactive with the unsubstituted polypeptide.

A polynucleotide of the invention can be obtained by several methods. For example, the polynucleotide can be isolated using hybridization or computer-based techniques which are well known in the art. These include, but are not limited to: 1) hybridization of genomic or cDNA libraries with probes to detect homologous nucleotide sequences; 2) antibody screening of expression libraries to detect cloned DNA fragments with shared structural features; 3) polymerase chain reaction (PCR) on genomic DNA or cDNA using primers capable of annealing to the DNA sequence of interest; 4) computer searches of sequence databases for similar sequences; and 5) differential screening of a subtracted DNA library.

In certain exemplary embodiments, vectors such as, for example, expression vectors, containing a nucleic acid encoding one or more inventive polypeptides described herein are provided. As used herein, the term "vector" refers to a nucleic acid molecule capable of transporting another nucleic acid to which it has been linked. One type of vector is a "plasmid," which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors." In general, expression vectors of utility in recombinant DNA techniques are often in the form of plasmids. In the present specification, "plasmid" and "vector" can be used interchangeably. However, the invention is intended to include such other forms of expression vectors, such as viral vectors (e.g., replication defective retroviruses, adenoviruses and adeno-associated viruses), which serve equivalent functions.

In certain exemplary embodiments, the recombinant expression vectors comprise a nucleic acid sequence (e.g., a nucleic acid sequence encoding one or more inventive polypeptides or fragments thereof described herein) in a form suitable for expression of the nucleic acid sequence in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence encoding one or more inventive polypeptides is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., poly-adenylation signals). Such regulatory sequences are described, for example, in Goeddel; Gene Expression Technology: Methods in Enzymology 185, Academic Press, San Diego, Calif. (1990). Regulatory sequences include those which direct constitutive expression of a nucleotide sequence in many types of host cells and those which direct expression of the nucleotide sequence only in certain host cells (e.g., tissue-specific regulatory sequences, e.g., adipose tissue). It will be appreciated by those skilled in the art that the design of the expression vector can depend on such factors as the choice of the host cell to be transformed, the level of expression of protein desired, and the like. The expression vectors described herein can be introduced into host cells to thereby produce proteins or portions thereof, including fusion proteins or portions thereof, encoded by nucleic acids as described herein (e.g., inventive peptides).

In accordance with an embodiment, the present invention provides the use of a polypeptide molecule comprising one or more of the colonization factor antigens (CFA) antigens CFA/I, CFA/II (CS1, CS2, CS3), CFA/IV (CS4, CS5, CS6) and/or comprising the amino acid sequence of SEQ ID NO: 1, or having at least 90% identity to SEQ ID NO: 1 in the treatment of for the therapy or prophylaxis of Enterotoxigenic *Escherichia coli* (ETEC), infection in a subject or for the therapy or prophylaxis of diarrhea in a subject comprising administering to the subject an effective amount of the polypeptide molecule.

In accordance with another embodiment, the present invention provides the use of a polypeptide molecule comprising the colonization factor antigens (CFA) antigens CFA/I, CFA/II (CS1, CS2, CS3), CFA/IV (CS4, CS5, CS6) and further comprising heat-labile toxin (LT) and heat-stable toxin (STa) and/or comprising the amino acid sequence of SEQ ID NO: 2 and/or 3, in the treatment of for the therapy or prophylaxis of Enterotoxigenic *Escherichia coli* (ETEC), infection in a subject or for the therapy or prophylaxis of diarrhea in a subject comprising administering to the subject an effective amount of the polypeptide molecule.

In accordance with a further embodiment, the present invention provides the use of a fusion polypeptide molecule comprising CFA antigens I, II and IV, $STa_{toxoid}$ and $LT_{toxoid}$, in the treatment of for the therapy or prophylaxis of Enterotoxigenic *Escherichia coli* (ETEC), infection in a subject or for the therapy or prophylaxis of diarrhea in a subject comprising administering to the subject an effective amount of the polypeptide molecule.

In some embodiments, the fusion polypeptides of the present invention are administered to the subject in a vaccine formulation.

In some embodiments, the administration of the fusion polypeptides of the present invention can be combined with the administration of at least one additional therapeutic agent.

It will be understood that the additional therapeutic agents which can be combined with administration of the fusion polypeptides of the present invention can include other drugs or biological agents. For example, the additional therapeutic agents can include anti-motility, antidiarrheals, antibiotics, antihelminths, and anti-parasiticals.

EXAMPLES

Bacterial strains and plasmids. *E. coli* strains and plasmids used in this study are listed in Table 1. ETEC field isolates deposited at Johns Hopkins University and the *E. coli* Reference Strain Center at University of Gothenburg (Sweden), and recombinant CS1 and CS2 *E. coli* strains (gifts from Dr. J. Scott at Emory University) (*Infect Immun* 58(11):3594-3600 (1990); *Infect Immun* 63(12):4849-4856 (1995)) were used for CFA adhesin extraction and in antibody adherence inhibition assays. *E. coli* BL21 (GE Healthcare, Piscataway, N.J.) and vector pET28a (Novagen, Madison, Wis.) were used to express the multiepitope CFA protein.

Recombinant strains 9175 (CFA/I/II/IV), 9164 ($3xSTa_{414Q}$-tmLT$_{S63K/R192G/L211A}$), and 9318 ($3xSTa_{N12S}$-LT$_{toxoid}$) were used as templates for CFA/I/II/IV-STa-toxoid-LT$_{toxoid}$ fusion construction. *E. coli* BL21 (GE Healthcare, Piscataway, N.J.) and vector pET28a (Novagen, Madison, Wis.) were used as templates first to construct the CFA/I/II/IV-STa$_{414Q}$-dmLT MEFA gene. Recombinant strain 9318 ($3xSTa_{N12S}$-dmLT$_{R192G/L211A}$) was included for the CFA/I/II/IV-STa$_{N12S}$-dmLT MEFA after $3xSTa_{N12S}$-LT$_{toxoid}$ was identified as the optimal toxoid fusion in inducing anti-STa antibody response. CFA multiepitope fusion antigen (MEFA) construction.

Epitopes from each of the CFA/I, CS1-CS6 major structural subunits (CfaB, CooA, CotA, CstH, CsaB, CsfA and CssA) were predicted with web-based programs (*Bioinformatics* 14(10):892-893 (1998); *J Mol Biol* 225(2):487-494 (1992); *J Mol Recognit* 16(1):20-22 (2003); *Methods Mol Biol* 409 (2007)) and classic algorithms (*Proc Natl Acad Sci USA* 78(6):3824-3828 (1981); *Biochemistry* 17(20):4277-4285 (1978); *Journal of theoretical biology* 21(2):170-201 (1968)). Antigenic epitopes predicted by all or a majority of the programs were initially selected, and CFA/I major structural subunit CfaB was used as the backbone for constructing the CFA multiepitope fusion antigen. With nucleotides coding the most antigenic epitope were retained, the CfaB gene (cfaB) had nucleotides coding the surface-exposed but less antigenic epitopes substituted with nucleotides coding the most antigenic epitope of the CS1-CS6 major structural subunits, in a sequence so that the protein encoded by this chimeric gene is similar to CfaB in antigenicity propensity. This chimeric gene, after silent mutation to fit PCR primer design and cloning purposes, was synthesized (Integrated DNA Technologies, Inc., Coralville, Iowa). The synthesized gene was amplified in a PCR with pfu Taq polymerase (Strategene, La Jolla, Calif.) and primers pETCFA-F (5'-gtgagtgetagcgcagtagaggattffitcatt-'3; NheI site underlined) (SEQ ID NO: 15) and pETCFA-R (5'-ctcteggccgttatcag-gcteccaaagtcattacaag-'3; EagI site underlined) (SEQ ID NO: 16), digested with NheI/EagI restriction enzymes (New England Biolabs, Ipswich, Mass.), and ligated into expression vector pET28a using standard protocols. The cloned multiepitope CFA subunit gene was verified with DNA sequencing.

Multiepitope 'CFA/I/II/IV-STa$_{toxoid}$-LT$_{toxoid}$' fusion construction. Splicing overlap extension (SOE) PCR was used to construct genetic fusions as described previously. Two PCR products, the multiepitope CFA carrying antigenic epitopes of 7 CFA adhesins (CFA/I, CFA/II, and CFA/IV) and the STa-LT$_{toxoid}$ fusion including 2 copies of the STa-toxoid, LTA(131-240) and LTB were overlapped for the CFAXII/IV-STa$_{toxoid}$-LT$_{toxoid}$ chimeric gene. The multiepitope CFA fragment was amplified with primers T7-F (5'-taatacgactcactataggg-'3) (SEQ ID NO: 17) and CFA-toxoid-R (5'-accaaaggctcccaaagtcattacaagagatactactectga-'3) (SEQ ID NO: 18) using plasmid pCFAXIFIV as the DNA template. Two toxoid fragments were amplified with primers CFA-toxoid-F (5'-gtaatgactttgggagcctttggtgtgattgatgaacgat-tacatcgt-'3) (SEQ ID NO: 19) and T7-R (5'-tgctagttattggtca-ggggt-'3) (SEQ ID NO: 20) using plasmid p3xSTa$_{414Q}$-tmLT and plasmid p3xSTa$_{N12S}$-dmLT respectively as the DNA templates. Primers hSTa$_{N12S}$-F (5'-gaa ttg tgt tgt agc cct gct tgt-'3) (SEQ ID NO: 32) and hSTa$_{N12S}$-R (5'-aca agc agg gct aca aca caa ttc-'3) (SEQ ID NO: 33); and hSTa$_{414Q}$-F (tgt tgt aat cct cag tgt acc ggg-'3) (SEQ ID NO: 34) and hSTa$_{414Q}$-R (5'-ccc ggt aca ctg agg att aca aca-'3) (SEQ ID NO: 35) were used to mutate the STa gene for STa toxoids STa$_{N12S}$ and STa$_{414Q}$ respectively. Each SOE product was further amplified with T7-F and T7-R primers, digested with NheI/EagI restriction enzymes (New England BioLabs, Ipswich, Mass.), ligated into expression vector pET28α, and verified with DNA sequencing.

Expression and detection of the CFA MEFA protein. *E. coli* strain BL21 was transformed with the plasmid carrying CFA/I/II/IV-STa$_{414Q}$-LT$_{toxoid}$ or CFA/I/II/IV-STa$_{N12S}$-LT$_{toxoid}$ chimeric gene to express two CFA/I/II/IV-STa$_{toxoid}$-LT$_{toxoid}$ MEFA proteins. This strain was grown in 5 ml Luria Bertani (LB) broth supplemented with kanamycin (30 μg/ml) at 37° C. overnight on a shaker (150 rpm). Overnight growth was added to 500 ml 2×YT (2× Yeast extract and Tryptone) medium for continuous incubation until the optical density reached 0.5 at 600 nm (OD600). The culture was then induced with isopropyl-1-thio-β-D-galactoside (IPTG; 0.5 mM) and incubated for 4 more hours. The bacterial culture was centrifuged at 5,000×g for 20 minutes, and pellets were suspended into 10 ml bacterial protein extraction reagent (B-PER, in phosphate buffer; Pierce, Rockford, Ill.) for total insoluble protein (inclusion body fraction) extraction.

Recombinant 6xHis-tagged CFA multiepitope fusion antigen protein was further extracted from total insoluble protein extracts (in denatured buffer) to a purity of greater than 90% with Ni-nitrilotriacetic acid (NTA) agarose (QIAGEN, Valencia, Calif.). Extracted 6xHis-tagged protein was refolded using a Protein Refolding kit by following the manufacturer's protocol (Novagen, Madison, Wis.), dialyzed in 20 mM Tris-HCl buffer overnight at 4° C., and was concentrated (to 1-2 mg/ml) using Spectra/Por® molecular porous membrane tubing (Spectrum Laboratories Inc., Rancho Dominguez, Calif.) and polyethylene glycol compound (PEG; Sigma, St. Louis, Mo.) (Infection and immunity 78(1):316-325 (2010); *Clin Vaccine Immunol* 18(10):1593-1599 (2011)).

Ten microliters of refolded protein (10-20 μg) was analyzed in 12% sodium dodecyl sulfate polyacrylamide gel electrophoresis (SDS-PAGE) with anti-CFA/I (000419; diluted in 1:100), -CS1 (990505; 1:200), -CS2 (990505; 1:100), -CS3 (960607; 1:200), -CS4 (000419; 1:100), -CS5 (960607; 1:100), and anti-CS6 (060424; 1:200) MAbs hybridoma supernatant (provided by Dr. A. M. Svennerholm), respectively. Rabbit anti-CT serum (1:3300; Sigma) and protein-A column-purified rabbit anti-STa serum (1:3300; provided by Dr. DC Robertson) (Infect. Immun., 78: 316-325 (2010)) were used as the primary antibody. IRDye-labeled goat anti-mouse IgG (1:5000; LI-COR, Lincoln, Nebr.) was used as the secondary antibody. Bound CFAXIFIV-STa$_{toxoid}$-LT$_{toxoid}$ fusion proteins were detected using a LI-COR Odyssey premium infrared gel imaging system (LI-COR).

Mouse immunization with the CFA/I/II/IV-STa$_{toxoid}$-LT$_{toxoid}$ MEFA proteins. Mouse immunization studies complied with the Animal Welfare Act by following the 1996 National Research Council guidelines and were approved and supervised by a state veterinarian and by the Kansas State University Institutional Animal Care and Use Committee. CFA/I/II/IV-STa$_{toxoid}$-LT$_{toxoid}$ MEFA proteins were verified non-toxic using T-84 cells and EIA cAMP and cGMP kits (Assay Design, MI) prior to being used in mouse immunization as previously described. Four groups of 6- to 8-week-old female BALB/c mice (Charles River Laboratories International, Inc., Wilmington, Mass.) were included in the immunization study. The first group of 8 mice was each injected intraperitoneally (i.p.) with 200 μg CFA/I/II/IV-STa$_{A14Q}$-LT$_{toxoid}$ refolded protein (in 200 μl 20 mM Tris-HCl) and an equal volume of Freund's complete adjuvant (CFA; Sigma). The second group of 15 mice was each injected (i.p.) with 200 μg CFA/I/II/IV-STa$_{N12S}$-LT$_{toxoid}$ refolded protein (in 200 μl 20 mM Tris-HCl) with 200 μl CFA. The third group of 16 mice was each co-administered (i.p.) with refolded CFA/I/II/IV MEFA and toxoid fusion 3xSTa$_{N12S}$-LT$_{toxoid}$ produced previously. To have the molecule copy numbers of CFA/I/II/IV and 3xSTa$_{N12S}$-dmLT antigens be equivalent to 200 μg CFA/I/II/IV-STa$_{N12S}$-LT$_{toxoid}$ (based on peptide lengths of the CFAI/II/IV and the STa$_{N12S}$-dmLT peptides), 80 μg CFA/I/II/IV and 150 μg 3xSTa$_{N12S}$-LT$_{toxoid}$ (in a total of 200 μl 20 mM Tris-HCl) with 200 μl CFA were injected to each mouse in this co-administration group. The fourth group of 9 mice was each injected (i.p.) with 200 μl CFA and 200 μl 20 mM Tris-HCl and served as the control. Two booster injections at the same doses as the primary but with Freund's incomplete adjuvant (IFA) were followed at a bi-week interval. In addition, a group of five mice was each immunized (i.p.) with 200 μg CFA/I fimbria heat-extracted from ETEC H10407 and 200 μl Freund's adjuvants (CFA in the primary and IFA in boosters) to serve as a reference for mouse anti-CFA/I antibody response.

Blood and fecal pellets were collected from each mouse prior to immunization and 10 to 12 days after each immunization. Fecal pellets were suspended in fecal reconstitution buffer supplemented with protease inhibitor phenylmethylsulfonyl fluoride (Sigma) at a ratio of 1:6 (1 gram feces to 5 ml buffer), and centrifuged to collect supernatants referred as fecal suspension samples. In addition, intestines collected from each mouse at necropsy were minced with a pair of surgical scissors in fecal reconstitution buffer (1 g intestine tissue in 2.5 ml buffer, a 1:3.5 dilution), vortexed for 1 minute, and centrifuged at 10,000×g for 10 minutes to collect supernatants as intestinal wash samples. Serum samples were stored at −80° C. until use. On day 37 after the primary, mice were anesthetized with $CO_2$ and exsanguinated. Collected serum, fecal suspension and intestine wash samples were stored at −80° C. until use.

Mouse anti-CFA antibody titration. Anti-CFA/I, -CS1, -CS2, -CS3, -CS4/CS6, -CS5/CS6, and anti-CS6 IgG in serum and IgA antibodies in fecal and intestine suspension were examined in ELISAs. CFA/I, CS1, CS2, CS3, CS4/CS6, and CS5/CS6 adhesins extracted from ETEC field strains or recombinant E. coli strains listed in Table 1, in an adhesin heat extraction method described previously (Clin Vaccine Immunol 17(12):1859-1867 (2010)), were used as coating antigens. A half microgram of each adhesin [in 100 μl antigen coating buffer (0.015 M $Na_2CO_3$, 0.035 M $NaHCO_3$, pH 9.6)] was added to each well of an Immulon 2HB plate (Thermo Scientific, Rochester, N.Y.), and incubated for 1 hour at 37° C. then followed by overnight at 4° C. In addition, 100 ng extracted CS6 adhesin (provided by Walter Reed Army Institute of Research) was also used to verify anti-CS6 specific antibodies. Coated plates were washed 3 times with PBST (0.05% Tween-20), blocked with 200 μl 10% non-fat milk-PBST for 1 hour at 37° C. After 3 washes with PBST, each well was incubated with serum (1:200, diluted in 2.5% milk-PBST), fecal suspension (1:20 or 1:10) or the intestine suspension sample (1:20 or 1:10) of each immunized or control mouse (in triplicate) for 1 hour at 37° C. Plates were washed 5 times with PBST, and each well was added with 100 μl 1:3000 diluted HRP-conjugated goat anti-mouse IgG (Sigma) or 1:1000 diluted IgA (Sigma) 1 hour at 37° C., followed by 3 more washes and incubation with 100 μl TMB Microwell Peroxidase Substrate System (2-C) (KPL, Gaitherburg, Md.) for 30 minutes at room temperature. Optical density (OD) was measured at a plate reader with 405 nm wavelength. OD readings, greater than 0.3 after subtraction to background readings, or the highest readings for the control, were calculated to antibody titers at a $log_{10}$ scale.

Mouse anti-CFA and anti-toxin antibody titration. Anti-CFA/I, -CS1, -CS2, -CS3, -CS4/CS6, -CS5/CS6, -STa, and anti-LT IgG antibodies in serum sample of each mouse were titrated as described previously. Briefly, 500 ng CFA/I, CS1, CS2, CS3, CS4/CS6, and CS5/CS6 CFA adhesins extracted from ETEC field isolates or recombinant E. coli strains (Table 1), 10 ng STa-ovalbumin conjugates, or 100 ng LT (List Biological Laboratories, Inc., Campbell, Calif.) were coated to each well of H2B plates (Thermo Scientific, Rochester, N.Y.; for anti-CFA and anti-LT IgG) or Costar plates (Corning Inc., Corning, N.Y.; for anti-STa IgG) to titrate anti-CFA and antitoxin antibodies, respectively. HRP-conjugated goat anti-mouse IgG (1:3300; Sigma) and TMB Microwell Peroxidase Substrate System (2-C) (KPL, Gaitherburg, Md.) were used to measure optical density (OD) at a wavelength of 405 nm. OD readings, greater than 0.3 after subtraction to background readings were calculated to antibody titers and expressed in a $log_{10}$ scale.

Anti-adhesin antibody adherence inhibition assay. Mouse serum and fecal suspension samples were examined for adherence inhibition against ETEC strains expressing CFA/I, CS3, CS4/CS6, or CS5/CS6 adhesins, and E. coli recombinant strains expressing CS1 or CS2, using Caco-2 cells (ATCC, # HTB-37TM) as previously described. Caco-2 cells ($7 \times 10^5$) were seeded at each well of a 12-well tissue culture plate containing DMEM-20% FBS (Fisher Thermo Scientific, Pittsburg, Pa.). ETEC and E. coli recombinant bacteria grown overnight at 37° C. on sheep blood agar plates were scraped off with Q-tips, and were gently suspended in sterile PBS. One hundred microliter of each bacterial suspension ($3.5 \times 10^6$ CFUs; with a multiplicity-of-infection ratio set at five bacteria to one Caco-2 cell) was incubated with 20 μl serum sample which was pooled from each group on a shaker (50 rpm) for 1 hour at room temperature. The mixture of bacteria and the serum sample was brought to 300 μl with PBS, added to each well containing the Caco-2 cells (in 700 μl cell culture medium), and incubated 1 hour at 37° C. in a $CO_2$ incubator (5% $CO_2$). Wells were washed with PBS to remove non-adherent bacteria, and incubated with 0.25% trypsin (200 μl per well) 30 minutes at 37° C. in a $CO_2$ incubator to dislodge Caco-2 cells. Dislodged Caco-2 cells (with adherent bacteria) were collected by centrifugation (15,000 g for 10 minutes) and suspended in 1 ml PBS. Suspension was serially diluted, plated on LB plates and cultured at 37° C. to count overnight grown bacteria (CFUs).

Antitoxin antibody neutralization against STa toxin and CT. Serum samples pooled from mice in each group were also examined for in vitro antibody neutralization activities against STa and CT using EIA cAMP and cGMP kits (Assay Design) and T-84 cells. STa stimulates an increase of intracellular cyclic GMP levels and CT elevates intracellular cAMP levels in T-84 cells. Neutralizing antitoxin antibodies neutralize enterotoxicity thus prevent STa and CT from stimulating intracellular cGMP or cAMP. Therefore, by incubating serum with the toxin, adding the mixture to T-84 cells, and measuring cGMP or cAMP levels in the cells, we are able to evaluate neutralization activities of mouse serum IgG antibodies against STa or CT. Serum sample, 30 μl pooled from each group, was incubated with 2 ng STa toxin or 10 ng CT (CT is an homologue of LT, and is commonly used in anti-LT antibody neutralization assay) for 30 minutes at room temperature. The serum and toxin mixture was then brought to 300 μl in total with DMEM/F12 medium, and was added to T-84 cells (with 700 μl culture medium), and incubated 1 hour at 37° C. in a $CO_2$ incubator. Cells were washed with PBS and lysed with 300 μl 0.1M HCl (with 0.5% Triton X-100) at room temperature for 20-30 minutes. After incubation in a $CO_2$ incubator for 1 hour (for STa to measure cGMP) or 3 h (for CT to measure cAMP), intracellular cGMP or cAMP levels (pmole/ml) in T-84 cell were measured with EIA cGMP or cAMP kit by following the manufacturer's protocol (Assay Design). STa or CT alone (without serum) was used as the control to show enterotoxicity in stimulation of cGMP or cAMP in T-84 cells, and culture medium only (without toxin or serum) was used to show a baseline of T-84 intracellular cAMP or cGMP level.

Statistical analysis. Data were analyzed by using SAS for windows, version 8 (SAS Institute, Cary, N.C.). Results were expressed as means±standard deviations. Student's t-test was used to compare the different treatment groups. Calculated p values of less than 0.05 were regarded as significant when treatments were compared at two-tailed distribution and two-sample equal or unequal variance.

Example 1

Constructed chimeric protein carried representative epitopes from all 7 adhesins. The CFA/I and CS1-CS6 major subunits: CfaB, CooA, CotA, CstH, CsaB, CsfA and CssA, deducted from the cfaB gene sequence (GenBank accession # M55661), cooA gene (X62495), cotA gene (Z47800.1), cstH gene (M35657.1), csaB gene (AY281092.1), csfA gene (AJ224079.2) and the cssA gene (U04846.1), had peptides $^{159}$SGVVSLVMT$^{167}$ (SEQ ID NO: 4), $^{97}$PTLQIPVS$^{104}$ (SEQ ID NO: 5), $^{161}$LVSIVLT$^{167}$ (SEQ ID NO: 6), $^{61}$NTLVGVLTL$^{69}$ (SEQ ID NO: 7) $^{79}$KNVLVKLV$^{86}$ (SEQ ID NO: 8), $^{83}$DFFIVPVSG$^{91}$ (SEQ ID NO: 9), and $^{72}$QVTVYPV$^{78}$ (SEQ ID NO: 10), predicted, respectively. By replacing the less antigenic peptides $^{26}$KNITVTASV$^{34}$ (SEQ ID NO: 21), $^{63}$FESYRVMTQ$^{71}$ (SEQ ID NO: 22), $^{80}$KVIVKLAD$^{87}$ (SEQ ID NO: 23), $^{97}$STVQMPIS$^{104}$ (SEQ ID NO: 24), $^{106}$SWGGQVL$^{112}$ (SEQ ID NO: 25), and $^{134}$VSSSQEL$^{140}$ (SEQ ID NO: 26), of CfaB with the representative peptides of CsfA (CS5), CstH (CS3), CsaB (CS4), CooA (CS1), CssA (CS6), and the CotA (CS2), we constructed a CFA multiepitope fusion antigen in silico. Web-based analyses suggested this putative CFA multiepitope fusion antigen possessed an antigenic propensity and hydrophilicity similar to those of the native CFA/I major subunit CfaB. We then replaced nucleotides coding these six peptides of the cfaB gene with nucleotides coding the most antigenic peptide of each of these 6 CS subunit genes, and had a chimeric multiepitope CFA gene constructed.

The overlap of CFA/I/IFIV MEFA and the 3xSTa$_{A14Q}$-LT$_{toxoid}$ or 3xSTa$_{N12S}$-LT$_{toxoid}$ PCR amplified products yielded two CFA/I/II/IV-STa$_{toxoid}$-LT$_{toxoid}$ chimeric genes (FIG. 1). Two recombinant strains, 9208 and 9401, were constructed to express two CFA/I/II/IV-STa$_{toxoid}$-LT$_{toxoid}$ MEFA proteins. Two MEFA proteins differed only at the STa toxoid, with STa$_{A14Q}$ in 9208 and STa$_{N12S}$ in 9401 (Table 1).

TABLE 1

E. coli strains and plasmid used in the present invention.

| | Relevant properties | Sources |
|---|---|---|
| Strains | | |
| BL21 | B F⁻, ompT, hsdS ($r_B^-$, $m_B^-$), gal, dcm. | GE Healthcare |
| H10407 | O78:H11; CFA/I, LT, STa | Johns Hopkins Univ. |
| EL 392-75 | O6:H16; CS1/CS3, LT, STa | Johns Hopkins Univ. |
| UM 75688 | CS5/CS6, LT, STa | Johns Hopkins Univ. |
| E106 (E11881/9) | CS4/CS6, LT, STa | Univ. of Gothenburg |
| E116 (E19446) | CS3, LT, STa | Univ. of Gothenburg |
| THK38/pEU405 | CS1 | Emory Univ. |
| DH5α/pEU588 | CS2 | Emory Univ. |
| 9175 | pCFA/I/II/IV in BL21 | Present invention |
| 9164 | p3xSTa$_{A14Q}$-tmLT in BL21 | Zhang et al., 2013 |
| 9318 | p3xSTa$_{N12S}$-LT$_{toxoid}$ in BL21 | Present invention |
| 9208 | pCFA/I/II/IV-STa$_{A14Q}$-LT$_{toxoid}$ in BL21 | Present invention |
| 9401 | pCFA/I/II/IV-STa$_{N12S}$-LT$_{toxoid}$ in BL21 | Present invention |
| Plasmids | | |
| pET28α | | Novagen |
| pEU405 | CS1 | Emory Univ. |
| pEU588 | CS2 | Emory Univ. |
| pCFA/I/II/IV | multiepitope CFA subunit gene in pET28α at NheI/EagI | Present invention |
| p3xSTa$_{A14Q}$-tmLT | 3xSTa$_{A14Q}$-tmLT fusion gene in pET28α at NheI/EagI | Zhang et al., 2013 |
| p3xSTa$_{N12S}$-LT$_{toxoid}$ | 3xSTa$_{N12S}$-LT$_{toxoid}$ fusion gene in pET28α at NheI/EagI | Present invention |
| pCFA/I/II/IV-STa$_{A14Q}$-LT$_{toxoid}$ | multiepitope CFA-2xSTa$_{A14Q}$-LT$_{toxoid}$ in pET28α at NheI/EagI | Present invention |
| pCFA/I/II/IV-STa$_{N12S}$-LT$_{toxoid}$ | multiepitope CFA-2xSTa$_{N14S}$-LT$_{toxoid}$ in pET28α at NheI/EagI | Present invention |

Example 2

The CFA multiepitope fusion antigen was expressed as the 6xHis-tagged protein. DNA sequencing results showed each chimeric gene was a single open reading frame for a single 6xHis-tagged CFA-$_{toxoid}$ protein. Each fusion protein consisted of 20 amino acids from the pET28a vector including the 6xHis tag (six histidines), the CFA MEFA (150 amino acids) carrying epitopes of CFA/I and CS1-CS6 major subunits (CfaB, CooA, CotA, CstH, CsaB, CsfA and CssA), two copies of STa$_{toxoid}$ STa$_{A14Q}$ or STa$_{N12S}$, 109 amino acids (132-240) of dmLTA C-terminal peptide and one copy of the LTB subunit (100 amino acids), and four intra-peptide linkers (FIG. 1C). The first copy of the STa$_{toxoid}$ (without the stop codon) with a 'GPVD' linker was inserted after the mutated 192th amino acid residue (Arg→Gly) of the LTA, and the second STa$_{toxoid}$ (with the stop codon) was at the C-terminus of the fusion protein with an L-linker.

SDS-PAGE with Coomassie blue staining showed over 90% of the 6xHis-tagged protein extracted from strains 9208 and 9401 had a molecular mass of about 48 KDa, the expected size of the 6xHis-tagged CFAI/II/IV-STa-$_{toxoid}$-LT$_{toxoid}$ MEFA protein. The 6xHis-tagged protein was recognized by anti-CFA/I and anti-CS1, -CS2, -CS3, -CS4, -CS5, and anti-CS6 MAb hybridoma supernatant, and rabbit anti-STa and anti-CT sera in Western blot assays (FIG. 1D).

Example 3

CFA/I/II/IV-STa-$_{toxoid}$-LT$_{toxoid}$ MEFA proteins were well tolerated and immunogenic. T-84 cells incubated with 100 µg refolded fusion protein CFA/I/II/IV-STa$_{A14Q}$-LT$_{toxoid}$ or CFA/I/II/IV-STa$_{N12S}$-LT$_{toxoid}$ showed no increase of intracellular cAMP and cGMP levels. That indicated that neither MEFA protein possessed detectable LT or STa enterotoxicity. Additionally, female adult mice did not display any noticeable adverse effects after i.p. immunization with either CFA/I/II/IV-STa-$_{toxoid}$-LT$_{toxoid}$ MEFA protein. Mice co-administrated with the multiepitope CFA/I/II/IV subunit protein and the 3xSTa$_{N12S}$-LT$_{toxoid}$ fusion also did not show any adverse effects.

Figure 2:
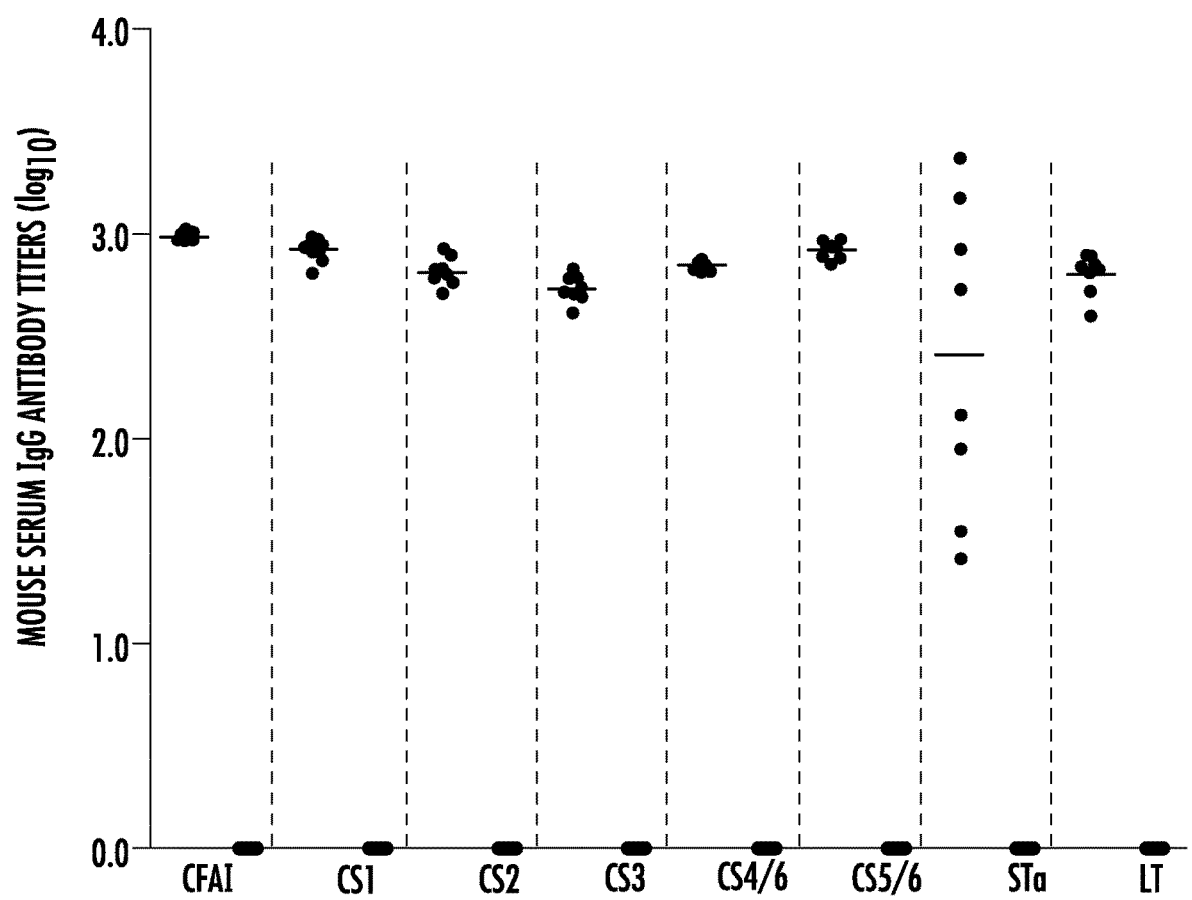
FIG. 2. Mouse serum anti-adhesin and antitoxin IgG antibody titers. Anti-CFA/I, anti-CS1, -CS2, -CS3, -CS4/CS6 and anti-CS5/CS6, and anti-STa and anti-LT IgG antibodies in the serum of each mouse immunized with 'CFA/I/II/IV-STa$_{414Q}$-LT$_{toxoid}$' fusion antigen (solid circles) and the serum of each control mouse (blank circles) were titrated in ELISAs. CFA/I, CS1, CS2, CS3, CS4/CS6, CS5/CS6 adhesin heat-extracted from *E. coli* or ETEC strains in Table 1 (500 ng per well of a 2HB plate), STa-ovalbumin (10 ng per well of a Costar plate), or LT (List Biological Laboratories, Inc.; 100 ng per well of a 2HB plate) and HRP-conjugated goat-anti-mouse IgG (1:3300; the secondary antibodies) were used to titrate IgG antibodies specific to CFA/I, CS1, CS2, CS3, CS4/6, CS5/6 adhesins and to STa and LT toxins, respectively. The antibody titer was calculated from the highest dilution of a serum sample that produced an ELISA optical density of greater than 0.3 (above the background) and presented in a $\log_{10}$ scale. Each dot represented a mouse IgG titer, and the bars indicated the mean titer of the group.
Figure 3:
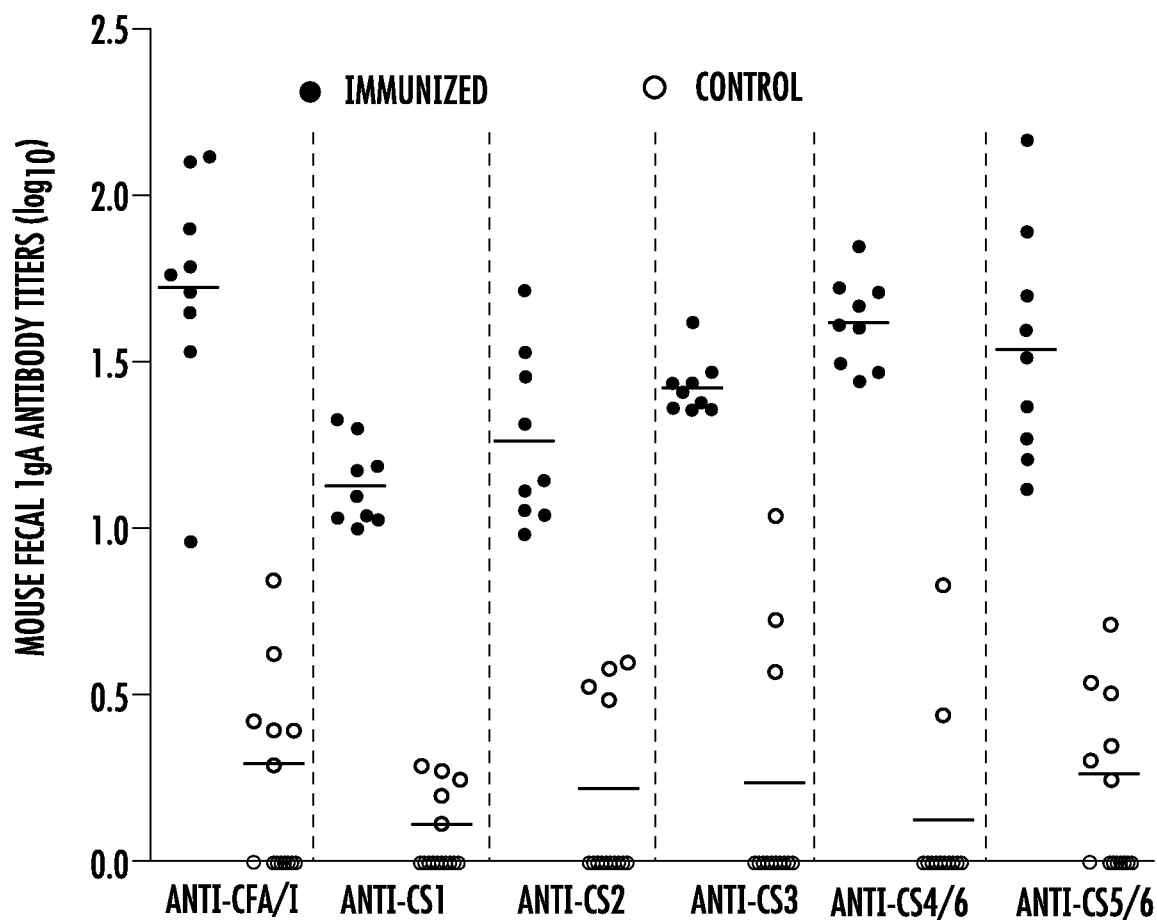
FIG. 3 depicts the titration of anti-CFA/I, -CS1, -CS2, -CS3, -CS4/CS6, -CS5/CS6, and anti-CS6 IgA antibodies in fecal suspension samples of the immunized mice (solid dots) and control mice (circles). Five hundred nanogram CFA adhesins heat-extracted from *E. coli* strains expressing CFA/I, CS1, CS2, CS3, CS4/CS6 or CS5/CS6 were coated to each well of an Immulon 2HB plate. Fecal suspension sample from each mouse (1:20 dilution), in triplicate, was added to each well. HRP-conjugated goat-anti-mouse IgA (1:1000) was used as the secondary antibodies. Optical densities were used to calculate anti-STa antibody titers (in $\log_{10}$).

Female C57BL/6 mice did not display any apparent adverse effects after i.p. immunized with this 6xHis-tagged CFA multiepitope fusion antigen protein. Mice immunized with CFA/I/II/IV-STa$_{A14Q}$-LT$_{toxoid}$ or CFA/I/II/IV-STa$_{N12S}$-LT$_{toxoid}$ developed immune responses to CFA/I, CS1, CS2, CS3, CS4/6, CS5/6, STa, and LT. Serum samples of the mice immunized with fusion CFA/I/II/IV-STa$_{A14Q}$-LT$_{toxoid}$ had anti-CFA/I, -CS1, -CS2, -CS3, -CS4/6, -CS5/6, -STa, and anti-LT IgG antibodies detected at titers (in log$_{10}$) of 2.98±0.02, 2.92±0.06, 2.81±0.07, 2.73±0.07, 2.84±0.03, 2.92±0.04, 2.40±0.75, and 3.19±0.01, respectively (FIG. 2). Serum samples from individual mice immunized with fusion CFA/I/II/IV-STa$_{N12S}$-LT$_{toxoid}$ also developed IgG antibody responses to CFA/I, CS1, CS2, CS3, CS4/6 and CS5/6 adhesins and both toxins (Table 2). Serum of the mice i.p. immunized with the heat-extracted CFA/I fimbriae had anti-CFA/I IgG detected at 2.95±0.01 (log$_{10}$).

There were no IgG antibodies specific to CFA/I, CFA/II, CFA/IV, STa or LT detected in the serum samples of the control mice or serum samples collected prior to the primary immunization.

TABLE 2

Anti-CFA/I, -CS1, -CS2, -CS3, -CS4/CS5, and anti-CS5/CS6, and anti-STa and anti-LT IgG antibody titers (in log$_{10}$; mean ± standard deviation) detected in the serum of mice immunized with the CFA/I/II/IV-STa$_{N12S}$-LT$_{toxoid}$ or co-immunized with the CFA/I/II/IV MEFA and the 3xSTa$_{N12S}$-LT$_{toxoid}$ toxoid fusion.

| Mouse immunization groups[a] | Mean serum IgG titer (log$_{10}$) ± stdev | | | | | | | |
|---|---|---|---|---|---|---|---|---|
| | anti-CFA/I | anti-CS1 | anti-CS2 | anti-CS3 | anti-CS4/6 | anti-CS5/6 | anti-STa | anti-LT |
| CFA/I/II/IV-STa$_{N12S}$-dmLT (n = 15) | 2.63 ± 0.09 | 2.54 ± 0.04 | 2.44 ± 0.10 | 2.50 ± 0.09 | 2.58 ± 0.06 | 2.66 ± 0.03 | 2.50 ± 0.52 | 2.12 ± 0.30 |
| CFA/I/II/IV plus 3xSTa$_{N12S}$-dmLT (n = 16) | 2.69 ± 0.05 | 2.56 ± 0.05 | 2.53 ± 0.08 | 2.50 ± 0.06 | 2.59 ± 0.03 | 2.67 ± 0.05 | 2.88 ± 0.08 | 2.27 ± 0.13 |
| p values[b] | 0.04 | 0.33 | 0.01 | 0.97 | 0.58 | 0.58 | 0.01 | 0.10 |

[a]Groups of mice immunized with 'CFA/I/II/IV-STa$_{N12S}$-LT$_{toxoid}$', or co-immunized with 'CFA/I/II/IV' and '3xSTa$_{N12S}$-LT$_{toxoid}$'. Anti-CFA/I, anti-CS1, anti-CS2, anti-CS3, anti-CS4/CS5 and anti-CS5/CS6, and anti-STa and anti-LT IgG in serum sample of each immunized mouse was titrated by ELISAs using heat-extracted adhesin (500 ng adhesin per well of 2HB plates), STa conjugates (10 ng STa-ovalbumin conjugates per well of CoStar plates) and LT (100 ng LT per well of 2HB plates) as the coating antigen (in triplicates) and HRP-conjugated goat anti-mouse IgG (1:3300; Sigma) as the secondary antibodies. IgG titers (in log$_{10}$) were expressed in means ± standard deviation.
[b]p values were calculated by using a Student t test comparing mouse antibody titers in each group (15 mice immunized with CFA/I/II/IV-STa$_{N12S}$-LT$_{toxoid}$, 16 mice co-immunized with CFA/I/II/IV and 3xSTa$_{N12S}$-LT$_{toxoid}$).

Mice immunized with CFAXII/IV-STa$_{N12S}$-LT$_{toxoid}$ and mice co-immunized with CFA/I/II/IV and 3xSTa$_{N12S}$-LT$_{toxoid}$ fusions developed similar or comparable levels of anti-adhesin and antitoxin antibody responses. Serum samples of the mice immunized with fusion CFAXII/IV-STa$_{N12S}$-LT$_{toxoid}$ and the mice co-immunized with CFA/I/II/IV and 3xSTa$_{N12S}$-LT$_{toxoid}$ developed similar levels of IgG antibody responses to CS1, CS3, CS4/6, CS5/6 and LT. Serum of the co-immunized mice (with CFA/I/II/IV and 3xSTa$_{N12S}$-LT$_{toxoid}$ antigens) had greater titers of anti-CFA/I (2.69±0.05 vs 2.63±0.09), anti-CS2 (2.53±0.08 vs 2.44±0.10) and anti-STa (2.88±0.08 vs 2.50±0.52) IgG antibodies compared to the serum of the mice immunized with CFA/I/II/IV-STa$_{N12S}$-LT$_{toxoid}$ (Table 2).

Example 4

Serum samples of the immunized mice were shown to inhibit adherence of ETEC strains expressing CFA/I, CS3, CS4/CS6, CS5/CS6 or CS6 and E. coli strains expressing CS1 or CS2 to Caco-2 cells. Serum samples pooled from the mice co-immunized with CFA/I/II/IV and 3xSTa$_{N12S}$-LT$_{toxoid}$ exhibited significant inhibition activities against adherence of H10407 (CFA/I$^+$LT$^+$STa$^+$), E116 (CS3$^+$LT$^+$STa$^+$), E106 (CS4+CS6+LT$^+$STa$^+$), UM75688 (CS5$^+$CS6$^+$LT$^+$STa$^+$) and 2423/ETP98066 (CS6$^+$LT$^+$STa$^+$), and E. coli recombinant strains expressing CS1 adhesin or CS2 adhesins (Table 3). Serum sample pooled from the mice immunized with CFA/I/II/IV-STa$_{N12S}$-LT$_{toxoid}$ showed significant adherence inhibition activities against all examined ETEC and E. coli strains except the recombinant E. coli strain expressing CS2.

TABLE 3

Results of in vitro antibody adherence inhibition assays[a], using serum samples of mice immunized with CFA/I/II/IV-STa$_{N12S}$-LT$_{toxoid}$, co-administrated with CFA/I/II/IV MEFA and toxoid fusion 3xSTa$_{N12S}$-LT$_{toxoid}$, or the negative control mice.
The number of ETEC or E. coli bacteria adhered to Caco-2 cells incubated with pooled mouse serum and bacteria was used to indicate activity of anti-adhesin antibodies against bacteria adherence.

| | Mouse serum[b] | | |
|---|---|---|---|
| Bacteria (CFUs) | CFA/I/II/IV–STa$_{N12S}$-LT$_{toxoid}$ | CFA/I/II/IV + 3xSTa$_{N12S}$-LT$_{toxoid}$ | control |
| H10407; CFA/I, LT, STa (×10$^4$) | 14.4 ± 14.8 p[c] = 0.0018 | 39.7 ± 9.6 p = 0.017 | 107.5 ± 9.2 |
| THK38/pEU405; CS1 (×10$^3$) | 18.3 ± 7.7 p = 0.012 | 20.7 ± 11.6 p = 0.003 | 77 ± 7.1 |
| DH5a/pEU588; CS2 (×10$^3$) | 13.5 ± 4.8 p = 0.28 | 7.5 ± 4.5 p = 0.017 | 16.5 ± 2.1 |
| E116; CS3, LT, STa (×10$^3$) | 129 ± 49.9 p = 0.003 | 86 ± 49.6 p < 0.001 | 235 ± 7.1 |
| E106; CS4/CS6, LT, STa (×10$^4$) | 15.6 ± 3.3 p < 0.001 | 26.7 ± 3.9 p < 0.001 | 125 ± 0 |
| UM 75688; CS5/CS6, LT, STa (×10$^3$) | 59.5 ± 27.3 p = 0.029 | 55 ± 35.2 p = 0.025 | 110 ± 14.1 |
| ETP98066; CS6, LT, STa (×10$^4$) | 45.3 ± 28.6 p < 0.001 | 53.3 ± 27.1 p < 0.001 | 201.2 ± 29.5 |

[a]ETEC field isolates and E. coli recombinant strains expressing CFA/I, CS1, CS2, CS3, CS4/CS6, CS5/CS6 and CS6 (3.5 × 10$^6$ CFUs) were individually incubated with serum samples (20 µl) pooled from mice of the group immunized with CFA/I/II/IV-STa$_{N12S}$-LT$_{toxoid}$, the group co-immunized with the multiepitope CFA/I/II/IV and toxoid fusion 3xSTa$_{N12S}$-LT$_{toxoid}$, or serum samples of the control mice on a shaker (50 rpm) for 1 hour at room temperature. The serum-bacteria mixture was added to Caco-2 cells (7 × 10$^5$ cells; 1 ml final volume) and incubated in a CO$_2$ incubator for 1 hour. After washing off non-adherent bacteria, ETEC or E. coli bacteria adhered to Caco-2 cells (in 1 ml PBS) were serial diluted, plated, cultured overnight, and counted (CFUs).
[b]serum samples pooled from mice of the group immunized the CFA/I/II/IV-STa$_{N12S}$-dmLT, the group co-immunized with CFA/I/II/IV and 3xSTa$_{N12S}$-LT$_{toxoid}$, or the control group. These serum samples were used in the antibody adherence inhibition assay.
[c]p values were calculated by using a Student t test comparing numbers of ETEC or E. coli bacteria adhered to the Caco-2 cells incubated with mouse serum of each immunization group vs. bacteria adherent to the cells treated with serum of the control group.

Example 5

Constructed CFA-toxoid multiepitope fusion antigen proteins carried epitopes of 7 CFA adhesins, two copies of a STa toxoid, and a monomeric LT$_{A2-B}$ peptide (one copy of A2 peptide and one copy of B subunit to form a single peptide). Two recombinant strains, 9208 and 9401, were constructed to express two CFA-toxoid multiepitope fusion antigen proteins which differed only of the STa toxoid (Table 1). Both chimeric genes formed a single open reading frame, and expressed 6xHis-tagged fusion proteins consisted of a CFA multiepitope fusion antigen (170 amino acids) carrying epitopes of CFA/I and CS1-CS6 major subunits (CfaB, CooA, CotA, CstH, CsaB, CsfA and CssA), 2 copies of STa$_{toxoid}$ STa$_{A14Q}$ or STa$_{N12S}$, 110 amino acids (131-240) of LT$_{A1}$ peptide, and one copy of the LT$_B$ subunit (100 amino acids), and 4 intrapeptide linkers (FIG. 5). The first copy of the STa toxoid, with a 'GPVD' linker at the N-terminus, was inserted after the mutated LT$_A$ 192th amino acid residue (Arg→Gly), and the other copy of the STa$_{toxoid}$ was at the end of the fusion protein C-terminus SDS-PAGE with Coomassie blue staining showed over 90% of the His-tagged proteins extracted from strains 9208 and 9401 had a molecular weight of about 48 Kda, an expected size of the 6xHis-tagged CFAI/II/IV-STa$_{toxoid}$-LT$_{toxoid}$ fusion protein. Refolded 6xHis-tagged fusion proteins were recognized by rabbit anti-STa and anti-CT serum, and anti-CFA/I MAb.

Example 6

The CFA-toxoid multiepitope fusion antigen proteins were safe and immunogenic. T-84 cells incubated with fusion protein CFA/I/II/IV-STa$_{A14Q}$-LT$_{toxoid}$ or CFA/I/II/IV-STa$_{N12S}$-LT$_{toxoid}$ showed no increase of intracellular cAMP or cGMP levels. That indicated that both fusion proteins did not possess LT or STa enterotoxicity. Additionally, female adult mice did not display noticeable adverse effects after i.p. immunization of either fusion protein, or co-administration of the CFA multiepitope fusion antigen protein with 3xSTa$_{N12S}$-LT$_{toxoid}$ toxoid fusion.

Figure 6:
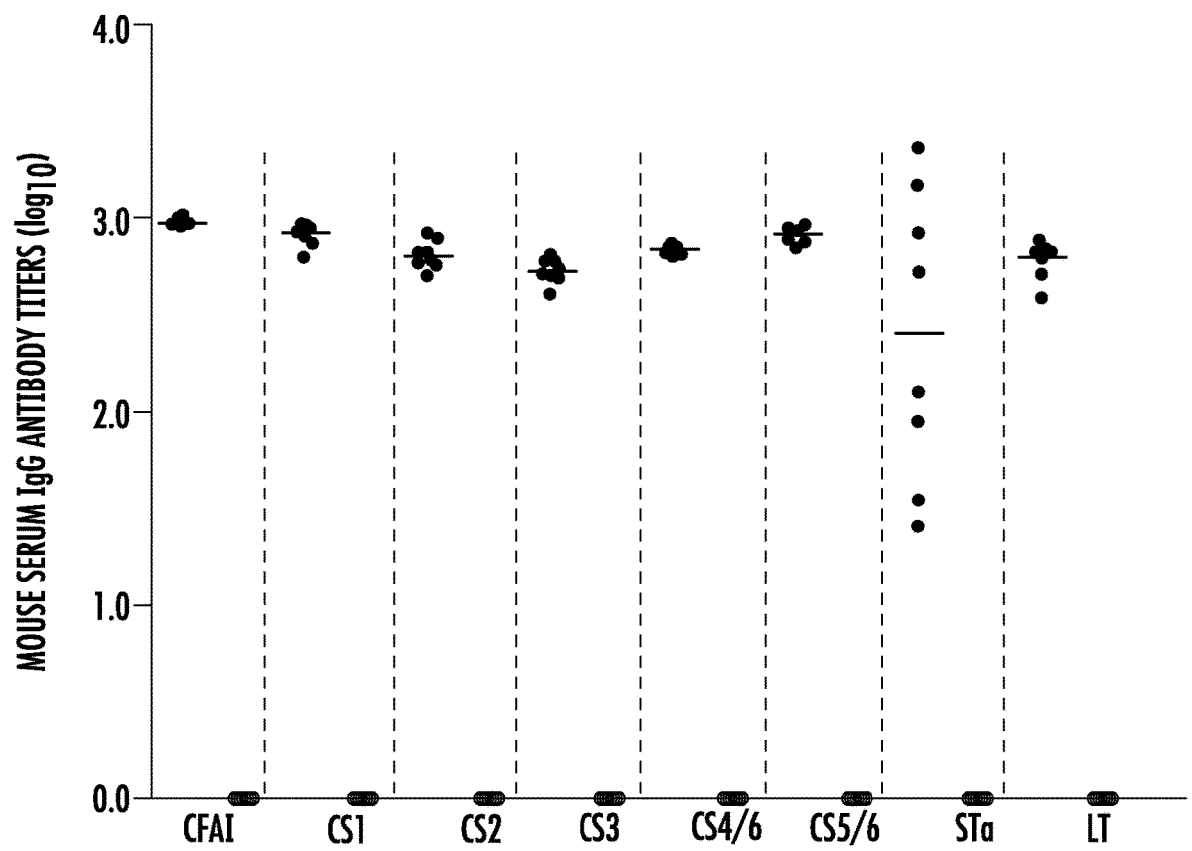
FIG. 6 shows the titration of anti-CFA/I, -CS1, -CS2, -CS3, -CS4/CS6, -CS5/CS6, -STa, and anti-LT IgG antibodies in serum samples of the mice immunized with 'CFA/I/II/IV-STa$_{414Q}$-LT$_{toxoid}$' fusion antigen (solid circles) and the control mice (blank circles). Five hundred nanograms of CFA adhesins heat-extracted from *E. coli* strains expressing CFA/I, CS1, CS2, CS3, CS4/CS6, CS5/CS6, 10 ng STa-ovalbumin, or 100 ng LT (List Biological Laboratories, Inc.) were coated to each well of an Immulon 2HB plate or a Costar plate to titrate anti-CFA/I, -CS1, -CS2, -CS3, -CS4/CS6, -CS5/CS6, -STa, and anti-LT IgG antibodies, respectively. Serum samples from each mouse (1:200 dilution) were added to each well (in triplicate). HRP-conjugated goat-anti-mouse IgG (1:3000) was used as the secondary antibodies. Optical densities of greater than 0.3 (after subtracting the background reading) were used to calculate anti-STa antibody titers (in $\log_{10}$).
Figure 7:
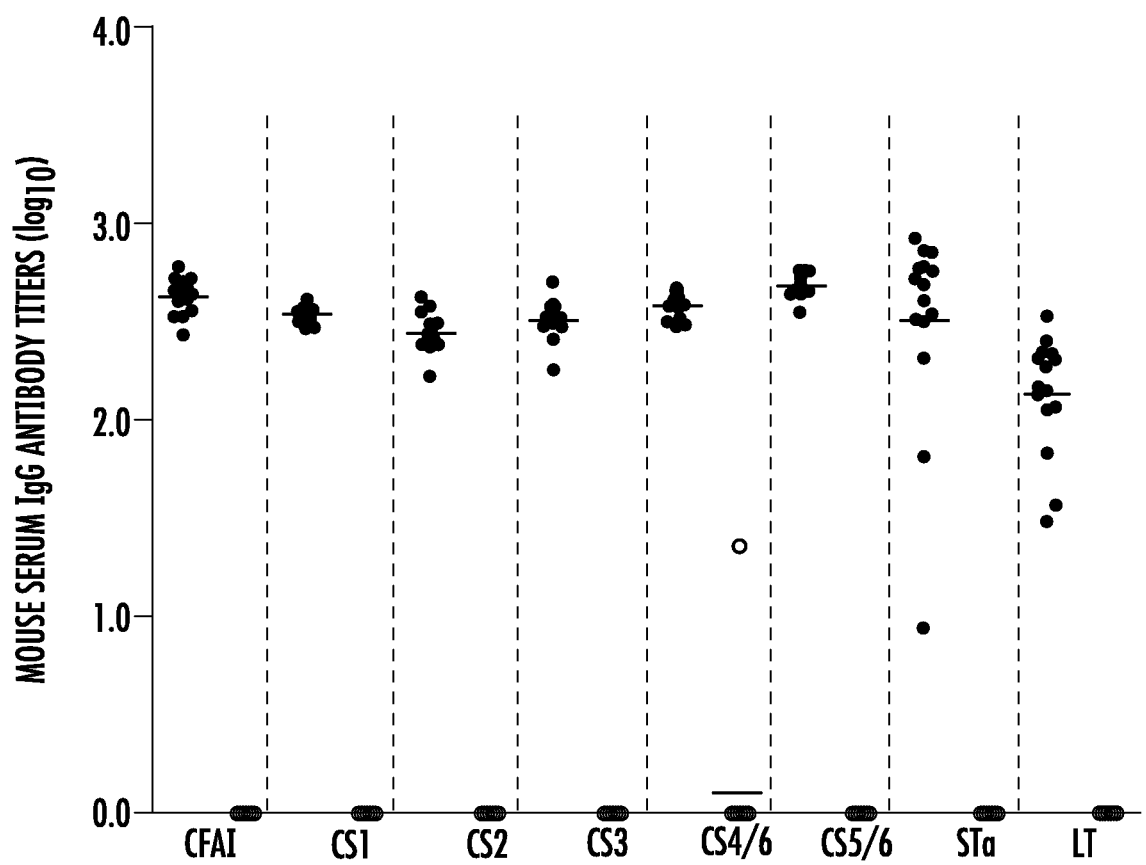
FIG. 7 shows the titration of anti-CFA/I, -CS1, -CS2, -CS3, -CS4/CS6, -CS5/CS6, -STa, and anti-LT IgG antibodies in serum samples of the mice immunized with CFA/I/II/IV-STa$_{N12S}$-LT$_{toxoid}$' fusion antigen (solid circles) and serum samples collected prior to immunization (blank circles).
Figure 8:
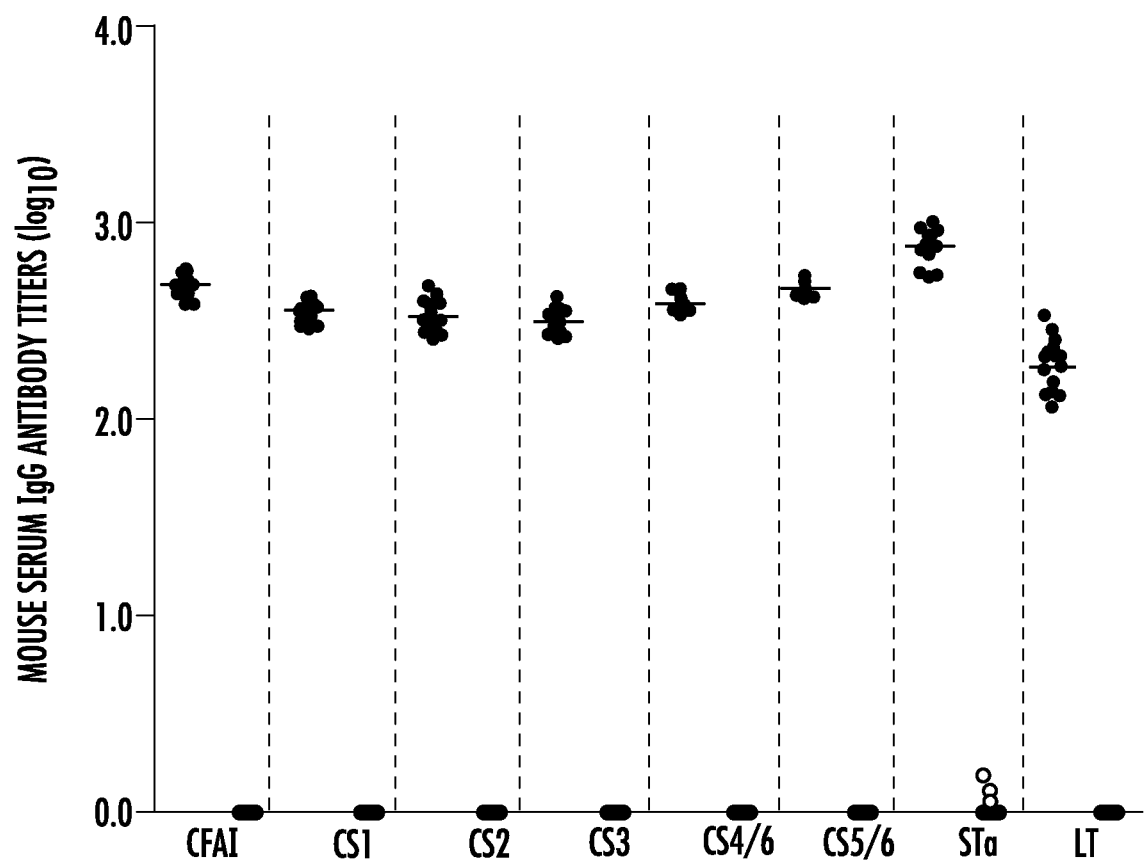
FIG. 8 depicts the titration of anti-CFA/I, -CS1, -CS2, -CS3, -CS4/CS6, -CS5/CS6, -STa, and anti-LT IgG antibodies in serum samples of the mice co-administered with the e CFA MEFA and '3xSTa$_{N12S}$-LT$_{toxoid}$' fusion (solid circles) and serum samples collected prior to immunization (blank circles).

Mice immunized with CFA/I/II/IV-STa$_{A14Q}$-LT$_{toxoid}$, CFA/I/II/IV-STa$_{N12S}$-LT$_{toxoid}$, or co-administered with CFA multiepitope fusion antigen and the 3xSTa$_{N12S}$-LT$_{toxiid}$ toxoid fusion developed immune responses to CFA/I, CS1, CS2, CS3, CS4/6, CS5/6, STa, and LT. Serum samples from mice immunized with fusion CFA/I/IFIV-STa$_{A14Q}$-LT$_{toxoid}$ had anti-CFA/I, -CS1, -CS2, -CS3, -CS4/6, -CS5/6, -STa, and anti-LT IgG antibodies detected at titers (in log$_{10}$) of 2.98±0.02, 2.92±0.06, 2.81±0.07, 2.73±0.07, 2.84±0.03, 2.92±0.04, 2.40±0.75, and 3.19±0.01, respectively (FIG. 6). Serum samples from mice immunized with fusion CFA/I/II/IV-STa$_{N12S}$-LT$_{toxoid}$ had IgG antibodies specific to CFA/I, CS1, CS2, CS3, CS4/6, CS5/6, STa, and LT detected at titers (in log$_{10}$) of 2.63±0.09, 2.54±0.04, 2.44±0.10, 2.50±0.09, 2.58±0.06, 2.66±0.03, 2.5±0.52, and 2.12±0.30, respectively (FIG. 7). For the group of mice co-administered with the CFA multiepitope fusion antigen and the 3xSTa$_{N12S}$-LT$_{toxoid}$ toxoid fusion, anti-CFA/I, -CS1, -CS2, -CS3, -CS4/6, -CS5/6, -STa, and anti-LT IgG antibodies were titrated at 2.69±0.05, 2.56±0.05, 2.53±0.08, 2.50±0.06, 2.59±0.03, 2.67±0.05, 2.88±0.08, and 2.27±0.13 (in log$_{10}$) from the serum samples (FIG. 8). No anti-CFA, anti-STa, or anti-LT IgG antibodies were detected in serum samples of the control mice, or serum samples collected prior to immunization except one sample that was collected from one pre-immunized mouse and had a low anti-CS4/CS6 IgG titer detected.

Example 7

Figure 9:
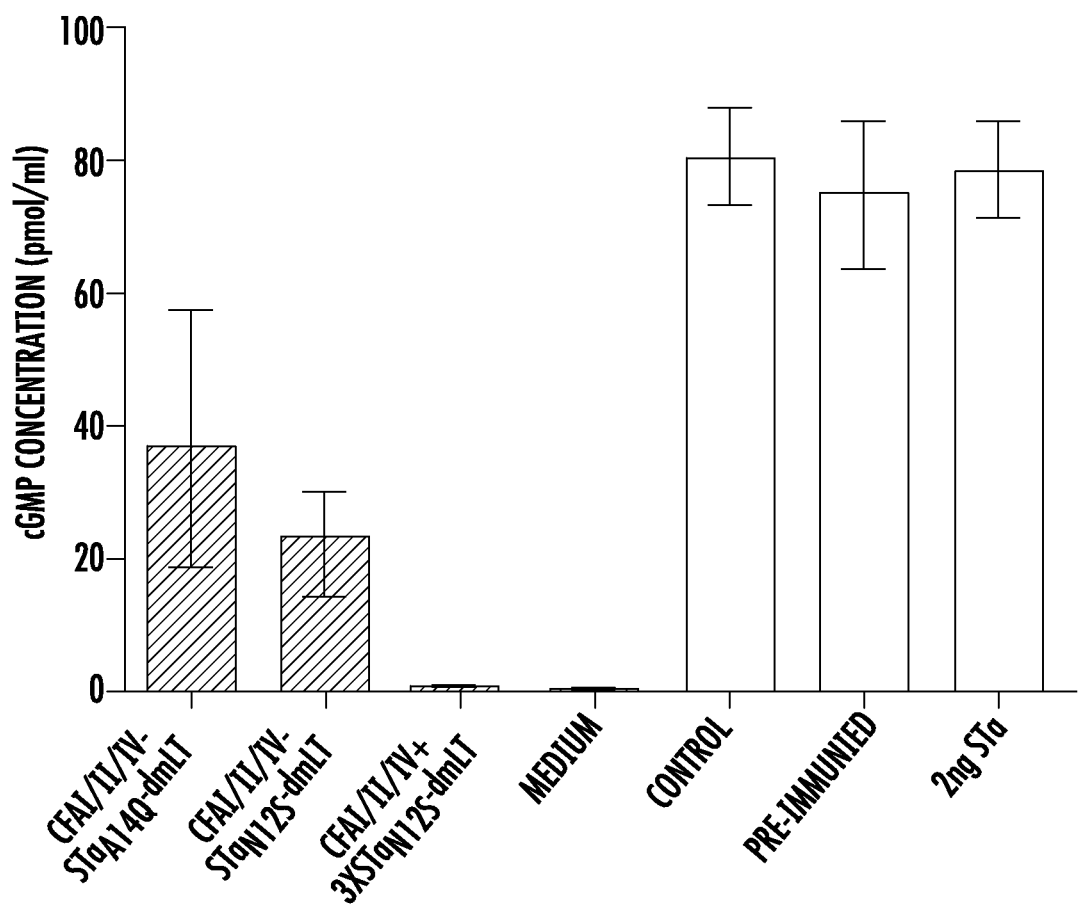
FIG. 9 depicts mouse serum in vitro antibody neutralization activity against STa toxin. Intracellular cyclic GMP concentration (pmole/ml) in T-84 cells incubated with STa toxin and mouse serum was measured with an EIA cGMP ELISA kit (Assay Design) and was used to indicate anti-STa antibody neutralizing activity. As STa toxin elevates intracellular cGMP in T-84 cells, while neutralizing anti-STa antibodies neutralize the toxin and prevent STa from stimulating cGMP, a lower cGMP concentration indicates a stronger neutralization activity of anti-STa antibodies. The serum sample (30 μl; in a final dilution of 1:33.3) pooled from each group of mice immunized with 'CFA/I/II/IV-STa$_{A14Q}$-LT$_{toxoid}$', CFA/I/II/IV-STa$_{N12S}$-LT$_{toxoid}$', co-immunized with 'CFA/I/II/IV' and '3xSTa$_{N12S}$-LT$_{toxoid}$', the control group, or the serum sample collected prior to immunization was incubated with STa toxin (2 ng, in 150 μl cell culture medium) for 30 minutes at room temperature, and the serum-toxin mixture was added to T-84 cells (1 ml of final volume with cell culture medium). Intracellular cGMP concentration in T-84 cells was measured after 1 hour incubation at a CO$_2$ incubator, with the mean cGMP and standard deviation (from four to six replicates) of each group indicated as columns and bars. The cGMP in T-84 cells cultured with cell culture medium alone (without STa toxin or serum; no STa toxicity), or with STa toxin in culture medium (without serum; STa toxicity) were used as references.

Antibodies in serum samples of the immunized mice showed neutralizing activities against STa toxin and CT in vitro. Pooled serum samples from mice immunized with 'CFA/I/II/IV-STa$_{A14Q}$-LT$_{toxoid}$', 'CFA/I/IFIV-STa$_{N12S}$-LT$_{toxoid}$', or co-immunized with 'CFA/I/II/IV' and '3xSTa$_{N12S}$-LT$_{toxoid}$' showed neutralization activity against STa (FIG. 9) and CT toxins (data not shown). Intracellular cGMP levels in T-84 cells incubated with 2 ng STa toxin and serum of mice immunized with 'CFA/I/IFIV-STa$_{A14Q}$-LT$_{toxoid}$', 'CFA/I/II/IV-STa$_{N12S}$-LT$_{toxoid}$', and 'CFA/I/II/IV' with '3xSTa$_{N12S}$-LT$_{toxoid}$' were 36.7±20.7, 23.2±7.0, 0.31±0.36 (pmole/ml), respectively. Whereas the cGMP levels in T-84 cells incubated with 2 ng STa toxin and serum of the control mice or serum collected pre-immunized mice were 80.7±7.3 and 75.1±11.2 (pmole/ml), which was equivalent to the cGMP in T-84 cells incubated with 2 ng STa toxin alone (78.7±7.2 pmole/ml; p=0.78, 0.63).

Figure 16:
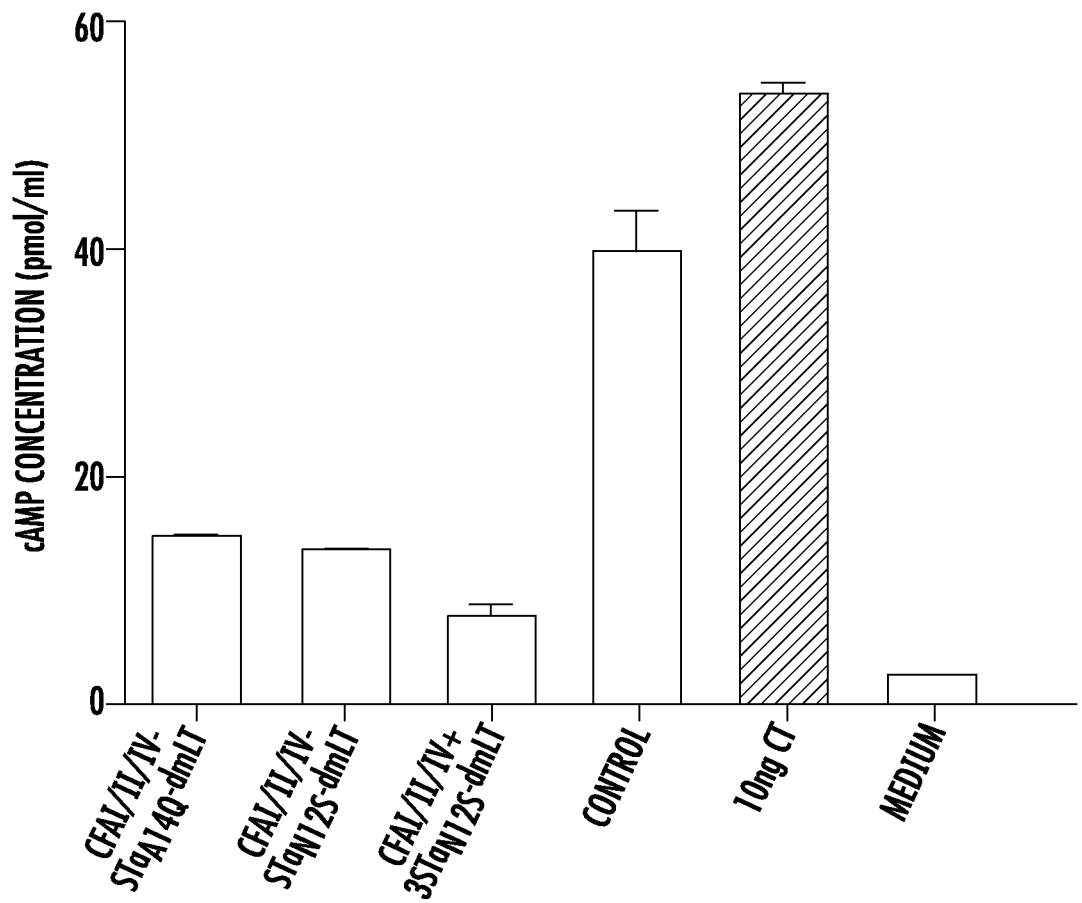
FIG. 16 shows mouse serum in vitro antibody neutralization activity against cholera toxin (CT). Intracellular cAMP concentrations (pmole/ml) in T-84 cells measured with an EIA cAMP ELISA kit (Assay Design) were used to indicate anti-LT antibody neutralizing activity. Neutralizing anti-LT antibodies neutralize CT toxin and prevent CT from stimulating cAMP in T-84 cells, thus resulting in a lower intracellular cAMP level. The serum sample (30 μl; in a final dilution of 1:33.3) pooled from each group of mice immunized with 'CFA/I/II/IV-STa$_{A14Q}$-LT$_{toxoid}$', 'CFA/I/II/IV-STa$_{N12S}$-LT$_{toxoid}$', co-immunized with 'CFA/I/II/IV' and '3xSTa$_{N12S}$-LT$_{toxoid}$', or the control group was incubated with CT toxin (10 ng, in 150 μl cell culture medium) for 30 minutes at room temperature, and the serum-toxin mixture was added to T-84 cells (1 ml of final volume with cell culture medium). Intracellular cAMP concentration (pmole/ml) in T-84 cells was measured after 3 hour incubation at a CO$_2$ incubator, with the mean cAMP and standard deviation (from four to six replicates) of each group indicated as columns and bars. The cAMP in T-84 cells incubated with cell culture medium alone (without CT or serum; no CT toxicity), or with CT in culture medium (without serum; CT toxicity) were also measured as references.

The cAMP levels in T-84 cells incubated with CT (10 ng) and the pooled serum sample of mice immunized with 'CFA/I/II/IV-STa$_{A14Q}$-dmLT', 'CFA/I/II/IV-STa$_{N12S}$-dmLT', or 'CFA/I/II/IV' co-immunized with '3xSTa$_{N12S}$-dmLT' were 14.4±0.51, 12.8±0.76, and 7.7±2.4 pmole/ml, respectively (FIG. 16). These cAMP levels were significantly lower than those in cells incubated with the toxin alone (53.7±1.3; p<0.01)) or with the toxin and the serum sample of the control mice (40.1±6.5; p<0.01).

Example 8

In accordance with some other embodiments, the present invention provides a modification of the CFA-STa$_{N12S}$-LT$_{toxoid}$ MEFA of the present invention. This embodiment comprises 3 copies of the toxoid STa$_{N12S}$ in order to further enhance the fusion antigen anti-STa immunogenicity, and it does not carry the histidine-tag so that the new antigen is suitable for human vaccine development. The nucleic acid and amino acid sequences are shown in FIGS. 17A-17C.

Figures 18A, 18B, 18C:
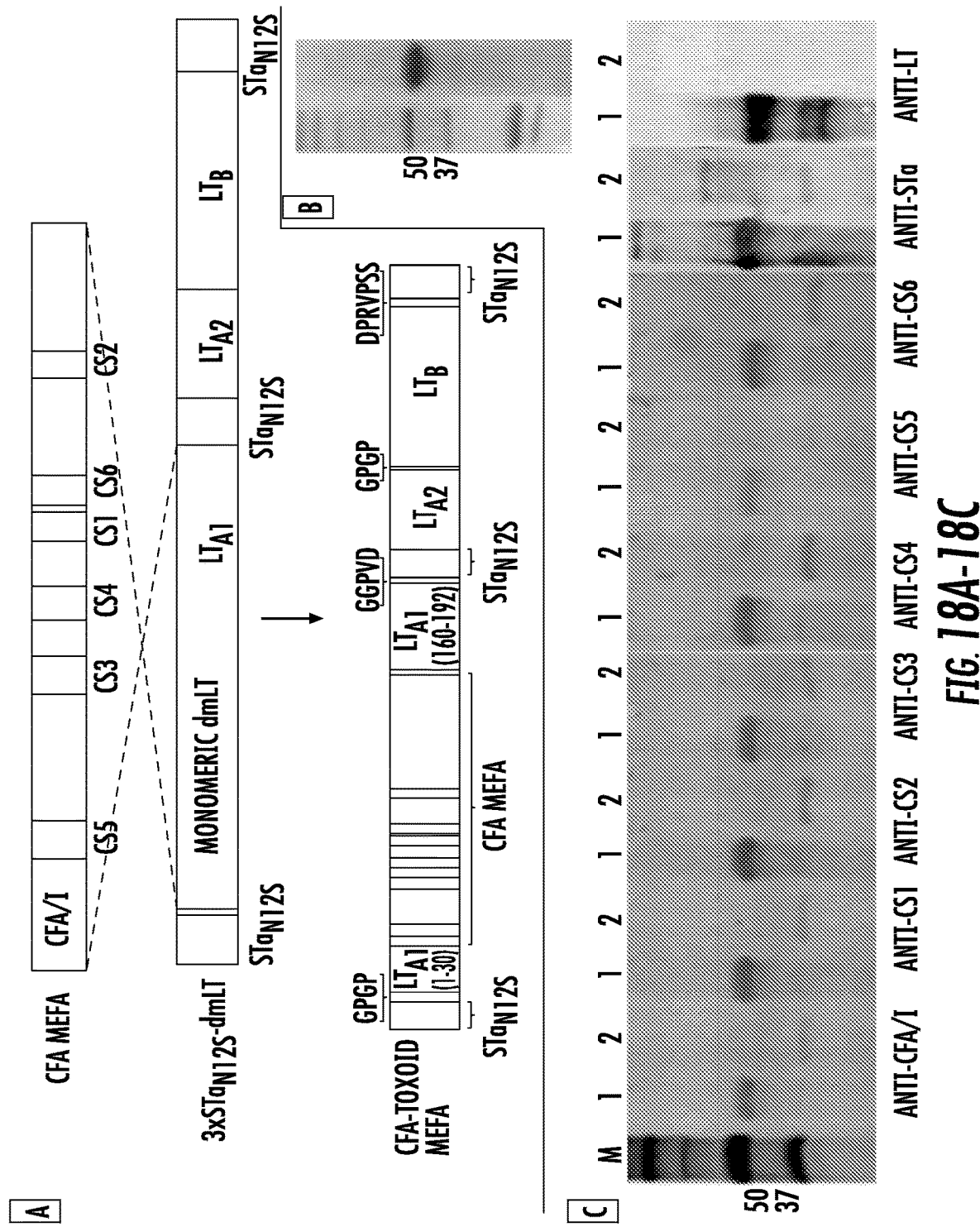
FIG. 18A is a schematic showing the CFA-toxoid MEFA carries 3 copies of STa$_{N12S}$ at the N terminus, the C-terminus, and after the 192 residue of the LT A subunit gene, the CFA MEFA, and 160 to 192 AAs and 193 to 240 AAs of the LT A, and the LT B subunit.
FIG. 18B is a photograph of a Coomassie blue staining gel showed purity of the extracted his-tag-less CFA-3xSTa$_{N12S}$-LT$_{toxoid}$ MEFA protein to be used to immunize mice and pregnant sow.
FIG. 18C is a photograph of Western blots showing detection of this his-tag-less CFA-3xSTa$_{N12S}$-LT$_{toxoid}$ MEFA protein by anti-CFA mAbs hybridoma supernatant (provided by Dr. AM Svennerholm), and anti-STa and anti-CT rabbit serum. Lane M, the protein marker; lane 1, extracted proteins of 9419; lane 2, total protein of host E. coli BL21.

As shown in FIG. 18A, This CFA-toxoid MEFA carries 3 copies of STa$_{N12S}$ at the N terminus, the C-terminus, and after the 192 residue of the LT A subunit gene, the CFA MEFA, and 160 to 192 AAs and 193 to 240 AAs of the LT A, and the LT B subunit (see followed sequences and genetic structure). Four linkers were included: GPGP (SEQ ID NO: 37), GGPVD (SEQ ID NO: 38), GPGP (SEQ ID NO: 37), and DPRVPSS (SEQ ID NO: 39), to connect the STa$_{N12S}$ with the LT, as well as the LTA with the LTB.

A Coomassie blue staining gel showed purity of the extracted his-tag-less CFA-3xSTa$_{N12S}$-LT$_{toxoid}$ MEFA protein to be used to immunize mice and pregnant sow (FIG. 18B). Western blotting showed detection of this his-tag-less CFA-3xSTa$_{N12S}$-LT$_{toxoid}$ MEFA protein by anti-CFA mAbs hybridoma supernatant (provided by Dr. AM Svennerholm), and anti-STa and anti-CT rabbit serum. Lane M, the protein marker; lane 1, extracted proteins of 9419; lane 2, total protein of host E. coli BL21 (FIG. 18C).

Figure 19:
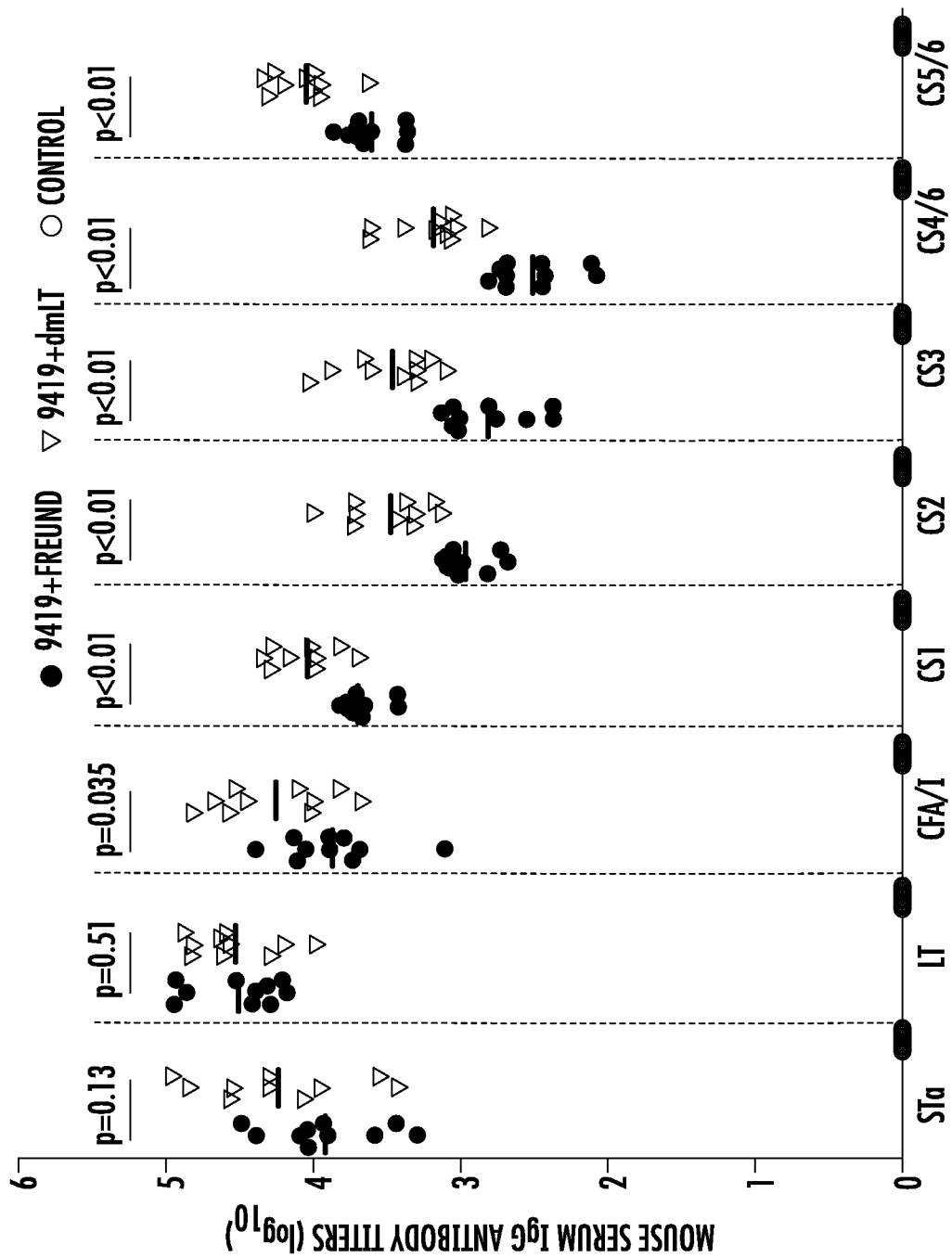
FIG. 19 is a graph depicting titers of anti-STa antibodies in intraperitoneally immunized mice.
Figure 21A:
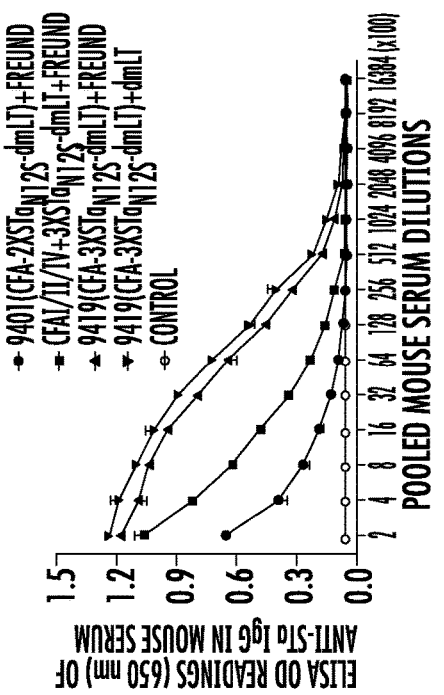
Figure 21B:
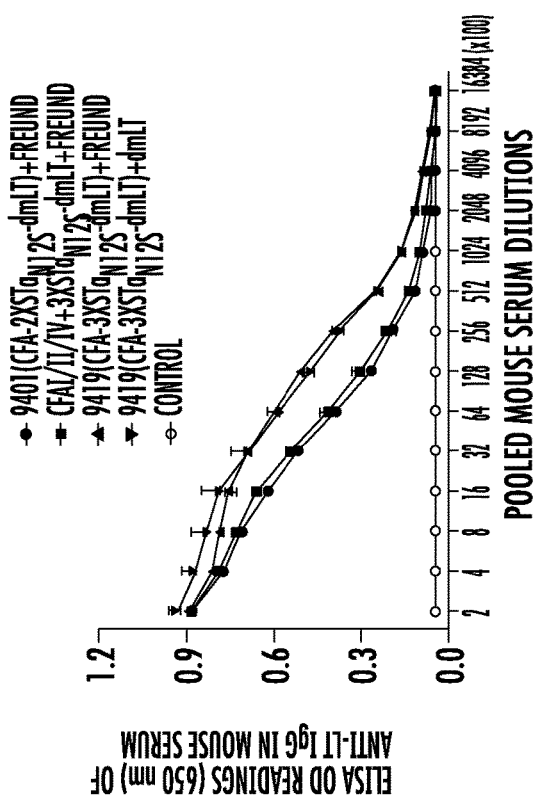
Figure 21C:
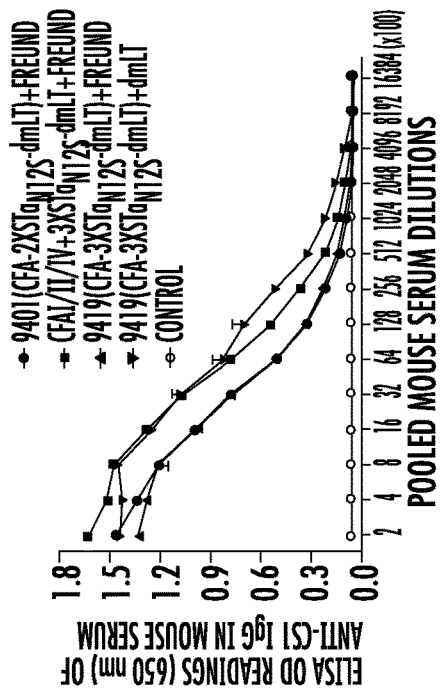
Figure 21D:
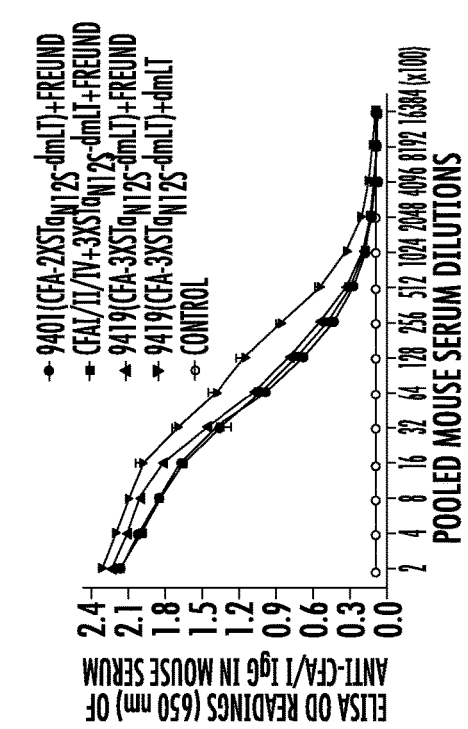

The his-tag-less CFA-3xSTa$_{N12S}$-LT$_{toxoid}$ MEFA induces greater titers of anti-STa antibodies in intraperitoneally immunized mice (FIG. 19), and that induced anti-STa antibodies in mouse serum can completely neutralize STa toxin (FIG. 20).

In addition, the double mutant LT (LT$_{R192G/L211A}$; gift from PATH) was found an effective adjuvant to enhance the his-tag-less CFA-3xSTa$_{N12S}$-LT$_{toxoid}$ MEFA in inducing antibody responses to all 7 adhesins and both toxins. For the first time this dmLT is an effective adjuvant in mouse parenteral immunization when combined with the his-tag-less CFA-3xSTa$_{N12S}$-LT$_{toxoid}$ MEFA of the present invention (FIG. 21A-21H).

Example 9

The inventors carried out a pig immunization and challenge study to assess protective efficacy of the anti-STa antibodies induced by the his-tag-less CFA-3xSTa$_{N12S}$-LT$_{toxoid}$ MEFA against STa ETEC infection. Pregnant sows 6-8 weeks before farrowing was intramuscularly immunized with 500 µg of the his-tag-less CFA-3xSTa$_{N12S}$-LT$_{toxoid}$ MEFA protein with 5 µg dmLT (as adjuvant). The immunized sows received a booster at the same dose two weeks before farrowing. A sow without immunization was used as the control. Born piglets were orally challenged with $5 \times 10^9$ or $2 \times 10^{10}$ CFUs of a STa ETEC recombinant strain 8823 (pSTa/987P) after 24 hours suckling to acquire maternal antibodies. Challenged piglets were monitored every 3-4 hours during 24 hour post-inoculation, and clinical symptoms including diarrhea, vomiting, dehydration and lethargy were recorded. In addition, each piglet was weighed before and 24 hours after the challenge.

Immunized sow developed IgG and IgA antibodies in serum and colostrum (Table A). Piglets born by IM immunized sow acquired maternal anti-STa (& also anti-LT and anti-CFA) antibodies. When challenged with a STa ETEC strain ($5 \times 10^9$ or $2 \times 10^{10}$ CFUs), these piglets were protected as they showed no diarrhea (only 2 of 12 had yellow pasty feces) (Table B), and maintained daily weight gain (Table C). In contrast, piglets born the control sow developed severe diarrhea (3 out 7 challenged with $5 \times 10^9$, and 5 out 6 challenged with $2 \times 10^{10}$) and showed daily weight loss.

TABLE A

Sow colostrum and serum anti-STa IgG and IgA antibody titers (in log$_{10}$)

| Colostrum IgG | | Colostrum IgA | | Serum IgG | | Pre-immunization serum IgG | | Pre-booster serum IgG | |
|---|---|---|---|---|---|---|---|---|---|
| cont | immun | cont | immuni | cont | immun | cont | immun | cont | immun |
| 0 | 3.07 ± 0.05 | 0 | 1.15 ± 0.03 | 0 | 2.32 ± 0.05 | 0 | 0 | 0 | 0 |

TABLE B

Results from piglet challenge studies to show maternal antibodies against STa+ ETEC infection. A pregnant sow 7 weeks before fallowing was IM immunized with 500 µg CFA-3xSTa$_{N12S}$-LT$_{toxoid}$ with 5 µg dmLT as adjuvant, and a booster at the same dose 2 weeks before fallowing. A pregnant sow received no immunization severed as the control. Piglets born by the immunized sow and the control sow were challenged with STa+ ETEC strain 8823 (pSTa/987P) at day two, and euthanized 24 h post-challenge.

| Challenge doses (CFUs) | Treatments | Severe diarrhea (with dehydration) | Watery diarrhea | Mild diarrhea (yellow pasty feces) | Healthy |
|---|---|---|---|---|---|
| $5 \times 10^9$ | immunized (n = 6) | 0 | 0 | 1 | 5 |
| | control (n = 7) | 2 | 2 | 0 | 3 |
| $2 \times 10^{10}$ | immunized (n = 6) | 0 | 0 | 1 | 5 |
| | control (n = 6) | 1 | 4 | 0 | 1 |

TABLE C

Weight gain or loss (%) of piglets born by the immunized sow or the control sow after challenged with the STa ETEC strain.

| piglets | challenged with 5 × 10$^9$ CFUs | | | | | | | challenged with 2 × 10$^{10}$ CFUs | | | | | | overall gain or loss | | |
|---|---|---|---|---|---|---|---|---|---|---|---|---|---|---|---|---|
| | #1 | #2 | #3 | #4 | #5 | #6 | #7 | #8 | #9 | #10 | #11 | #12 | #13 | mean | stdev | p value |
| control (n = 13) | 10 | 0 | 5.3 | 13 | 0 | −6.7 | 5.5 | −9.1 | −23.1 | 0 | −16.7 | 6.7 | 12.5 | −0.2 | 11.1 | 0.01 |
| immunized (n = 12) | 9.7 | 9.4 | 11.8 | 7.7 | 6.3 | 3.8 | | 9.5 | 14.3 | 6.3 | 7.1 | 10.5 | 8 | 8.7 | 2.8 | |

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A fusion polypeptide molecule which comprises the colonization factor antigen (CFA) antigenic epitopes of CFA/I (SEQ ID NO: 4), CFA/II (CS1 (SEQ ID NO: 5), CS2 (SEQ ID NO: 6), CS3 (SEQ ID NO: 7), CFA/IV (CS4 (SEQ ID NO: 8), CS5 (SEQ ID NO: 9), and CS6 (SEQ ID NO: 10), and wherein the polypeptide comprises the amino acid sequence of SEQ ID NO: 1, or having at least 90% sequence identity to SEQ ID NO: 1.

2. A pharmaceutical composition comprising the fusion polypeptide molecule of claim 1, and a pharmaceutically acceptable carrier.

3. A method for developing an immune response to colonization factor antigen (CFA) antigenic epitopes of CFA/I (SEQ ID NO: 4), CFA/II (CS1 (SEQ ID NO: 5), CS2 (SEQ ID NO: 6), CS3 (SEQ ID NO: 7), CFA/IV (CS4 (SEQ ID NO: 8), CS5 (SEQ ID NO: 9), and CS6 (SEQ ID NO: 10) in a subject comprising administering to the subject an effective amount of a polypeptide molecule consisting of the amino acid sequence of SEQ ID NO: 1.

4. The method of claim 3, wherein the polypeptide is administered to the subject in a vaccine formulation.

5. The method of claim 3, further comprising administration of at least one additional therapeutic agent.

6. The method of claim 5, wherein the additional therapeutic agent is selected from the group consisting of: antimotility, antidiarrheals, antibiotics, antihelminths, and antiparasiticals.

* * * * *